(12) United States Patent
Bachinski et al.

(10) Patent No.: US 11,439,820 B2
(45) Date of Patent: *Sep. 13, 2022

(54) DEVICES, SYSTEMS AND METHODS FOR TREATING PAIN WITH ELECTRICAL STIMULATION

(71) Applicant: DJO, LLC, Vista, CA (US)

(72) Inventors: Thomas Jerome Bachinski, Lakeville, MN (US); Dain Silvola, St. Paul, MN (US); Michael Moore, Oceanside, CA (US); Jay Dave, San Marcos, CA (US); Joseph Winn, Aliso Viejo, CA (US)

(73) Assignee: DJO, LLC, Vista, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/571,685

(22) Filed: Sep. 16, 2019

(65) Prior Publication Data

US 2020/0078590 A1 Mar. 12, 2020

Related U.S. Application Data

(63) Continuation of application No. 15/681,177, filed on Aug. 18, 2017, now Pat. No. 10,413,723, which is a
(Continued)

(51) Int. Cl.
*A61N 1/36* (2006.01)
*A61N 1/04* (2006.01)
(Continued)

(52) U.S. Cl.
CPC ....... *A61N 1/36021* (2013.01); *A61N 1/0456* (2013.01); *A61N 1/36034* (2017.08);
(Continued)

(58) Field of Classification Search
CPC ...... A61N 1/044; A61N 1/0472; A61N 1/303; A61N 1/36014; A61N 1/36021
See application file for complete search history.

(56) References Cited

U.S. PATENT DOCUMENTS 3,163,166 A 12/1964 Brant et al.
3,902,502 A 9/1975 Liss et al.
(Continued)

FOREIGN PATENT DOCUMENTS

GB 2 372 705 9/2002

OTHER PUBLICATIONS

Partial International Search Report dated Nov. 7, 2012, International Application No. PCT/US2012/050003 (8 pages).
(Continued)

*Primary Examiner* — Joseph M Dietrich
(74) *Attorney, Agent, or Firm* — Knobbe Martens Olson & Bear LLP

(57) ABSTRACT

Devices, systems and methods are provided for treating migraine headaches and other conditions by non-invasive electrical stimulation of nerves and other tissue. A hand-held device includes a housing with a controller having a signal generator, an electrode for delivering electrical signals, and a conductive surface configured as a return path for the electrical signals. In certain implementations, the electrode is repositionable with respect to the housing. The patient can self-apply the hand-held device by pressing it against areas in need of pain relief. The device may include a pressure-sensitive gating switch to control delivery of the stimulation therapy. In certain embodiments, the electrode is a rollerball electrode. The device may include a chamber for retaining and dispensing conductive gel to the therapy site. In certain approaches, the device includes an electrode support for coupling an electrical stimulation system to the head for hands-free electrical stimulation therapy.

19 Claims, 23 Drawing Sheets

Related U.S. Application Data continuation of application No. 14/744,335, filed on Jun. 19, 2015, now Pat. No. 9,737,709, which is a continuation of application No. 13/570,004, filed on Aug. 8, 2012, now Pat. No. 9,061,148.

(60) Provisional application No. 61/658,756, filed on Jun. 12, 2012, provisional application No. 61/538,015, filed on Sep. 22, 2011.

(51) Int. Cl.
| | |
|---|---|
| *A61H 39/00* | (2006.01) |
| *A61H 39/04* | (2006.01) |
| *A61H 23/02* | (2006.01) |
| *A61H 39/08* | (2006.01) |
| *A61N 1/372* | (2006.01) |

(52) U.S. Cl.
CPC ............ *A61H 23/02* (2013.01); *A61H 39/002* (2013.01); *A61H 39/04* (2013.01); *A61H 39/08* (2013.01); *A61H 2201/0153* (2013.01); *A61H 2201/0157* (2013.01); *A61H 2201/0184* (2013.01); *A61H 2201/0188* (2013.01); *A61H 2201/10* (2013.01); *A61H 2201/1604* (2013.01); *A61H 2201/1609* (2013.01); *A61H 2201/1635* (2013.01); *A61H 2201/1685* (2013.01); *A61H 2201/501* (2013.01); *A61H 2201/5007* (2013.01); *A61H 2201/5012* (2013.01); *A61H 2201/5028* (2013.01); *A61H 2201/5035* (2013.01); *A61H 2201/5043* (2013.01); *A61H 2201/5048* (2013.01); *A61H 2201/5082* (2013.01); *A61H 2205/02* (2013.01); *A61H 2205/022* (2013.01); *A61H 2205/04* (2013.01); *A61H 2205/062* (2013.01); *A61H 2205/065* (2013.01); *A61H 2205/081* (2013.01); *A61H 2205/10* (2013.01); *A61H 2205/12* (2013.01); *A61H 2230/065* (2013.01); *A61H 2230/605* (2013.01); *A61H 2230/655* (2013.01); *A61N 1/37264* (2013.01)

(56) References Cited

U.S. PATENT DOCUMENTS

| | | | |
|---|---|---|---|
| 4,095,601 | A | 6/1978 | Aufranc et al. |
| 4,155,366 | A * | 5/1979 | Di Mucci .......... A61N 1/36021 607/46 |
| 4,509,521 | A | 4/1985 | Barry |
| 4,537,195 | A | 8/1985 | McDonnell |
| 4,627,438 | A | 12/1986 | Liss et al. |
| 4,856,526 | A | 8/1989 | Liss et al. |
| 4,989,605 | A | 2/1991 | Rossen |
| 4,997,418 | A | 3/1991 | DeMartini |
| 5,109,847 | A | 5/1992 | Liss et al. |
| 5,514,175 | A | 5/1996 | Kim et al. |
| 5,540,736 | A | 7/1996 | Haimovich et al. |
| 5,569,166 | A | 10/1996 | Stone |
| 6,023,642 | A | 2/2000 | Shealy et al. |
| 6,132,392 | A | 10/2000 | Stone |
| 6,402,678 | B1 | 6/2002 | Fischell et al. |
| 7,660,637 | B2 | 2/2010 | Szeles |
| 9,061,148 | B2 | 6/2015 | Bachinski et al. |
| 9,737,709 | B2 | 8/2017 | Bachinski et al. |
| 10,413,723 | B2 | 9/2019 | Bachinski |
| 2002/0132208 | A1 | 9/2002 | Magnani |
| 2003/0097118 | A1 | 5/2003 | Zhang et al. |
| 2005/0102006 | A1 | 5/2005 | Whitehurst et al. |
| 2006/0004423 | A1 | 1/2006 | Boveja et al. |
| 2006/0047316 | A1 | 3/2006 | Fischell et al. |
| 2006/0206165 | A1 | 9/2006 | Jaax et al. |
| 2006/0259094 | A1 | 11/2006 | Naisberg et al. |
| 2007/0276449 | A1 | 11/2007 | Gunter et al. |
| 2008/0300593 | A1 | 12/2008 | Mulier et al. |
| 2009/0182393 | A1 | 7/2009 | Bachinski |
| 2010/0030299 | A1 | 2/2010 | Covalin |
| 2010/0312233 | A1 | 12/2010 | Furnish et al. |
| 2011/0196267 | A1 | 8/2011 | Mishelevich |
| 2011/0218589 | A1 | 9/2011 | DeGiorgio et al. |
| 2011/0230701 | A1 | 9/2011 | Simon et al. |
| 2011/0230938 | A1 | 9/2011 | Simon et al. |

OTHER PUBLICATIONS

International Search Report and Written Opinion dated Mar. 6, 2013 in PCT/US12/050003.

* cited by examiner

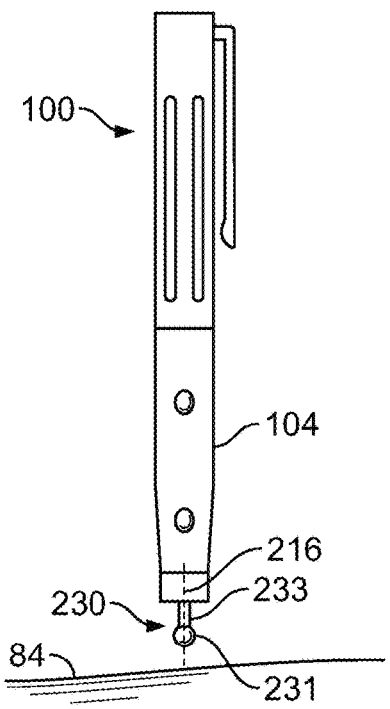
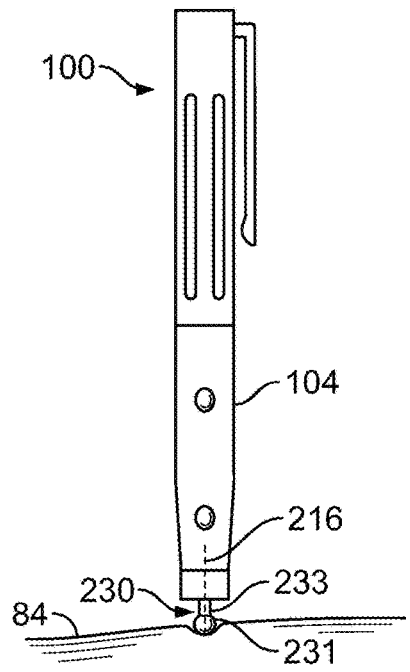
FIG. 9A　　　　　　FIG. 9B
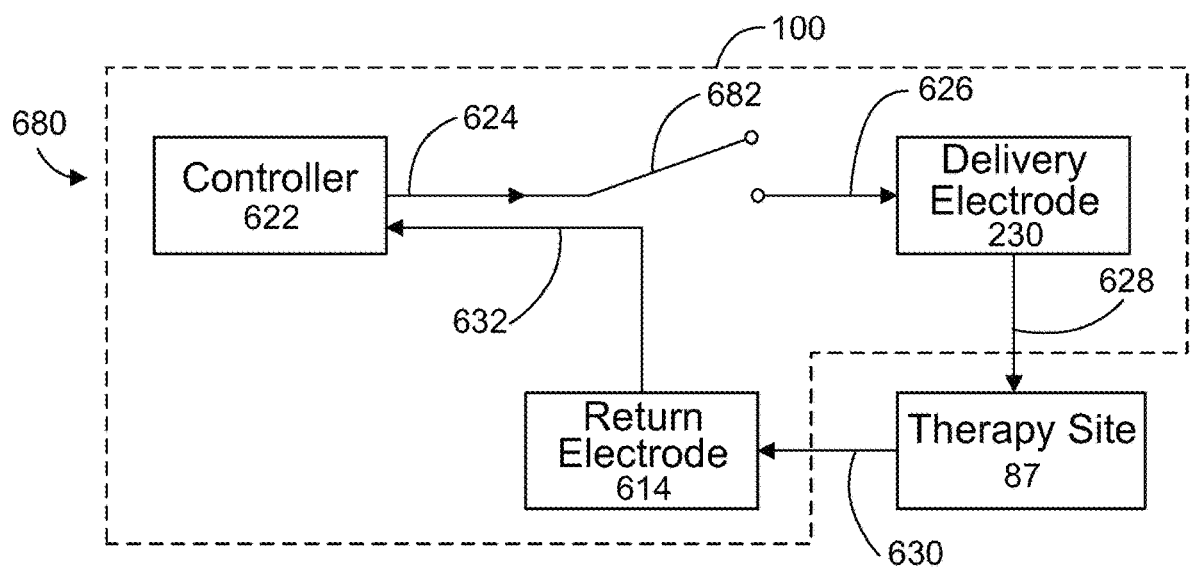
FIG. 10

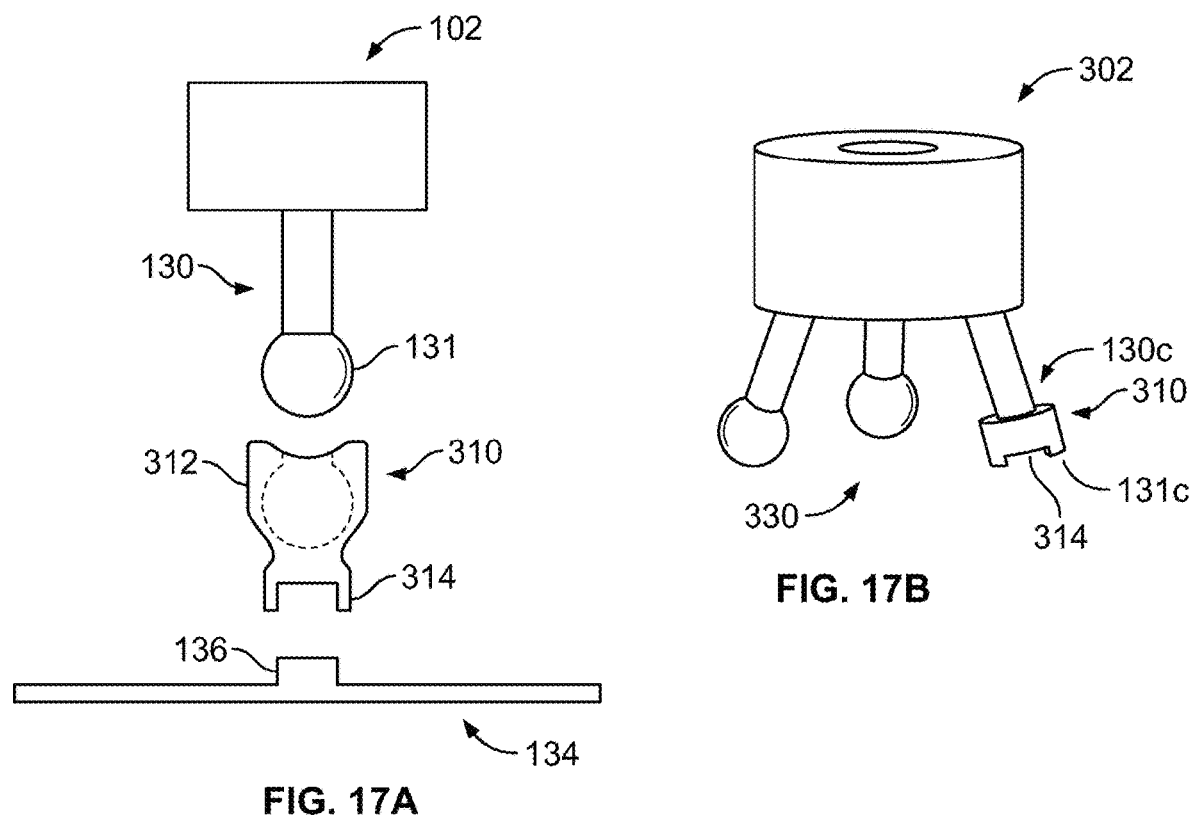
FIG. 17A
FIG. 17B
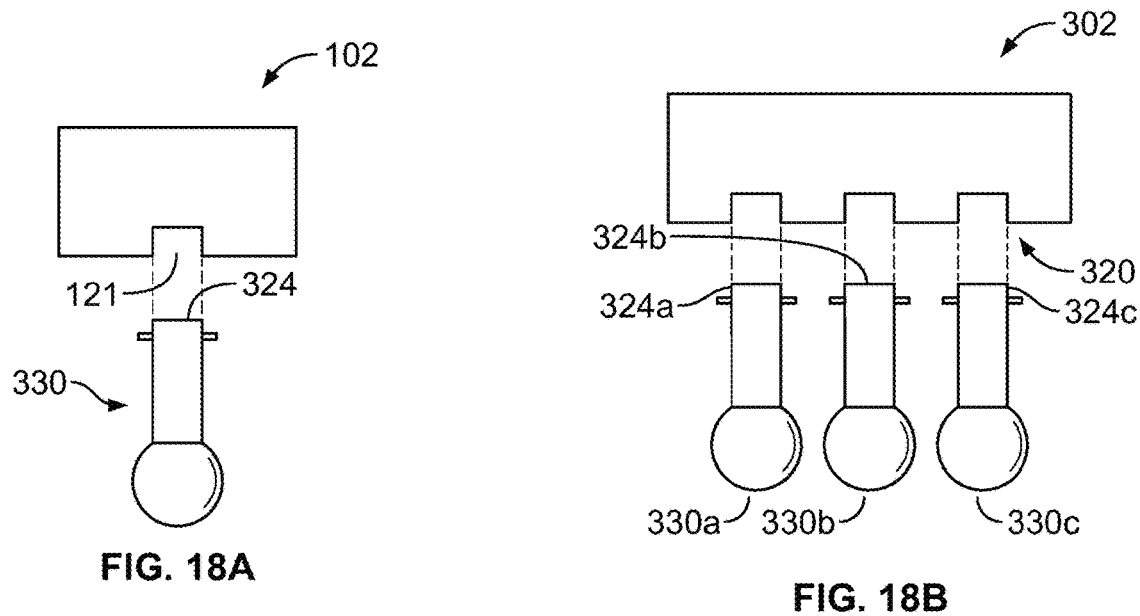
FIG. 18A
FIG. 18B

DEVICES, SYSTEMS AND METHODS FOR TREATING PAIN WITH ELECTRICAL STIMULATION

CROSS-REFERENCE TO RELATED APPLICATIONS

This application is a continuation of U.S. application Ser. No. 15/681,177, filed Aug. 18, 2017, which is a continuation of U.S. application Ser. No. 14/744,335, filed Jun. 19, 2015 and issued as U.S. Pat. No. 9,737,709 on Aug. 22, 2017, which is a continuation of U.S. application Ser. No. 13/570,004, filed Aug. 8, 2012 and issued Jun. 23, 2015 as U.S. Pat. No. 9,061,148, which claims the benefit of priority under 35 U.S.C. § 119(e) to U.S. Prov. App. No. 61/538,015, filed Sep. 22, 2011, and U.S. Prov. App. No. 61/658,756, filed Jun. 12, 2012. The disclosures of all of the above-referenced prior applications, publications, and patents are considered part of the disclosure of this application, and are incorporated by reference herein in their entirety.

BACKGROUND

Many people who go to the doctor for the treatment of headaches are experiencing migraines, especially those with a history of minor neck injury. In the United States, it is estimated that over 20 million people suffer from migraines, which approximates the number of diabetics and asthmatic patients combined. Migraines occur in over 15% of women and over 5% of men. It has been estimated that direct and indirect costs of migraines in the United States exceeds $10B per year.

The occipital nerves tend to be an important part of the headache circuit that occasionally causes migraines. The occipital nerves are made up of a convergence of fibers from the first, second, and third cervical spinal nerves. These fibers form two sets of greater and lesser occipital nerves which loop outwards to control the muscles and sensation at the base of the skull and the scalp. These nerves run approximately one-half inch under the surface of the skin of a patient's head, on the upper neck and scalp. FIG. 1A is a side view of a patient's head 80 with paths 82 extending along the surface to depict the proximate locations under which the occipital nerves and branches 82*a-c* extend. FIG. 1B is a rear view of the patient's head 80 with the external occipital protuberance 92 resected and lifted on the right side 94. Various occipital nerve paths 90 are shown, including the greater occipital nerve path 90*a* and the lesser occipital nerve path 90*b*.

A wide variety of medications are used to treat migraines, including long-activating preventative medications such as beta blockers and episodic migraine-reversers, such as tryptophan pain medications. In some cases, narcotics are used. However, many patients with migraines do not get satisfactory relief with medications. Some have tried the use of botulinum toxin (Botox) which may help relax the surrounding musculature and improve migraine symptoms in some patients. However, Botox and other medications are accompanied by a number of side effects that can be unpleasant to the patient.

In extreme cases, patients with intractable migraines historically have undergone surgical removal of occipital nerves. While this procedure has been known to provide transient relief (approximately 4-6 months), the headaches usually return in a more severe form that is unresponsive to other treatments.

More recent technological developments have included implantable occipital nerve stimulators. However, implantable nerve stimulators are complex, difficult to implement, and require surgical installation. Moreover, some existing topical stimulation systems do not provide sufficient control of the electrical current delivery, as stimulation current or voltage can vary depending on the pressure of the electrode applied to the skin. As a consequence, uneven and, in some cases, harmful stimulation can be applied.

Alternative systems and methods could be beneficial for the treatment of migraines.

SUMMARY

Disclosed herein are devices, systems and methods for non-invasive treatment of migraine headaches and other pain using electrical stimulation. In certain aspects, a hand-held, non-invasive system is configured to transmit electrical stimulation through a patient's skin to a nerve beneath the skin. In some embodiments, the system is structured as a hand-held device, that is self-applied by the patient pressing the device by against the back of the neck in the general vicinity of the occipital nerves or against other areas in need of pain relief.

In certain aspects, the system includes a housing with a controller having a signal generator. A conductive surface in electrical communication with a first signal line of the signal generator is coupled to an exterior surface of the housing, and a repositionable electrode is disposed with respect to the housing to provide improved control of the stimulation signal, for example, to modulate the pressure of the electrode at the skin, thereby providing a more even delivery of current (or voltage) for the stimulation signal. The applied pressure between the electrode and the skin can affect the contact area between the electrode and the skin, and in turn, the impedance of the interface and resulting stimulation signal. In certain approaches, the system delivers an electrical stimulation signal only when sufficient or appropriate pressure is applied to the electrode at the patient's skin. In certain embodiments, a gating switch is used to couple and decouple the electrode to a second signal line of the signal generator. For example, closing the gating switch electrically couples the electrode and the second signal line, and opening the gating switch decouples the electrode and the second signal line. In certain approaches, the gating switch is open when the electrode is in a first position with respect to the housing and the gating switch is closed when the electrode is in a second position with respect to the housing. The gating switch may include a contact pad such that the electrode is spaced away from the contact pad when in the first position and the electrode is in electrical communication with the contact pad when in the second position.

In certain implementations, the device includes a chamber configured for holding a gel, such as a conductive gel. In certain approaches, the chamber is removable from the housing. Additionally or alternatively, the chamber may be fixedly coupled to the housing. The chamber includes an electrically conductive element. In some embodiments, the electrode is in fluid communication with the chamber. In some such implementations, the housing includes a socket with a lip and a collar, with the electrode positioned within the socket between the lip and the collar. The electrode may be a rollerball electrode. In certain approaches, the rollerball electrode is located at a first end of the housing. A plurality of electrodes is provided in certain embodiments.

In certain embodiments, the electrode has an axis and the electrode is repositionable along the axis. The device may include a compression spring coupled to the electrode, such that the compression spring is compressed when the electrode is repositioned along the axis to the second position. The electrode may comprise a shaft and a tip. The tip may be a ball tip.

In certain implementations, a conductive surface is coupled to a distal portion of the housing. The conductive surface may comprise a plurality of conductive surfaces. In certain approaches, the conductive surface includes an inner portion and an outer portion. The inner portion and outer portion are electrically and physically coupled, and the outer portion is formed from an electrically conductive gel. The inner portion may be formed from an electrically conductive metal.

In another aspect, systems are configured to transmit electrical stimulation through a patient's skin to a nerve beneath the skin, which includes a housing with a controller having a signal generator, and a conductive surface in electrical communication with a first signal line of the signal generator, which is coupled to an exterior surface of the housing. An electrode in electrical communication with a second signal line of the signal generator extends from the housing. In certain embodiments, the system is configured as a hand-held device, and the patient can self-apply the device to apply electrical stimulation to the neck, occipital nerve, or other areas in need of pain relief.

In certain implementations, the conductive surface is metal. A plurality of conductive surfaces is provided in some embodiments. In certain implementations, the conductive surface is part of the stimulation circuit, functioning as part of the return electrical path when contacted by human skin. Thus, when the user grasps the one or more conductive surfaces, the circuit is completed, thereby triggering generation of stimulation current by the signal generator.

In certain embodiments, the electrode comprises a shaft and a tip. The tip may be configured to be rounded or a ball tip. The shaft may be configured to be substantially rigid. A plurality of electrodes is provided in certain embodiments. The electrodes extend from the housing and are in electrical communication with the signal generator via a signal line. In certain implementations, the inter-electrode spacing is between approximately 1 millimeter (mm) and approximately 10 mm. In certain implementations, a gel is used with the electrode to provide a stable, conductive interface between the electrode and the skin. The gel may be coupled directly to the tip of the electrode. In certain implementations, the gel is composed of a silicone or a hydrogel. In certain approaches, the gel includes a therapeutic agent.

In certain implementations, the electrode is coupled to a gating switch which opens and closes the electrical communication between the electrode and the signal generator. Closing the gating switch electrically couples the electrode and to the signal generator, and opening the gating switch decouples the electrode and the signal generator. The electrode may be repositionable along a central axis such that when in a first position, the switch is open and when in a second position, the switch is closed.

The device includes a controller for delivering electrical stimulation therapy. The controller includes a signal generator. In certain embodiments, the controller includes a programmable processor. A power source, such as a battery, is also provided. A finger-activated switch is provided, being disposed along the housing to adjust the parameters of the electrical stimulation, such as amplitude and frequency, or to turn the device on and off. In certain implementations, the device is configured to be turned off while delivering electrical stimulation.

In certain implementation, a housing of the device includes a chamber for retaining a conductive gel. In certain approaches, the chamber is removable from the housing. Additionally or alternatively, the chamber may be fixedly coupled to the housing. The chamber includes an electrically conductive element. The chamber may include an aperture configured to allow air to enter the chamber when gel is removed from the chamber. In certain approaches, the aperture includes a scrim. The scrim may be permeable to air, but impermeable to gel. In some embodiments, the electrode is in fluid communication with the chamber. In some such implementations, the housing includes a socket with a lip and a collar, with the electrode positioned within the socket between the lip and the collar. The electrode may be a rollerball.

In another aspect, systems and methods are provided for non-invasive treatment of migraine headaches and other pain using electrical stimulation with a repositionable electrode. In general, the technology includes a housing with a controller having a signal generator. A conductive surface in electrical communication with a first signal line of the signal generator is coupled to an exterior surface of the housing. A contact pad is provided within the housing, wherein the contact pad is in electrical communication with a second signal line of the signal generator. The electrode is configured to translate within the housing. When the electrode is in a first position, it is spaced away from the contact pad. When the electrode is in a second position, it is in electrical communication with the contact pad, and thereby in communication with the signal generator for delivery of electrical stimulation therapy. For example, the electrode may be repositionable along a central axis of the electrode. In use, the electrode is translated to the second position by contacting the skin of the patient and applying sufficient pressure, at which point electrical stimulation therapy is delivered. In certain embodiments, a plurality of contact pads are provided.

The device may include additional structures and features for effective delivery of electrical stimulation therapy. For example, the electrodes may also include a rigid shaft and a ball tip, and, in certain implementations, have a conductive gel surface at the tip. In certain embodiments, a compression spring is provided that is coupled to the electrode to regulate the pressure needed to reposition the electrode to the second position. In certain embodiments, a plurality of repositionable electrodes are provided. The plurality of electrodes may be concentric electrodes.

In another aspect, systems are configured to transmit electrical stimulation through a patient's skin to a nerve beneath the skin, which includes a housing with a controller having a signal generator, a first contact pad in electrical communication with a first signal line of the signal generator, a first electrode extending from the housing and in electrical communication with the first contact pad, a second contact pad in electrical communication with a second signal line of the signal generator, and a second electrode extending from the housing and in electrical communication with the second contact pad.

In certain implementations, the first electrode is axially repositionable such that the first electrode is spaced away from the first contact pad when in a first position and is in electrical communication with the first contact pad when in a second position. The system may include a first compression spring coupled to the first electrode, such that the first spring is compressed when the first electrode is in the second position. For example, the first electrode may actuate the first contact pad when the first electrode is repositioned to the second position. In certain approaches, the second electrode is axially repositionable such that the second electrode is spaced away from the second contact pad when in a third position and is in electrical communication with the second contact pad when in a fourth position. In certain embodiments, the system includes a second compression spring coupled to the second electrode such that the second spring is compressed when the second electrode is in the fourth position. For example, the second electrode may actuate the second contact pad when the second electrode is repositioned to the fourth position.

In certain embodiments, the first electrode has a shaft and the second electrode has a shaft, and the shaft of the first electrode and shaft of the second electrode are substantially parallel. For example, the first electrode and second electrode may have an inter-electrode spacing of between approximately 1 mm and approximately 10 mm. In certain approaches, the first electrode at least partially surrounds the second electrode. For example, the first electrode and second electrode may be concentric. In certain embodiments, the first electrode has a tip and the second electrode has a tip, and a first conductive gel is coupled to the tip of the first electrode and a second conductive gel is coupled to the tip of the second electrode. In certain approaches, the first conductive gel and the second conductive gel are physically and electrically coupled. In certain embodiments, the first electrode is removably coupled to housing. In certain embodiments, the second electrode is removably coupled to housing.

In certain approaches, the controller includes a programmable processor. A power source, such as a battery, is also provided. In certain implementation, a housing of the device includes a chamber for retaining a conductive gel. In certain approaches, the chamber is removable from the housing. Additionally or alternatively, the chamber may be fixedly coupled to the housing. The chamber includes an electrically conductive element. The chamber may include an aperture configured to allow air to enter the chamber when gel is removed from the chamber. In certain approaches, the aperture includes a scrim. The scrim may be permeable to air, but impermeable to gel. In some embodiments, the electrode is in fluid communication with the chamber. In some such implementations, the housing includes a socket with a lip and a collar, with the electrode positioned within the socket between the lip and the collar. The electrode may be a rollerball.

In certain aspects, methods of non-invasively treating patient pain are disclosed herein. For example, methods are included that involve positioning a first electrode on skin at a location near a patient's occipital nerve or other parts of the patient, electrically coupling the first electrode to a second electrode, applying pressure to the first electrode to translate the electrode along an axis to be in electrical communication with a signal generator, and delivering current through the first electrode. The first electrode translates along an axis by applying pressure to the skin with the electrode, and thereby closes a switch to form a complete electrical circuit. In certain embodiments, the second electrode is placed on the skin of the patient and functions as a return electrode. The second electrode may also be held by the patient. Methods are further provided to adjust the current levels.

In another aspect, systems and methods are provided for transmitting electrical stimulation to a nerve with a device that can be coupled to the therapy site, such as a patient's head or neck. In general, the technology includes a controller having a signal generator, a electrode support having a first electrode and second electrode coupled to the signal generator by a first signal line, and a patch having a third electrode and fourth electrode coupled to the signal generator by a second signal line. In general, the first electrode is electrically coupled to the fourth electrode and the second electrode is electrically coupled to the third electrode. The first electrode and second electrode are electrically independent. The third electrode and fourth electrode are electrically independent. In certain approaches, the first signal line and second signal line may each comprise a plurality of signal lines.

Methods of non-invasively treating patient migraines with a plurality of electrical signals are also disclosed herein. For example, methods are included that involve positioning a first electrode, a second electrode, a third electrode, and a fourth electrode on a patient's skin at a location near the patient's occipital nerve such that the electrodes are spaced away from each other. The first and fourth electrodes form a conductive path through which a first electrical signal is delivered. Additionally, the second and third electrodes form a conductive path through which a second electrical signal is delivered simultaneously with the first electrical signal. The first and second electrodes may be coupled to a electrode support on the patient's head. The second and third electrodes may be coupled to a patch positioned on the patient's skin. In certain approaches, the first conductive path and second conductive path intersect. The interference of the first electrical signal and second electrical signal forms a beat wave. In certain implementations the first electrical signal has a frequency different from a frequency of the second electrical signal by between approximately 1 Hz and 100 Hz. In certain approaches, the first electrical signal has a frequency between approximately 3500 Hz and 4500 Hz.

Methods are also provided for identifying a therapy site. In certain approaches, methods are included that involve placing a first electrode and a second electrode in a first configuration on a patient's skin, such that the first electrode and second electrode are electrically coupled through the patient's tissue and form a conductive path that is approximately longitudinally along the patient's nerve. These methods also include delivering a first electrical signal while the first electrode and second electrode are in the first position, and identifying an effect of the first electrical signal. The method may further include placing the first electrode and second electrode in a second position, such that the first electrode and second electrode are placed on different sides of a longitudinal axis of the patient's nerve, delivering a second electrical signal while the first electrode and second electrode are in the second position, and identifying an effect of the second electrical signal. In certain embodiments, the first and second electrodes are spaced between approximately 1 mm and approximately 10 mm apart in the first position. The method may involve identifying a therapy site after delivering the first electrical signal and second electrical signal, and then marking the therapy site.

In certain aspects, a hand-held, non-invasive device is configured to transmit electrical stimulation through a patient's skin to a nerve beneath the skin, which includes a housing having an exterior surface, a controller having a signal generator disposed within the housing, a conductive surface coupled to the exterior surface of the housing, and a repositionable electrode disposed with respect to the housing. The signal generator has a first signal line and a second signal line. The conductive surface is in electrical communication with the first signal line of the signal generator. The electrode is electrically discontinuous from the second signal line when in a first position and wherein the electrode is in electrical communication with the second signal line when in a second position. The device may include a contact pad within the housing and in electrical communication with the second signal line of the signal generator such that the electrode is spaced away from the contact pad when in the first position and the electrode is in electrical communication with the contact pad when in the second position.

The electrode may have an axis and be repositionable along the axis. The device may include a compression spring coupled to the electrode, such that the spring is compressed when the electrode is repositioned along the axis to the second position. For example, the electrode actuates the contact pad when the electrode is repositioned to the second position. In certain approaches, the electrode comprises a shaft and a tip. The tip may be a ball tip. In certain embodiments, the electrode comprises a plurality of electrodes disposed at a first end of the housing.

In certain aspects, a hand-held, non-invasive device is configured to transmit electrical stimulation through a patient's skin to a nerve beneath the skin, which includes a housing, a chamber within the housing configured for holding a gel, a controller having a signal generator disposed within the housing, a return electrode, and a repositionable rollerball electrode disposed with respect to the housing and in fluid communication with the chamber. The signal generator has a first signal line and a second signal line. The return electrode is in electrical communication with the first signal line of the signal generator. The electrode is electrically discontinuous from the controller when in a first position and the electrode is in electrical communication with the second signal line when in a second position.

In certain approaches, the chamber is removable from the housing. Additionally or alternatively, the chamber may be fixedly coupled to the housing. The chamber includes an electrically conductive element. The chamber may include an aperture configured to allow air to enter the chamber when gel is removed from the chamber. In certain approaches, the aperture includes a scrim. The scrim may be permeable to air, but impermeable to gel. In some embodiments, the electrode is in fluid communication with the chamber. In some such implementations, the housing includes a socket with a lip and a collar, with the electrode positioned within the socket between the lip and the collar.

In certain aspects, a hand-held, non-invasive device is configured to transmit electrical stimulation through a patient's skin to a nerve beneath the skin, which includes a housing having an exterior surface, a chamber within the housing configured for holding a gel, a controller having a signal generator disposed within the housing, a conductive surface coupled to the exterior surface of the housing, and a rollerball electrode disposed with respect to the housing and in fluid communication with the chamber. The signal generator has a first signal line and a second signal line. The conductive surface is in electrical communication with the first signal line of the signal generator. The housing is substantially cylindrical. In certain embodiments, the conductive surface is coupled to a distal portion of the housing. The conductive surface may comprise a plurality of conductive surfaces. The conductive surface includes an inner portion and an outer portion, such that the inner portion and outer portion are electrically and physically coupled. The outer portion is formed from a conductive gel. The inner portion is formed from a conductive metal. The device may include a gating switch coupled to the electrode and the second signal line, such that closing the gating switch electrically couples the electrode and the second signal line, and opening the gating switch decouples the electrode and the second signal line.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Further features, aspects, and advantages of various embodiments are described in detail below with reference to the accompanying drawings.

BRIEF DESCRIPTION OF THE DRAWINGS

The accompanying drawings, which are incorporated in and form a part of the specification, illustrate certain implementations and, together with the description, serve to explain various examples of the devices, systems and methods disclosed herein.

FIGS. 9A-9B are side views of an electrical stimulation device with a depressible electrode.

FIG. 10 is a block diagram of an illustrative therapeutic current path associated with an electrical stimulation device, such as the device of FIGS. 9A-9B.

FIG. 17A is a side view of an illustrative housing connector with an adapter for receiving an electrode or other stimulation delivery component.

FIG. 17B is a perspective view of an illustrative housing connector with an adapter for receiving an electrode or other stimulation delivery component.

FIGS. 18A-18B are cross-sectional views of illustrative housing connectors with releasable electrodes.

DETAILED DESCRIPTION

Disclosed herein are devices, systems and methods for non-invasive treatment of migraine headaches and other pain using electrical stimulation. In general, the technology includes a non-invasive device configured to transmit electrical stimulation through a patient's skin to a nerve beneath the skin. The device includes a housing with a controller having a signal generator. Examples of devices that may be used to implement the controller include, but are not limited to, microprocessors, microcontrollers, integrated circuits (ICs), central processing units (CPUs), programmable logic devices, field programmable gate arrays, and digital signal processing (DSP) devices. A conductive surface in electrical communication with a first signal line of the signal generator is coupled to an exterior surface of the housing. An electrode in electrical communication with a second signal line of the signal generator extends from the housing. The patient can self-apply this hand-held device by pressing it against the back of the neck in the general vicinity of the occipital nerves or by applying it to other areas in need of pain relief.

Figure 2:
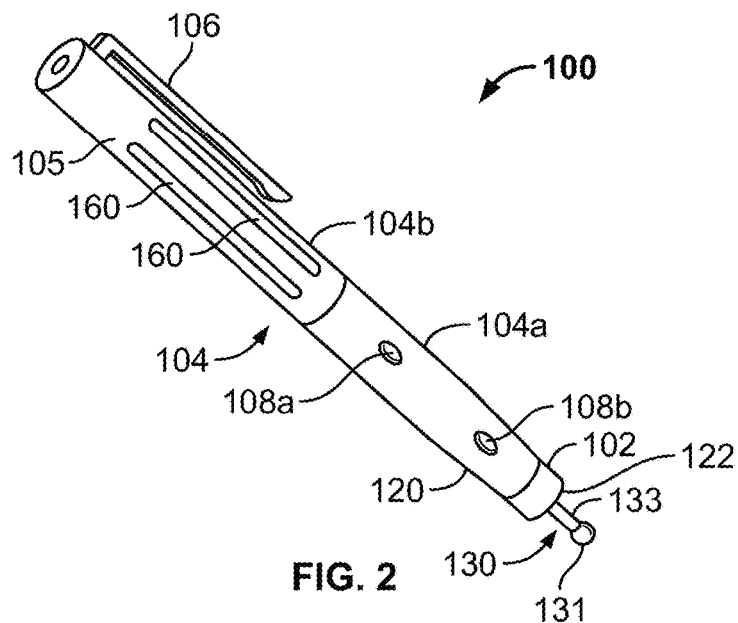
FIG. 2 is a perspective view of an illustrative hand-held, non-invasive electrical stimulation device for the treatment of pain.

FIG. 2 is a perspective view of a hand-held nerve stimulation device 100 that may be used to provide electrical stimulation to the surface of a patient, such as the back of the patient's head for stimulating the occipital nerves. The device 100 of FIG. 2 includes a housing 104 in the form of a rigid shaft that houses inner electronics, such as a power supply and signal generator (not shown). The housing 104 is shaped like a pen. Alternative implementations include other shapes and designs of the housing 104 that are rigid enough to allow adequate pressure to be applied to the back of the patient's head or to allow the device 100 to be placed proximal to the therapy site with sufficient accuracy.

The housing 104 includes a distal portion 104a and a proximal portion 104b. The housing 104 may be substantially cylindrical. For example, the housing 104 may be shaped similar to a pen so that it can be held easily in the hand of a user. The distal portion 104a is formed of a rigid material, preferably plastic, and receives the buttons 108a and 108b. An operator uses his or her finger to actuate and control the buttons 108a and 108b to turn the device on and off, increase and decrease the levels of stimulation, and adjust other therapy settings (e.g., waveform shape, frequency). In certain embodiments, one or both of the buttons 108a and 108b include potentiometers. When the potentiometer is adjusted, the intensity of the electrical stimulation signal provided by the device 100 is increased or decreased accordingly.

The device 100 also includes a connector 102 which connects to the distal end 120 of the housing 104 by screw threads (not shown). In alternative implementations, the connector 102 may be connected to the distal end of the housing 104 by a clip, a snap fitting, glue, or another connection mechanism, or may be integral with the housing 104. The connector 102 includes an electrode 130 for delivering electrical stimulation to a patient. The electrode 130 includes a shaft 133 that extends from the housing 104 and a tip 131 that contacts the patient. In certain implementations, the tip 131 has a rounded or ball-like surface. In preferred implementations, the tip 131 is non-tissue penetrating. In certain approaches, the tip 131 has a diameter between approximately 0.5 and approximately 5 mm, but may have any appropriate size for effective electrical stimulation. The electrode 130 is in electrical communication with a signal line of a signal generator located within the housing 104, as described below. In certain implementations, the device 100 also includes a clip 106 that fastens the device 100 to a secure place, such as the operator's pocket, a notebook, or a case.

The device 100 includes one or more conductive surfaces 160 disposed along the outer surface 105 of the housing 104. The conductive surfaces 160 function as return electrodes for the current delivered by the device 100. The conductive surfaces 160 provide simplicity and convenience in use because the user can simply hold the device 100 to use it, and need not place a separate return electrode on the body. The conductive surfaces 160 may be made of a metal or a conductive polymer. In preferred implementations, the conductive surfaces 160 are made of chrome or silver-plated aluminum, but the conductive surfaces 160 may be made of any suitable conductive material. The conductive surfaces 160 may be disposed along any part of the housing 104, including the distal portion 104a and the proximal portion 104b. In certain implementations, the conductive surfaces 160 cover the entire external surface of the housing 104. When self-applied by a patient, the patient grasps the device 100, thereby placing the tissue of the patient's hand in contact with the conductive surfaces 160. When the patient then positions the device 100 such that the electrode 130 is in contact with a target area of the patient's tissue, current flows from a signal generator in the device 100, through the electrode 130, out of the tip 131, through the target area on the patient, through the patient's arm, and through the conductive surfaces 160, thereby returning to the device 100. This and other current flow paths are discussed in additional detail below. In certain implementations, the conductive surfaces 160 include an outer, conductive, gel layer (not shown) for ease and comfort in gripping the device 100 and improving conductivity between an operator's hand and the device 100. For example, the gel layer may be a firm gel which is able to retain its shape.

Figure 3:
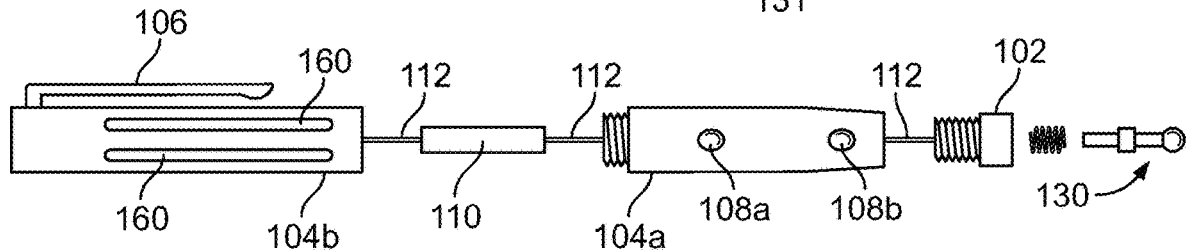
FIG. 3 is an exploded view of certain components of the device of FIG. 2.

FIG. 3 is an exploded view of certain components of the device 100 of FIG. 2. The proximal portion 104b of the housing 104 forms a cap that contains a mounting plate 110. The mounting plate 110 mounts the internal signal pulse generator, power supply, and other electronic components (such as processing circuitry for controlling the waveforms and other operation of the device, not shown) and seats the buttons 108a and 108b (or their interface to the controller or signal generator). In some implementations, the mounting plate 110 is a printed circuit board (PCB). In certain implementations, wires 112 are used to connect the electronics on the mounting plate 110 to the buttons 108a and 108b and to the connector 102. In alternative implementations, the electronic components are connected directly to the mounting plate 110 or to each other.

Figure 4:
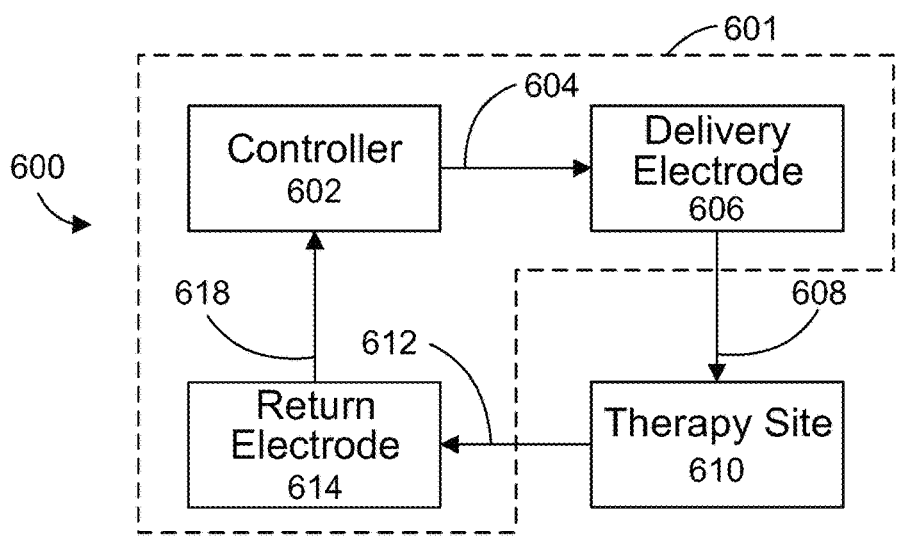
FIG. 4 is a block diagram of an illustrative therapeutic current path associated with an electrical stimulation device, such as the device of FIG. 2.

FIG. 4 is a block diagram of an illustrative therapeutic current path associated with an electrical stimulation device, such as the device of FIG. 2, for delivering electrical stimulation therapy to a patient therapy site to alleviate pain caused by migraines. The current path 600 of FIG. 4 includes an electrical stimulation device 601 (which may be similar to the device 100 of FIG. 2) that includes a controller 602 with a first signal line 604 that connects the controller 602 to a delivery electrode 606. The electrical stimulation device 601 also includes a return electrode 614 and a second signal line 618 that connects the return electrode 614 to the controller 602. The controller 602 may include a power source, a processing device, a signal generator, and other electronic components for delivering electrical stimulation therapy to the therapy site 610 via the delivery electrode 606. The delivery electrode 606 may include a conductive surface extending from the electrical stimulation device 601, such as electrode 130 of FIG. 2.

During use, the controller 602 generates current that flows from the controller 602 through the first signal line 604 to the delivery electrode 606. The current then flows from the delivery electrode 606 through a conductive path 608 to the therapy site 610. The conductive path 608 may include tissue, such as skin, and other conductive materials, such as conductive gels. The therapy site 610 may be nerve tissue, such as the occipital nerve or other nerve or muscle tissue. The current flows through the therapy site 610 and returns through a conductive path 612 (which may also include tissue such as skin) to the return electrode 614. The current then flows from the return electrode 614 through the signal line 618 to the controller 602, forming a complete closed circuit.

Figure 5A:
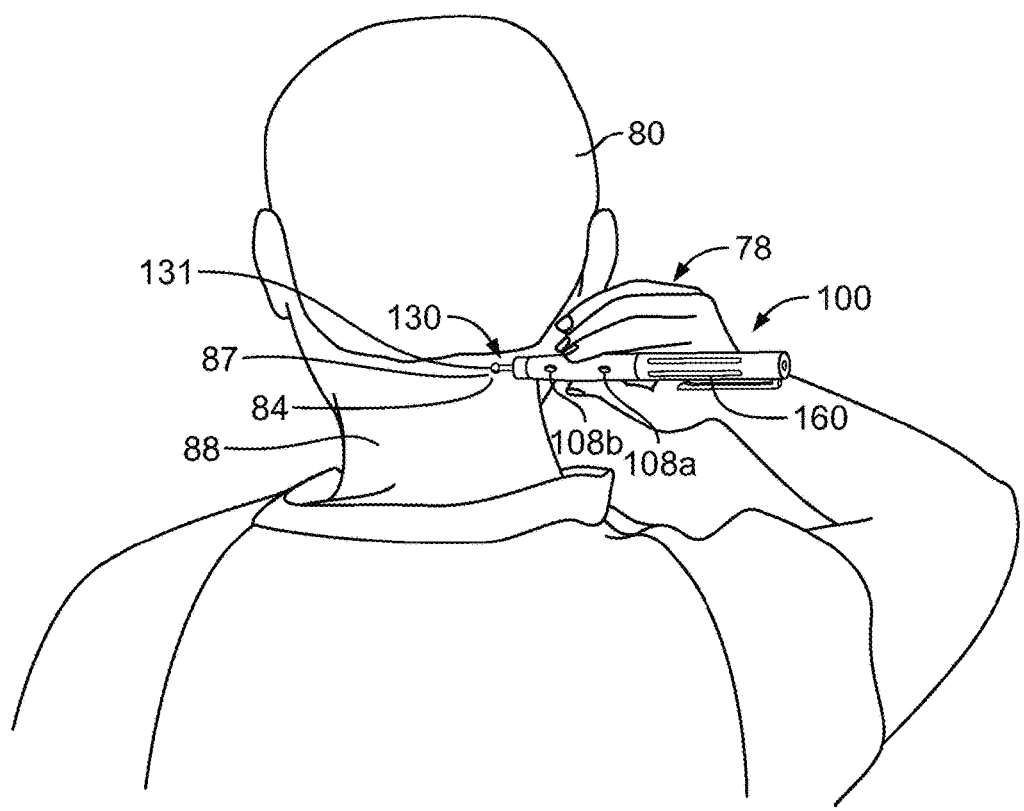
FIG. 5A is a perspective view of an illustrative embodiment of the application of the electrical stimulation device of FIG. 2 to the back of a patient's head for the stimulation of the occipital nerve for relief of migraine headaches.

FIG. 5A is a perspective view of the electrical stimulation device of FIG. 2 as applied to the back of a patient's head 80 for the stimulation of the occipital nerve for relief of migraine headaches. In practice, a conductive gel may be placed in the hair or on the skin over the occipital nerve location. Conductive gel typically reduces skin irritation and provides improved electrical coupling by increasing the conductivity of the electrode-skin interface and filling contact voids between the electrode and skin to provide more uniform electrical contact. In certain approaches, a conductive gel is a jelly-like material. A conductive gel may be a spreadable. For example, the gel may be a cream or a liquid. In certain approaches, the gel is a colloid. In certain approaches, the gel is capable of being reshaped. In certain approaches, the gel may be a solid or able to retain a specific shape. A conductive gel may be in the form of a patch. In use, the tip 131 of the electrode 130 of the device 100 is pressed against the skin 84 over a therapy site 87, and the amplitude of the stimulation is increased to a comfortable level that may be maintained until a treatment regimen is complete. In certain approaches, the device 100 delivers conductive gel to the skin 84 when pressed against the skin 84, as described in further detail below in relation to FIG. 29 and FIG. 30. The therapy site 87 may overlie nerve tissue such as the occipital nerve (e.g., occipital nerve 90), or other nerve or muscle tissue.

The device 100 is actuated and adjusted to provide appropriate stimulation levels by increasing and decreasing the current via the buttons 108a and 108b, for example. In certain cases, the stimulation parameters (e.g., waveform shape, amplitude, and frequency) are prescribed by a physician or other caregiver. In certain cases, the stimulation is applied for a predetermined period of time. In certain cases, the treatment regimen is applied for a predetermined time, but continued until the patient experiences a reduction in pain. The stimulation current actually felt by the patient will vary according to several factors, including the amplitude of current delivered and the electrical impedance of the skin, muscle, and other tissue between the electrodes 130 and the target delivery site.

In some implementations, the device 100 generates and delivers a current only when sufficient pressure is applied to the electrode 130 at the skin 84. For example, the electrode 130 may be coupled to a pressure-sensitive gating switch, which electrically couples the electrode 130 to the signal generator of the device 100 when sufficient pressure is applied, and decouples the electrode 130 and the signal generator otherwise.

In preferred implementations, the tip 131 is a rounded, ball-like surface that may be comfortably pressed against the skin of the patient. A ball-like tip 131 also increases the surface area of the contact interface between the skin 84 and the electrode 130 for more controlled current flow to the therapy site 87. In particular, the caregiver or the patient can apply the device 100 at varying levels of pressure to vary the contact area between the tip 131 and the skin 84, which may change the impedance between the electrode 130 and the therapy site 87 and thereby change the amount of current delivered to the therapy site 87. For example, in a constant voltage implementation, the device 100 is pressed against the patient's skin at a first level of pressure, such that a portion of the surface area of the tip 131 contacts the skin 84. The pressure is subsequently increased to press the tip 131 into the skin 84, indenting it somewhat and thereby increasing the surface area of the skin 84 that contacts the electrode 130. This increased contact area between the tip 131 and the patient reduces the electrical impedance between the electrode 100 and the therapy site 87, and inversely and proportionally increases the stimulation current provided to the patient without otherwise adjusting parameters of the stimulation (e.g., using the buttons 108a and 108b). In constant current modes of use, this adjustment changes the power consumed by the device 100.

Moreover, increasing the pressure of the contact between the tip 131 and the skin 84 compresses the tissue below the skin 84, thereby moving the tip 131 closer to the therapy site (e.g., a target nerve or other region) and reducing the electrical impedance of intervening muscle and other tissue. This may provide more energy to the therapy site and potentially more relief to the patient. For example, pressing the tip 131 into the skin 84 can improve stimulation delivered directly to the occipital nerve 90, which is located between approximately 3 mm and 17 mm below the skin 84. In this way, the operator can not only adjust the amount of energy generated by the device, but can adjust the amount of that energy that actually reaches the therapy site, and therefore can more precisely adjust the treatment applied.

A small tip 131 of the device 100 allows a larger current density at the skin contact site as compared to standard electrodes. The larger current density can permit a more precise stimulation delivery by allowing the current to reach the fine motor points more easily. In particular, a large current density more easily overcomes the resistance by muscle and other tissue between the tip 131 of the device 100 and the therapy site. The current that reaches the therapy site would therefore be distributed over a smaller area and potentially more beneficial to the patient.

When a gel is used at the skin surface, the current density of the stimulation therapy is also a function of the diameter, thickness, and conductivity of the gel through which the stimulation is directed. In certain implementations, the type of gel used and the geometry of its application are adjusted to more effectively provide stimulation therapy, as described below. For example, the electrode may be provided with an integral conductive gel coating, or the conductivity of the gel may be tuned to selectively direct current through one or more paths.

In certain implementations, the tip 131 of the electrode 130 provides for sufficient current density so that electrical stimulation can be applied in therapeutic settings where the patient is using medicated cream or other ointments that make it difficult to use standard electrical stimulation devices. For example, BENGAY® and other medicated pastes are not typically used with standard wide-area electrodes (such as standard TENS electrodes) for treating orthopedic pain, because the hydrogels commonly used with such electrodes (such as those containing a glycerin base with electrolytes) do not adhere well to such pastes. A small tip 131 alleviates the need to use a glycerin or other hydrogel to achieve sufficient current delivery, which can allow the device 100 to be applied with medicated creams and pastes.

The device 100 can therefore be used to deliver electrical stimulation therapy in place of devices that use large electrodes with hydrogel interfaces. The device 100 can also be used to treat other anatomical areas besides the occipital nerve, including the back of a patient's knee or other anatomical areas. In alternative implementations, the tip 131 of the electrode 130 may include a needle or other sharp tip that can penetrate the tissue of the patient to provide improved acupuncture therapy or related therapies. In certain implementations, the electrode 130 is removable from the device 100, and may be interchanged with other electrode structures including, but not limited to, needle electrodes and pad electrodes.

The device 100 may also include a marking element, such as a pen or marker tip. A marking element may be useful to mark a therapy site, such as the therapy site 87. In use, a physician, therapist, or other care provider, may use the device 100 to stimulate nerve or muscle tissue and elicit a response. For example, the patient may experience reduced pain or, in the case of stimulating muscle tissue or the nerve connected to muscle tissue, the stimulation current may cause a muscle twitch. In certain embodiments, the device 100 may be used by a surgeon (e.g., a hand or foot surgeon) to identify and mark a motor point. For example, the motor point may be the target of a surgical procedure or may be identified as a therapy site for nerve or muscle electrical stimulation treatment. The care provider can then use the marking element to circle a therapy site, trace a nerve, or otherwise provide instructive marks for improved therapy. In certain approaches, the marking element is attachable to the device 100. For example, the marking element may be an attachable cartridge. The cartridge may slide over and clamp onto the distal end 120 of the housing 104. In certain approaches, the marking element is interchangeable with the electrode 130. For example, the device 100 may function similarly to a multi-tip pen, with at least one tip being an electrode (e.g., the electrode 130), and a second tip being a marking element. The tips may be interchangeable, for example, by pushing a button or rotating the housing 104. In some implementations, the electrode 130 is removable and replaceable with a marking element.

Figure 5B:
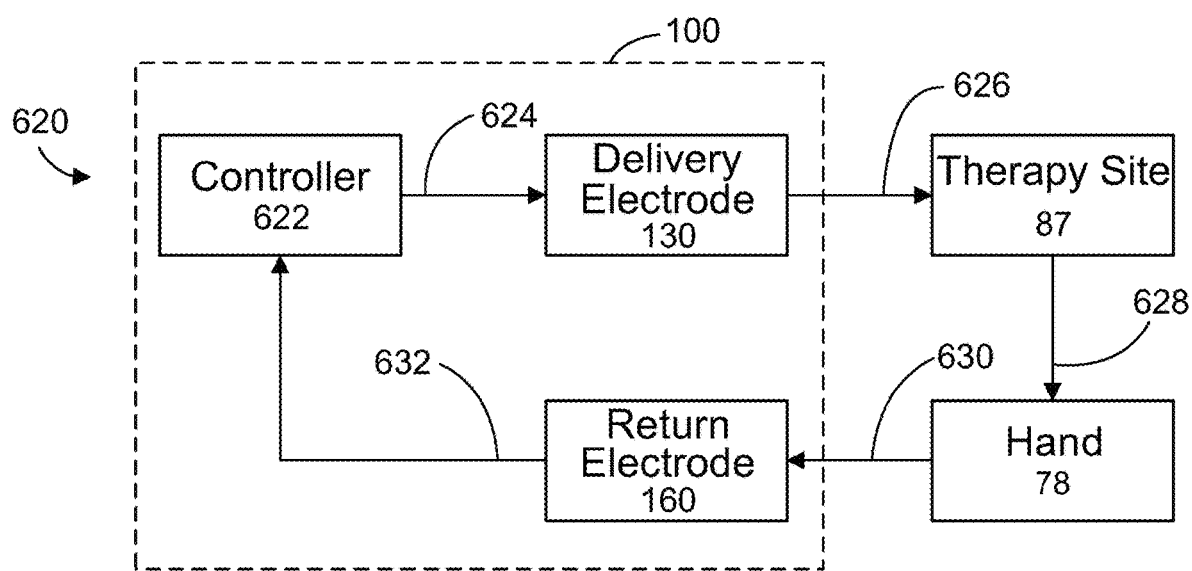
FIG. 5B is a block diagram of the therapeutic current path according to the illustrative embodiment of FIG. 5A.

As described above with reference to FIG. 4B, during use of the electrical stimulation devices described herein, a closed current path between the electrical stimulation device and the therapy site is formed. FIG. 5B is a block diagram of the therapeutic current path 620 between a controller 622 of the device 100 and the therapy site 87, according to the illustrative embodiment of FIG. 5A. The current path 620 forms a closed electrical circuit from the controller 622 through the delivery electrode 130, to the therapy site 87, through the patient's hand 78, and back through the conductive surfaces 160 to the controller 622. In particular, the controller 622 (which may include a power supply such as a battery, a signal generator, a processing device, and other electronic components) produces a current that flows from the controller 622 through the first signal line 624 to the electrode 130. The signal line 624 may include a wire or other conductive surface, such as the wire 112 depicted in FIG. 3. When the electrode 130 is pressed to the skin 84 of the patient, a conductive path 626 is formed between the electrode 130 and the therapy site 87. The conductive path may include the patient's skin, as well as intervening conductive materials such as a conductive gel. The therapy site 87 may include muscle or nerve tissue, such as the occipital nerve. In the embodiment of FIG. 5A, the stimulation current flows through the therapy site 87 to the patient's arm and hand 78 through a conductive path 628 which includes the patient's inner tissue. The patient's hand 78 touches at least one of the conductive surfaces 160 of the device 100 to form a conductive path 630. The conductive surfaces 160 function as a return electrode for the therapeutic current, and return that current to the controller 622 via a second signal line 632 (e.g., the wire 112 or another conductive element).

The devices, systems and methods disclosed herein provide an advance over existing technologies. For example, there is no need for an invasive surgery or implantation of the device 100, which eliminates surgical costs and associated risks such as infection and electrical lead wire migration. The device 100 can be produced cost-effectively. The device 100 can be used as a diagnostic tool or on a trial basis before implantation of an implantable stimulator, if desired. Because the stimulation current is applied at a relatively small location (and may be applied along the hairline), a patient's head need not be shaved and thus cosmetic hair adjustments are not needed. Moreover, treatment time can be reduced because the stimulation current can be applied directly to an appropriate therapy site. Treatments can be easily adjusted and applied at any convenient time for the patient. The device 100 can therefore be better tailored to meet certain individual needs and, in many cases, provide faster results than medication, surgery, acupuncture therapy or other currently available treatment modes.

Figure 6:
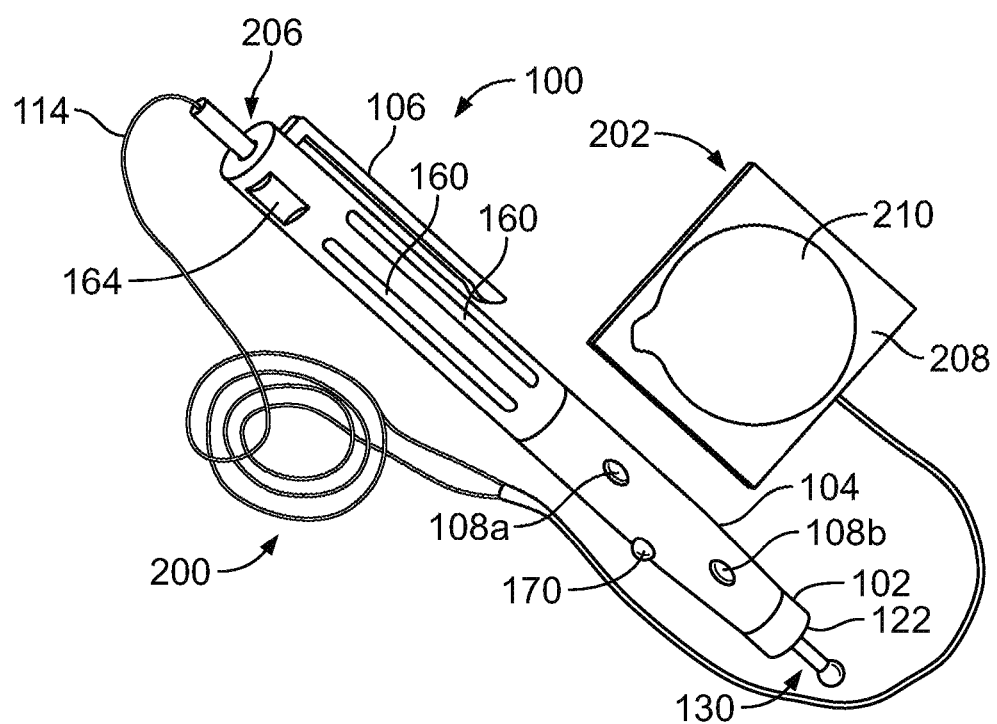
FIG. 6 is a perspective view of an electrical stimulation system including the device of FIG. 2.

FIG. 6 depicts the device 100 of FIG. 2 assembled into a non-invasive electrical stimulation system 200 for use in applying stimulation to occipital nerves or other tissue for the treatment of migraine headaches or other pain. The system 200 includes the device 100 as well as additional components that may be used in certain implementations to provide effective electrical stimulation therapy to alleviate pain. For example, the system 200 includes an extension electrode 202 connected to the device 100 by an electrical lead wire 114 at a electrode jack 206. The extension electrode 202 functions as a return path for current delivered to a therapy site by the electrode 130 and may be provided in addition to or in place of the conductive surfaces 160. When used, the extension electrode 202 is placed away from the therapy site (for example, at the base of the neck, shoulder, or arm). Because the contact area between the extension electrode 202 and the patient's tissue is greater than the area between the conductive surfaces 160 and the patient's tissue, using the extension electrode 202 as the return electrode instead of or in addition to the conductive surfaces 160 may distribute the return current over a greater contact area and thereby reduce the current density in the user's tissue. The extension electrode 202 may be used if the therapy causes discomfort at the hand when the conductive surfaces 160 are used as the only return electrodes in the current return path. In certain implementations, both the conductive surfaces 160 and the extension electrode 202 are provided and used as return electrodes. In certain implementations, a plurality of extension electrodes 202 are provided and used. In certain implementations, the extension electrode 202 is releasably attached to the device 100. The extension electrode 202 may be disposable and replaceable for improved convenience and sanitation.

The extension electrode 202 includes an electrically conductive surface 210. The conductive surface 210 may be made of metal or conductive polymer (e.g., chrome, silver-plated aluminum, silver chloride, or any suitable conductive material). The extension electrode 202 includes a backing layer 208 for handling the extension electrode 202. In certain embodiments, the backing layer 208 is peeled off when applied to the patient. For example, backing layer 208 may protect an adhesive surface for attaching the extension electrode 202 to the skin of a patient. In certain implementations, the adhesive surface is a conductive coating over the conductive surface 210. For example, the adhesive surface may include silicone, other polymers such as polyvinylpyrrolidone, polyethylene oxide, polyvinyl alcohol, polyethylene glycol, polyacrylamide, or polysaccharides, such as gum karaya.

The device 100 of the system 200 of FIG. 6 includes a status indicator 170. The status indicator 170 informs a user of the operational status of the device 100 and can come in the form of a visual, an audible, and/or a tactile indicators. Examples of suitable status indicators include a light, an LED, a liquid crystal or other type of display, a speaker, a buzzer, and a vibration motor. The status indicator 170 may be used to indicate any of a number of therapeutic or other conditions. For example, the status indicator 170 may be used to indicate whether the device 100 is ON or OFF. The status indicator 170 may be used to indicate whether the electrode 130 is applied to the skin with sufficient pressure to activate the device 100 for delivery of a stimulation current. The status indicator 170 may be used to indicate an operational mode, such as a type of therapy being provided, or a change in operational mode, such as an increase or decrease in stimulation current amplitude. For example, the device 100 may be configured so that the status indicator 170 includes one or more LEDs that emit certain colors that correspond with the amplitude of the therapy being delivered. The status indicator 170 may be used to show battery power status (e.g., full power, percentage of full power, or low on power/in need of charge), or charging status (e.g., charging or fully charged). Other types indicators are used in other possible embodiments. Speakers, buzzers, and vibration motors are particularly useful for those with certain disabilities or impairments and are also useful for communicating information to a patient when the device 100 is being used in an area that is not easily visible (e.g., on the patient's back). In certain embodiments, the status indicator 170 allows an operator to view current operating parameters, view historical user data (such as performance and use statistics), view current physiological parameters (such as muscle feedback signals, heart rate). For example, the status indicator 170 may show a selection menu for making therapy adjustments with buttons 108a and 108b. The status indicator 170 may also provide a display with instructions or progress updates when the operator downloads additional programs or firmware to the internal controller. Although only a single status indicator is shown in FIG. 6, two or more status indicators may be included with the device 100 to perform any one or more of the functions described above, or any other suitable function.

The device 100 includes a port 164, which can receive an input from one or more external sources. For example, the port 164 may be configured as a recharging port which receives an electrical connector to recharge the battery of the device 100. In certain implementations, the device 100 can be powered by an external power supply connected via port 164. In some implementations, the port 164 includes a thermistor to monitor the temperature of a battery included with the device 100 during charging to avoid overheating. In some such implementations, the charge level is indicated by the status indicator 170. In certain implementations, the physician or technician connects the device 100 to bedside equipment via a connection with the port 164 (which may be, for example, a USB port), to download data from the device 100 or upload data to the device 100. In certain embodiments, port 164 is used to download stimulation protocols or update firmware for the internal controller.

Figure 7A:
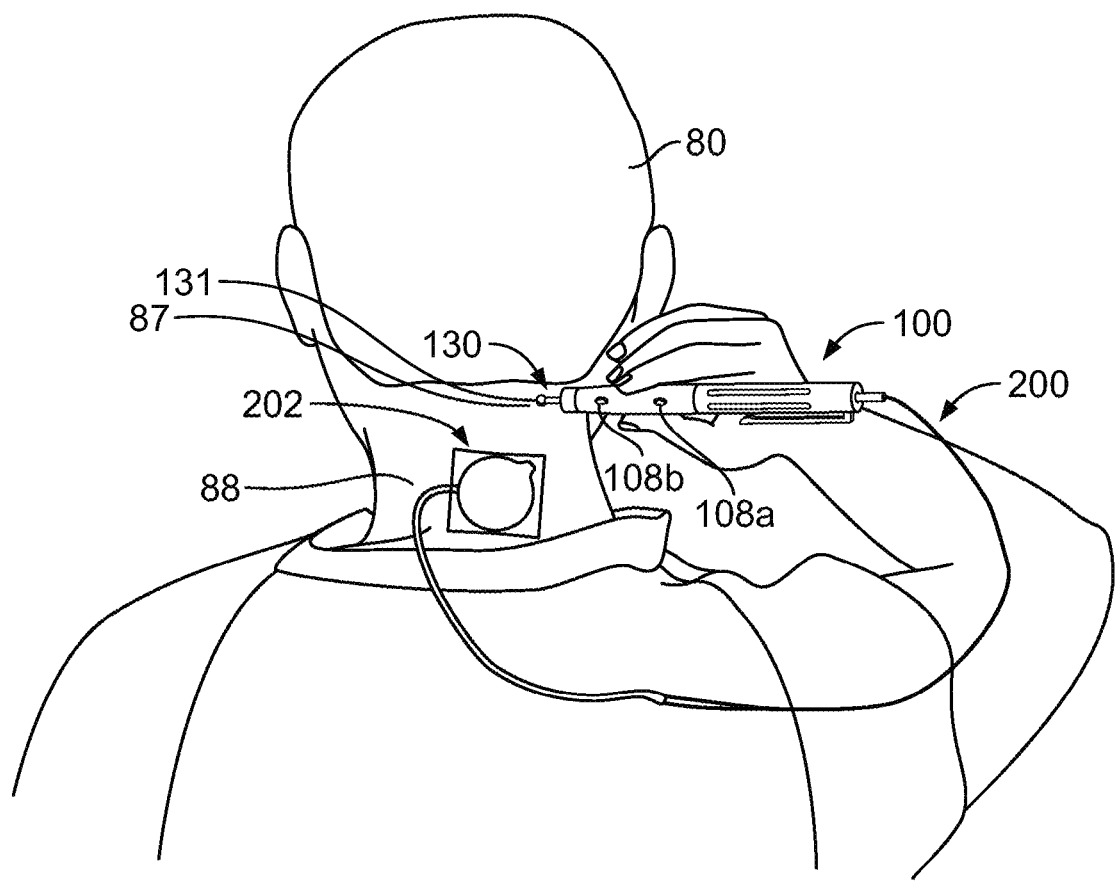
FIG. 7A is a perspective view of the system of FIG. 6 as applied to the back of a patient's head for the stimulation of the occipital nerve for relief of migraine headaches, according to one implementation.

FIG. 7A is a perspective view of the system 200 of FIG. 6 as applied to the back of a patient's head 80 for the stimulation of the occipital nerve for relief of migraine headaches, according to one implementation. A patient or caregiver places the extension electrode 202 on the shoulder or neck 88 of the patient, and applies the tip 131 of the electrode 130 to a therapy site 87 on the back of the patient's head 80 in the vicinity of the occipital nerve. In preferred implementations, the extension electrode 202 includes an adhesive surface that holds the extension electrode 202 against the patient's tissue. As shown, the extension electrode 202 is placed away from the therapy site 87. For example, in the depicted case, the extension electrode 202 is placed at the base of the neck 88. The extension electrode 202 may be placed at any location which is comfortable for the patient, including, but not limited to the shoulder, back, and arm. The device 100 is actuated and adjusted to provide appropriate stimulation levels by increasing and decreasing the current via the buttons 108*a* and 108*b*, for example. An electrical stimulation current flows out of the electrode 130, passes through the therapy site 87, and returns to the device 100 via the extension electrode 202.

Figure 7B:
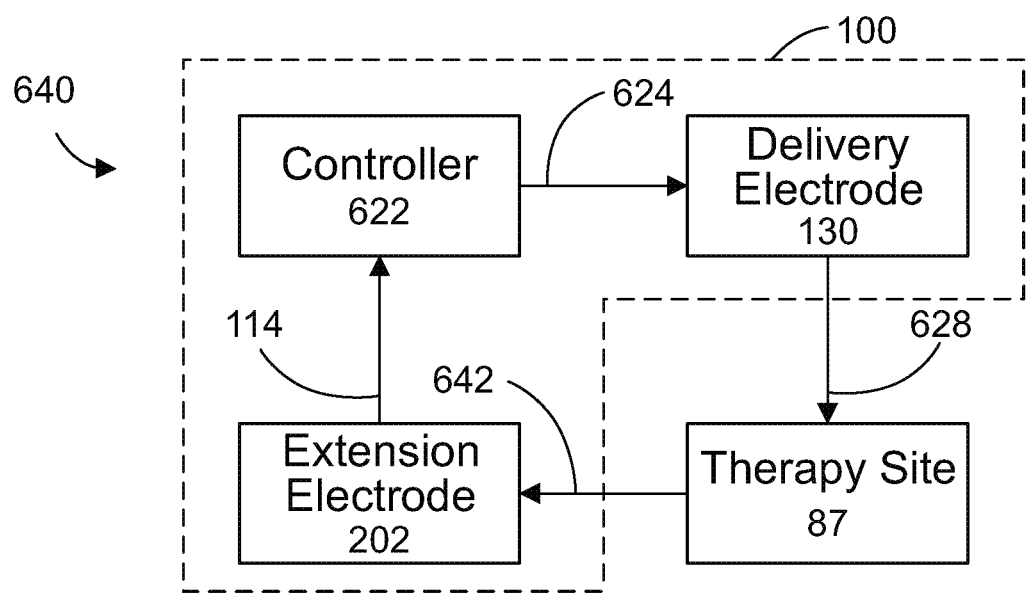
FIG. 7B is a block diagram of an illustrative therapeutic current path associated with an electrical stimulation system, such as the system of FIG. 7A.

FIG. 7B is a block diagram of a therapeutic current path 640 for the delivery of stimulation treatment according to the embodiment of FIG. 7A. The path 640 is similar to the path 620 of FIG. 5B in that it forms a closed electrical circuit for delivering current, with the primary difference being that the path 640 includes an extension electrode 202. As shown, current flows from the controller 622 through the electrode 130, to the therapy site 87, and returns through the extension electrode 202 to the device 100. Instead of flowing through the patient's hand as in current path 620 of FIG. 5B, the current flows through the conductive tissue path 642 disposed between the therapy site 87 and the extension electrode 202. As described above, the extension electrode 202 may be placed at any comfortable location on the body including, but not limited to, the neck and shoulder. The extension electrode 202 is electrically connected to the controller 622 by the lead wire 114.

Figure 8:
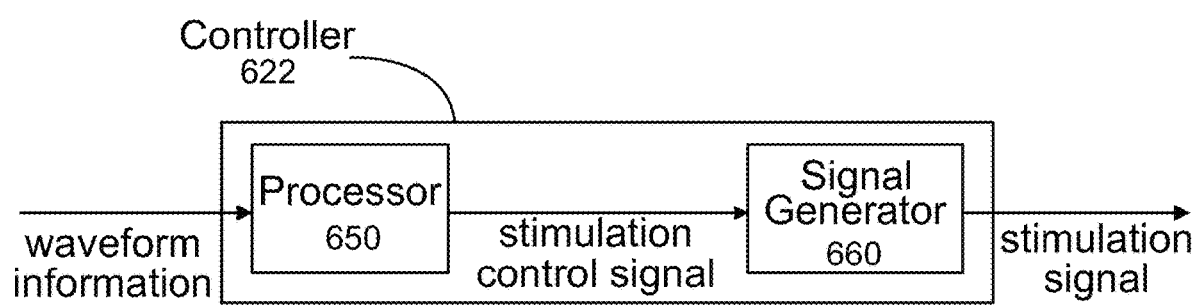
FIG. 8 is a flow diagram of the signal processing performed by a controller included in a hand-held electrical stimulation device.

In preferred implementations, a hand-held electrical stimulation device (such as the device 100 of FIG. 2) is provided with a controller that produces an electrical stimulation waveform with desired characteristics. FIG. 8 is a flow diagram of the signal processing performed by a controller 622 included in such an electrical stimulation device. The controller 622 includes a processor 650 and signal generator 660. Examples of devices that may be used to implement the processor 650 include, but are not limited to, microprocessors, microcontrollers, integrated circuits (ICs), central processing units (CPUs), programmable logic devices, field programmable gate arrays, and digital signal processing (DSP) devices. The processor 650 may be of any general variety such as reduced instruction set computing (RISC) devices, complex instruction set computing (CISC) devices, or specially designed processing devices such as application-specific integrated circuit (ASIC) devices. Examples of devices that may be used to implement the signal generator 660 include, but are not limited to, those described in U.S. Pat. Nos. 4,887,603 and 4,922,908, both by Morawetz et al. and titled MEDICAL STIMULATOR WITH STIMULATION SIGNAL CHARACTERISTICS MODULATED AS A FUNCTION OF STIMULATION SIGNAL FREQUENCY, the contents of which are hereby incorporated by reference in their entireties. In some implementations, the signal generator 660 is a simple modulated pulse (SMP) signal generator. In use, the signal generator 660 is electrically coupled to an output (not shown), such as electrode 130 of FIG. 2, to deliver electrical stimulation therapy to the patient's tissue. The controller 622 may also include or be coupled to a power source, such as a battery (not shown), and actuation switches, such as the buttons 108 of FIG. 2. An example of a suitable battery is a lithium-ion battery having a voltage of about 3.7 to 4.2 volts, although other battery types and voltages are used in other implementations.

As shown in FIG. 8, the processor 650 receives waveform information (for example, from an operator of the hand-held electrical stimulation device) which is used by the processor 650 to output a stimulation control signal. The signal generator 660 receives the stimulation control signal and generates a corresponding electrical stimulation waveform for delivery to the patient. For example, the user may press an actuation button, such as the buttons 108*a* and 108*b* of FIG. 2, or may provide input information by programming the processor 650 through a communications port (e.g., port 164 of FIG. 6) to select or adjust the frequency, amplitude, pulse width, shape, or other characteristic of the electrical stimulation waveform. In certain implementations, the processor 650 receives waveform information from a caregiver's computer or other source. In response to the input waveform information, the processor 650 outputs a stimulation control signal to the on-board signal generator 660. The processor 650 may be programmable (e.g., a programmable microprocessor) and may be configured with software loaded into a memory on-board the hand-held electrical stimulation device. In certain implementations, software is used to program the processor 650 with information about different stimulation control signals that, when generated by the processor 650 and transmitted to the signal generator 660, cause the signal generator 660 to generate different desired electrical stimulation waveforms. These waveforms may have predetermined amplitudes and frequencies that are fixed or that vary in response to inputs to the processor 650. The controller 622 may be programmed to adjust the therapy waveforms over a specific time, for example, according to a programmed schedule. In certain embodiments, the controller output includes a series of different waveforms, for example, a first, low amplitude signal followed by a second, high amplitude signal, or a first signal at a first frequency followed by a second signal at a second frequency. In certain embodiments the waveform parameters vary periodically. In alternative embodiments, the waveform parameters vary at random intervals. The current and voltage can also be varied.

Other configurations and electrical signals are possible, and may be prescribed by a physician or adjusted by the patient. In certain implementations, the controller 622 may be configured to generate one or more electrical stimulation waveforms determined to be appropriate for the patient according to tests performed at the patient's bedside using bedside equipment. For example, a physician could use a bedside electrical stimulation system to determine the appropriate frequency and other parameters of an electrical stimulation waveform that alleviates patient pain. A waveform with those parameters would then be configured into the controller 622 of the hand-held electrical stimulation device (e.g., the device 100 of FIG. 2), and the device could then be sent home with the patient for ongoing use. In certain implementations, the waveform parameters are transmitted to the hand-held stimulation device when the physician or technician connects the device to the bedside equipment by a docking station on the equipment or by a cable connection (e.g., via a USB connection to port 164 of FIG. 6) and actuates the processing circuitry of the bedside equipment via a user interface on the equipment to download the appropriate waveform(s) onto the controller 622 of the device. In some implementations, data transmission between the bedside equipment and the hand-held stimulation device occurs wirelessly, using WiFi, Bluetooth™, another radio frequency communication protocol, or another suitable wireless communication technique. The bedside equipment can also be configured with Internet or other network connectivity to allow data downloading onto the hand-held device.

In some implementations, the controller 622 controller 622 may be programmed to sense impedance and deliver therapy accordingly. For example, the controller 622 can be programmed such that if a lead (e.g., the electrode 130 or conductive surfaces 160 of FIG. 2, the extension electrode 202 of FIG. 6, etc.) loses electrical contact with the patient's tissue during therapy, the controller 622 detects the open circuit and modifies the applied electrical stimulation appropriately until the lead makes contact. For example, the controller 622 may be programmed to shut down the delivery of electrical stimulation to the open lead and to issue an alarm, such as an audible tone. In alternative embodiments, the controller 622 detects a short between two leads. For example, if two leads (e.g., electrode 130 and extension electrode 202) are physically touching or spaced too closely, the controller 622 may be programmed to shut down the delivery of electrical stimulation between the leads and to issue an alarm, such as an audible tone. In certain embodiments, the controller 622 commences delivery of a stimulation signal based on an impedance measurement indicative of the electrode (e.g., the electrode 130) establishing sufficient contact with the skin of the patient.

In some implementations, the controller 622 is programmed to receive feedback from the patient or operator and modify the electrical stimulation waveform applied accordingly. For example, the controller 622 may be programmed to sense electromyographic biofeedback based on muscle activity and regulate therapy accordingly. Other biofeedback such as heart rate or activity levels may also be monitored. In some implementations, the user provides specific feedback to the controller 622. For example, the user can set therapy thresholds (magnitude, duration of therapy) that are stored in a memory accessible to the controller 622. The controller 622 may be programmed to adjust therapy in response to feedback, such as biological activity or impedance measurements.

In some implementations, the controller 622 may be configured to communicate with controllers of other clinical devices to coordinate the therapy or therapies delivered to the user, thereby forming a body area network. This network can be formed through wireless communication and/or conductive communication through the patient's body. For example, the controller 622 may communicate with other stimulation or therapy devices (e.g., TENS, iontophoresis, muscle stimulation, nerve stimulation, drug delivery, or monitoring devices) to provide coordinated therapy to the patient.

As discussed above with reference to the electrical stimulation device 100 of FIG. 2, some of the hand-held electrical stimulation devices described herein generate and deliver current only when sufficient pressure is applied to the electrode by the patient's tissue as detected by a pressure-sensitive switch included in the device. In certain approaches, the electrode may be coupled to a force gauge, pressure gauge, strain gauge, load cell, piezoelectric force sensor, or other force sensor, pressure sensor, or switch. In some implementations, this functionality is achieved with a depressible electrode. Electrical stimulation devices configured with depressible electrodes are now discussed.

FIGS. 9A and 9B are side views of the electrical stimulation device 100 (FIG. 2) with a depressible electrode 230. The electrode 230 may be structurally and functionally similar to the electrode 130, but is connected to a signal generator (e.g., the signal generator 660 of FIG. 8) by a pressure switch mechanism. In preferred implementations, the electrode 230 has a central axis 216 through the tip 231 and shaft 233 of the electrode 230, and is repositionable along the central axis 216. The electrode 230 is in electrical communication with the signal generator of the device 100 only when sufficient pressure is applied to the electrode 230 to cause the electrode 230 to translate along the central axis 216 to connect with an electrical output contact of the signal generator and thereby form a continuous electrical communication path with the signal generator. The electrode 230 may thus be configured as a conductive "push button" that is coupled to the signal generator by a single-pole, single-throw "momentary on" switch to control current flow. For example, FIG. 9A depicts the electrode in a neutral position away from the skin 84 when no pressure is applied between the electrode 230 and the skin 84. FIG. 9B shows the electrode 230 pressed against the skin 84 to form a depressed area 86 of the skin. When the electrode 230 is pressed against the skin 84 with sufficient pressure, the electrode 230 is pushed into the housing 104 of the device 100 along the central axis 216. When repositioned to this upper or closed position, the electrode 230 is electrically coupled with the signal generator and can deliver current to the therapy site.

FIG. 10 is a block diagram of the therapeutic current path 680 associated with an electrical stimulation device according to FIGS. 9A and 9B. As shown, a switch 682 is disposed between the controller 642 and the electrode 230. The switch 682 is a "normally open" single-pole, single-throw switch that functions as a gating switch for delivery of electrical stimulation therapy. The switch 682 remains open with the electrode 230 disconnected from the controller 622 until sufficient pressure is applied to the electrode 230. When sufficient pressure is applied to the electrode 230, the switch 682 is closed, thereby forming a continuous electrical communication path from the controller 622 through the signal line 624, the switch 682, the signal line 626, and the electrode 230. Current flows from the therapy site 87, through the conductive path 630 to the return electrode 614, and back to the controller 622 through the signal line 632. Return electrode 614 may be similar to the conductive surfaces 160 of FIG. 2 or the extension electrode 202 of FIG. 6. Allowing the current to flow to the therapy site only when sufficient pressure is applied to the electrode 230 provides more precise and consistent control of the current being delivered by ensuring that sufficient contact is made between the electrode 230 and the skin 84 (FIGS. 9A and 9B).

FIGS. 11 through 15 are cross-sectional views of illustrative pressure-sensitive switching mechanisms for an electrical stimulation device with a depressible electrode. FIG. 11A depicts the electrode 230 in a neutral position before being placed on the skin 84 of the patient. The shaft 233 of the electrode 230 extends from the connector 102 (FIG. 2). The electrode 230 includes a column 226 which extends into a chamber 229 of the housing 104 (FIG. 2). The electrode 230 also includes a retention surface 222 which contacts the bottom edge 220 of the connector 102 to limit the vertical range of motion of the electrode 230. A compression spring 224 is disposed along the column 226 between the retention surface 222 and the upper edge 221 of the connector 102. As shown, the spring 224 is a coil spring, and may be made of spring metal, but other springs may also be used, including, but not limited to, elastomeric springs.

The chamber 229 includes a contact pad 228 disposed on a wall 235. The contact pad 228 is an electrical conductor that is electrically coupled with a signal line of a signal generator of the device 100 (e.g., the signal generator 660 of FIG. 8). The contact pad 228 may be made of a metal (such as chrome, silver-plated aluminum, or silver chloride), a conductive polymer, or any suitable conductive material. As shown, when the electrode 230 is in a neutral position without contact or pressure at the tip 231 of the electrode 230, the electrode 230 does not come into electrical contact with the contact pad 228. Therefore, the electrode 230 is not in electrical communication with the signal generator of the device 100 and no current is delivered to the patient. In use, the electrode tip 231 is pressed into the patient's skin 84. When pressure is applied, the skin is depressed, the spring 224 is compressed, and the electrode 230 slides vertically within the connector 102 and the chamber 229 of the housing 104. The spring 224 applies a resistive force to the electrode 230, which ensures that sufficient pressure and contact is maintained between the skin 84 and the electrode tip 231. As shown in FIG. 11B, when sufficient pressure is applied, the electrode 230 is repositioned, the column 226 of the electrode 230 touches the contact pad 228 to complete an electrical circuit to the signal generator of the device 100, thus allowing current to flow from the signal generator to the electrode 230 and be delivered to the patient therapy site. The spring constant of the spring 224 determines how much force or pressure must be applied to the electrode 230 to compress the spring 224 and move the electrode 230 to the upper position shown in FIG. 11B and thereby activate the switch mechanism. A spring with a higher spring constant requires more force to compress. The spring 224 can be chosen or designed to set the amount of pressure required to move the electrode to the "on" position to any appropriate level. This configuration ensures that the electrode 230 has sufficient contact with the skin 84 to deliver effective, consistent and controlled electrical stimulation therapy. When the pressure against the tip 231 is released, the spring 224 decompresses and slides the electrode 230 vertically into the neutral position depicted in FIG. 11A.

Figure 11A:
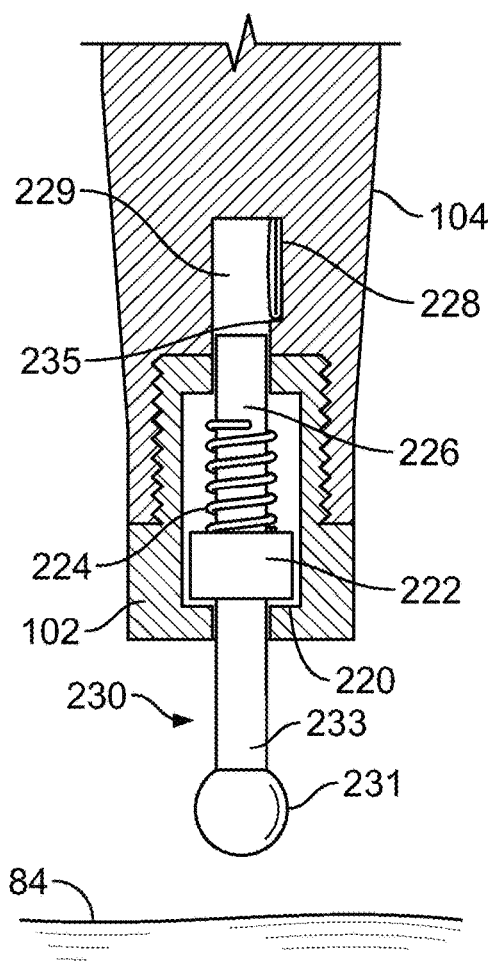
FIGS. 11A-11B, 12A-12B, 13A-13B, 14A-14B, 15A-15B are cross-sectional views of illustrative switching mechanisms for an electrical stimulation device with a depressible electrode.
Figure 11B:
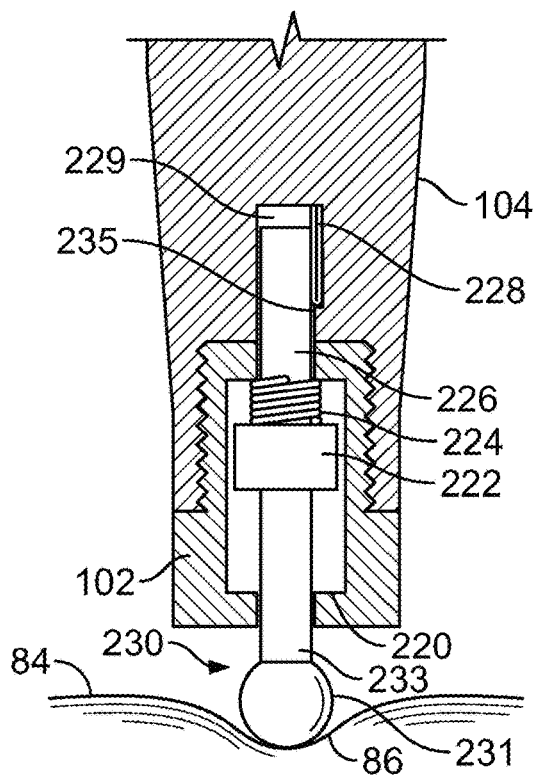
Figure 12A:
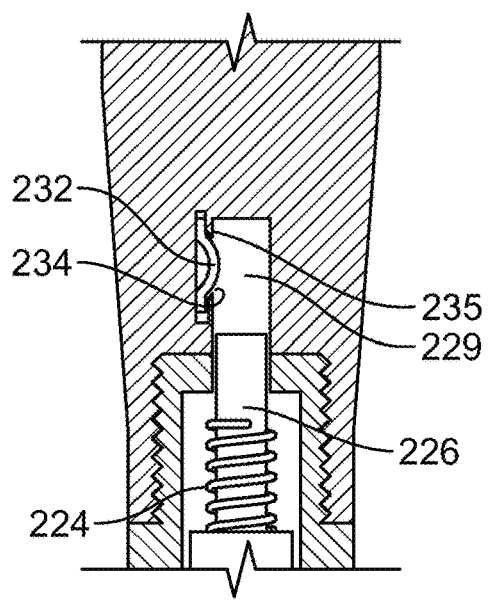
Figure 12B:
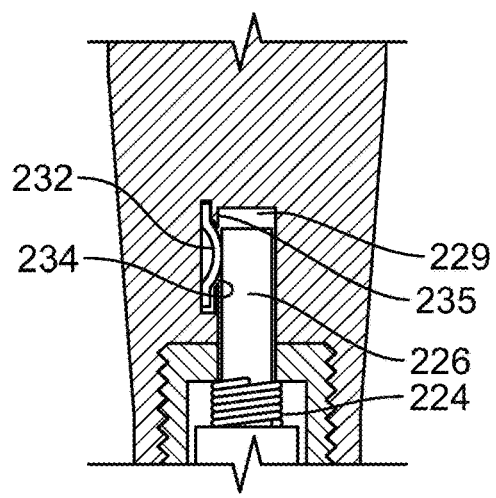

The contact pad 228 of FIGS. 11A and 11B is depicted as a substantially flat contact pad disposed on the wall 235 of the chamber 229. However, contact pads may have other shapes and may be disposed on different parts of the device 100. The contact pads may also change position or shape from the force applied when the electrode 230 is repositioned. For example, as depicted in FIGS. 12A and 12B, the contact pad 232 is substantially arcuate and disposed within an aperture 234 of the wall 235. When pressure is applied to the electrode 230, the compression spring 224 is compressed and the column 226 slides within the chamber 229. When sufficient pressure is applied, the column 226 contacts the contact pad 232 to form an electrical communication path with the signal generator. The arcuate shape of the contact pad 232 ensures sufficient contact between the contact pad 232 and the column 226 by applying a resistive force that flexes or flattens the contact pad 232 when in contact with the column 226. The contact pad 232 is made of a conductive material (for example, a conductive spring steel).

Figure 13A:
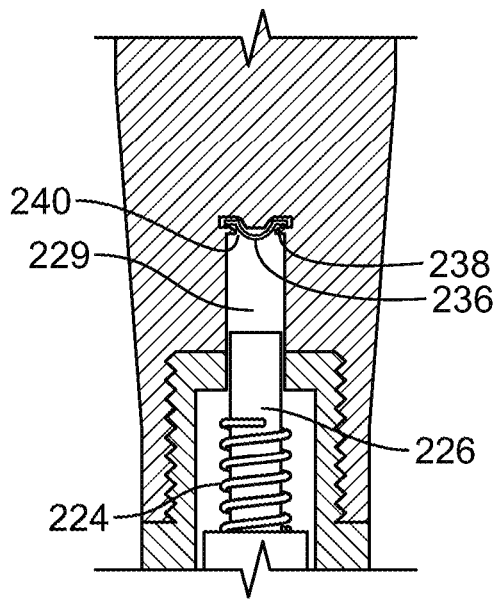
Figure 13B:
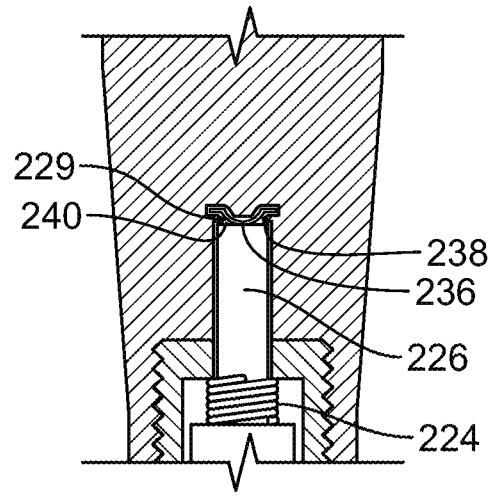

FIGS. 13A and 13B depict an electrical contact pad 236 disposed within an aperture 240 of a top surface 238 of the chamber 229. As discussed with reference to other implementations, when pressure is applied to the electrode 230, the column 226 slides up the chamber 229 and compresses the spring 224. When sufficient pressure is applied, the column 226 contacts the contact pad 236 on the top surface 240 of the chamber 229.

Figure 14A:
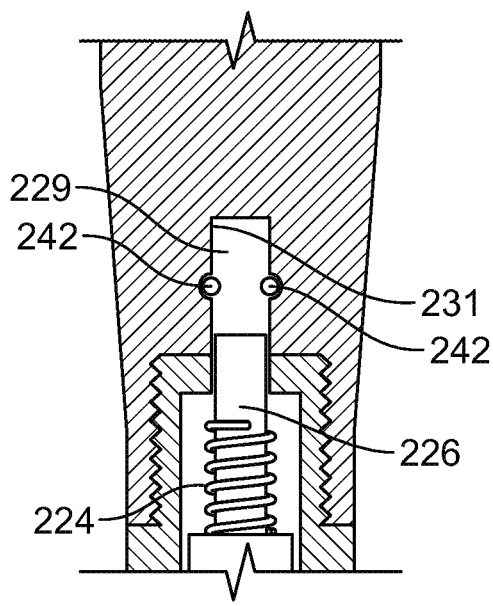
Figure 14B:
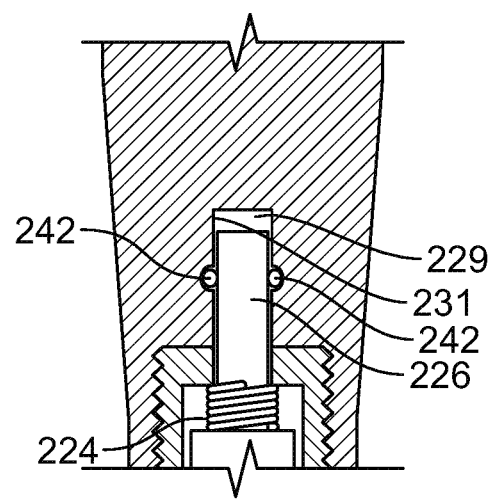

Contact pads may also have a rounded surface shape. FIGS. 14A and 14B depict two rounded contact pads 242. In some implementations, the contact pads 242 are bearings that allow the column 226 to slide within the chamber 229. In certain embodiments the contact pads 242 depress when the column 226 abuts the contact pads 242, as shown in FIG. 14B.

Figure 15A:
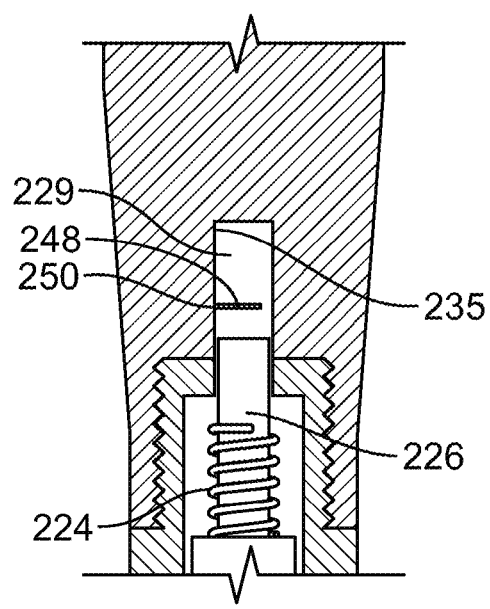
Figure 15B:
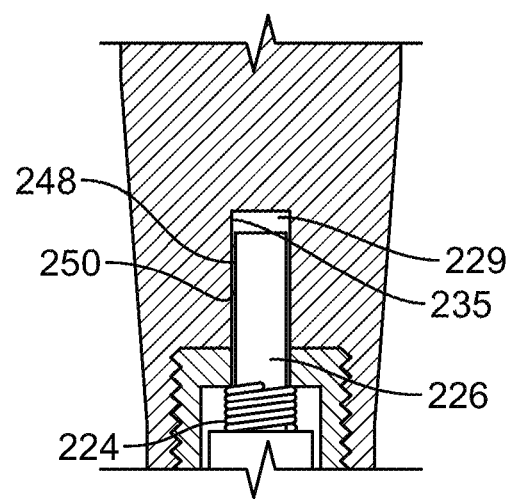

Contact pads may also be hinged. FIGS. 15A and 15B depict a hinged contact pad 248 attached at a hinge point 250 to a wall 231 of the chamber 229. The contact pad 248 is electrically connected to the signal generator of the device. The column 226 slides within the chamber 229 to contact the contact pad 248 and electrically couple the electrode with the signal generator. As depicted, the column 226 pushes the contact pad 228 into the upward position depicted in FIG. 15B.

Figure 1B:
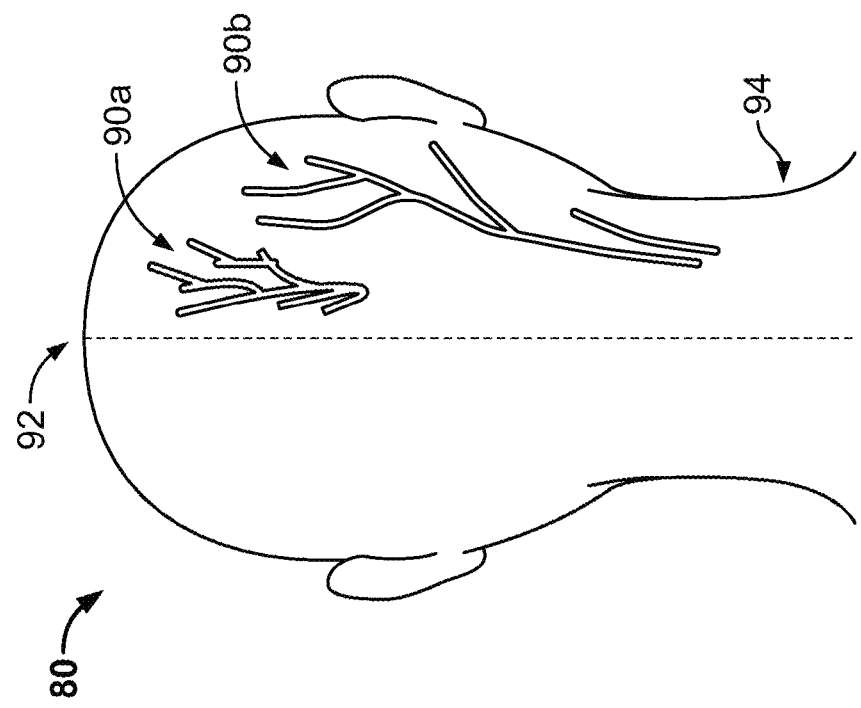
FIGS. 1A-1B illustrate paths along a patient's head indicating the approximate location of certain occipital nerves.
Figure 1A:
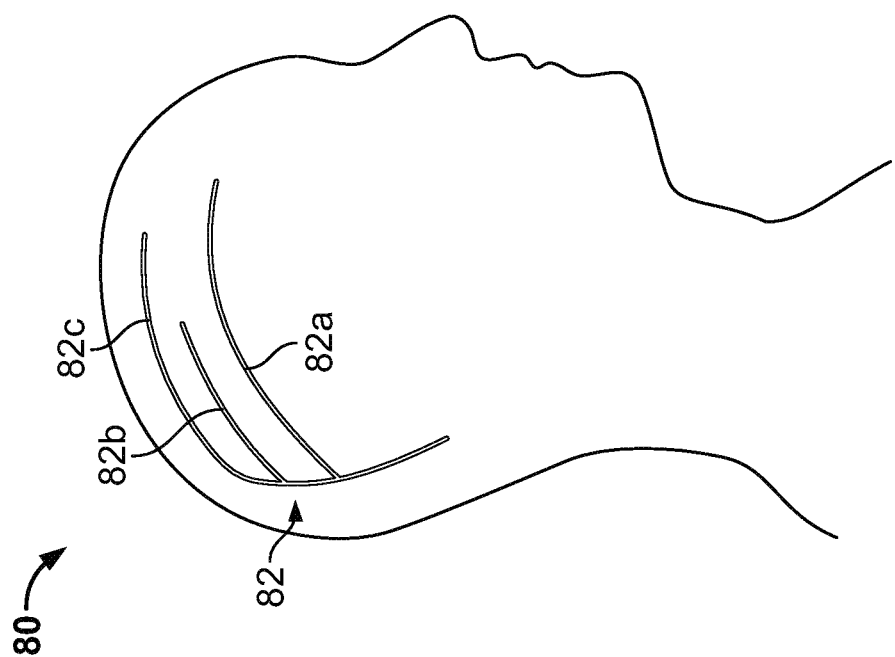
Figure 16A:
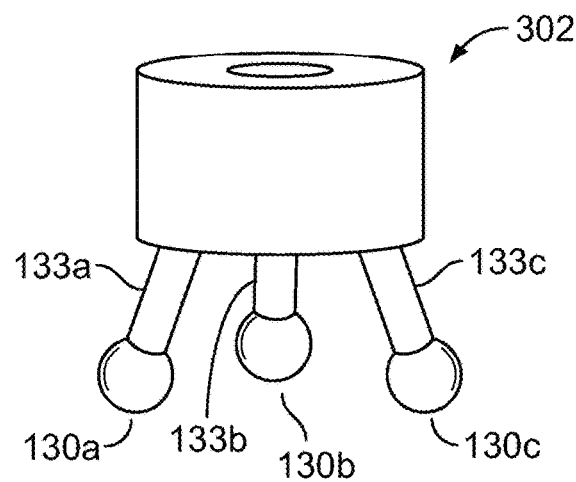
FIG. 16A is a perspective view of an illustrative housing connector with a plurality of electrodes that may be used with an electrical stimulation device.

A number of variations of the device 100 (FIG. 2) and the system 200 (FIG. 6) are possible. For example, the device 100 may be configured with alternative structures for the connector 102 (FIG. 2). FIG. 16A is a perspective view of an illustrative housing connector 302 with a plurality of electrodes 130a-130c. As shown, the electrodes 130a-130c are connected to the housing connector 302 by a plurality of shafts 133a-133c. The electrodes 130a-130c and shafts 133a-133c are composed of a conductive materials, such as metals or conductive polymers. In certain implementations, the electrodes 130a-130c and shafts 133a-133c are rigid, so that when applied to the housing 104 of the device 100, a rigid electrical stimulation device is provided. The plurality of electrodes 130a-130c provide multiple surfaces for contact with the patient's tissue and thus an increased total surface area for delivery of electrical stimulation therapy as compared to implementations in which a single one of the electrodes 130a-130c is used. The plurality of electrodes 130a-130c may be used to reduce the current that flows through any individual electrode to reduce the risk of skin irritation, while maintaining the total current level necessary for effective therapy. Additionally, the plurality of electrodes 130a-130c may be used to provide therapy at multiple points (for example, on multiple branches of the occipital nerve 90a-c as shown in FIG. 1). In certain embodiments, a different stimulation waveform is delivered through each of the plurality of electrodes 130a-130c. Although three electrodes 130a-130c are depicted, any number of electrodes may be used. For example, two electrodes may be used. In certain implementations, at least one electrode of electrodes 130a-130c is a return electrode. In certain implementations, the electrodes 130a-130c are spaced approximately 1-10 mm apart from each other. In certain implementations, the edges of the electrodes 130a-130c are spaced approximately 3.5 mm apart from each other and the centers of the electrodes are spaced approximately 5 mm apart from each other. The electrodes 130a-130c may have any appropriate spacing as determined for effective electrical stimulation therapy. In certain approaches, one or more of the electrodes 130a-130c is repositionable, for example, as described in relation to FIGS. 9A-15B).

Figure 16B:
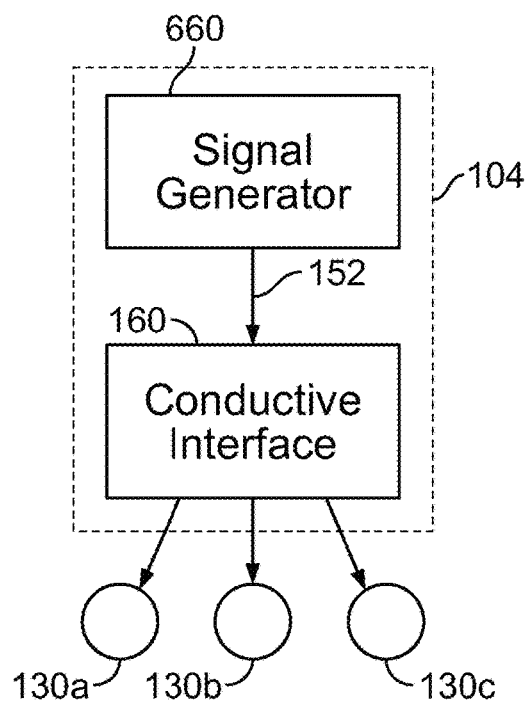
FIGS. 16B-16C are block diagrams of illustrative current paths between a signal generator and the plurality of electrodes of the housing connector of FIG. 16A.
Figure 16C:
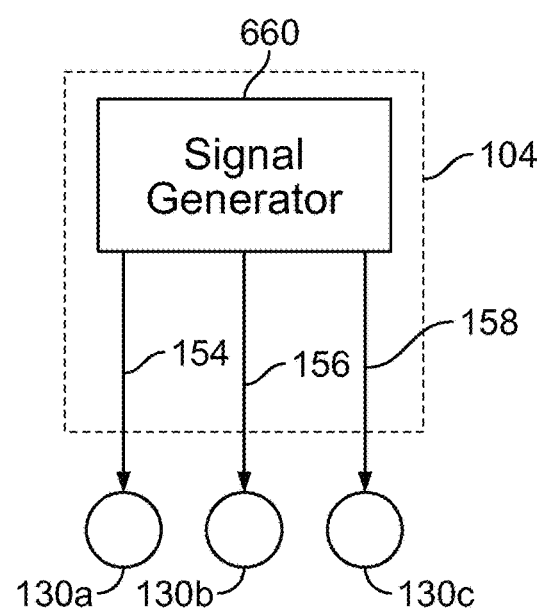

FIGS. 16B and 16C are block diagrams of illustrative current paths between a signal generator 660 (FIG. 8) and the plurality of electrodes 130a-130c of the housing connector 302 of FIG. 16A. In FIG. 16B, a single wire 152 connects the pulse generator 660 to a conductive interface 168, located within the housing 104 of the device 100 (FIG. 2). At the conductive interface 168, the current flow splits into the three different electrodes 130a-130c. In FIG. 16C, the pulse generator 660 independently connects to the electrodes 130a-130c via respective independent conducting lines 154, 156 and 158. Independent conducting lines 154, 156, and 158 allow for increased current carrying capacity for treatment of more acute pain or higher amplitude stimulation. In certain implementations, different stimulation parameters are applied through different ones of the electrodes 130a-130c or subsets of the electrodes 130a-130c. In certain implementations, a first electrode or subset of the electrodes 130a-130c is used as a current delivery electrode and a second electrode or subset of the electrodes 130a-130c is used as a return electrode. In certain implementations, a first subset of the electrodes 130a-130c is connected to the signal generator 660 through a single conductive path and second subset of the electrodes 130a-130c is independently connected to the signal generator 660.

FIGS. 17A-17B is a perspective view of an illustrative housing connector 102 (FIG. 2) with an adapter 310 for receiving an electrode or other stimulation delivery component. In particular, FIG. 17A depicts an adapter 310 that slides over the electrode 130 in the connector 102. The adapter 310 is configured with a distal female jack 314 that receives a male snap 136 from a standard snap electrode 134. The proximal female jack 312 of the adapter 310 snaps into connection with the electrode 130 as the tip 131 extends into the proximal female jack 312. FIG. 17B depicts an adapter 310 connected to the tip 131c of the electrode 130c of the multi-electrode connector 302 of FIG. 16A. The adapter 310 can receive other electrodes or other electrical components through the distal jack 314.

FIGS. 18A-18B are cross-sectional views of illustrative housing connectors with releasable electrodes (i.e., electrodes that are provided separately from and attach to a connector). The housing connector 102 of FIG. 18A has an electrode 330 with a proximal end 324 that seats within a jack 121 of the connector 102, thereby putting the electrode 330 into electrical communication with the wiring and other components of the electrical stimulation device 100 (FIG. 1). In certain implementations, the electrode 330 is releasably connected to the connector 102. For example, the electrode 330 may be removed and replaced for sanitation purposes. The electrode 330 may also be replaceable so that the device 100 may be used with electrodes of different sizes or shapes to provide specific types of therapy or to accommodate user preferences. In certain implementations, a plurality of electrodes 330a-330c attach to a connector 302, as shown in FIG. 18B. Each proximal end 324a-324c of the respective electrodes 330a-330c fits within a jack 320 of the connector 302. The electrodes 330a-330c may be connected through a single conductive path to the signal generator, as depicted in FIG. 16B, or independently connected to the signal generator, as depicted in FIG. 16C. In certain implementations, a first subset of the electrodes 330a-330c are connected to the signal generator through a single conductive path and a second subset of the electrodes 330a-330c are independently connected to the signal generator.

Figure 19A:
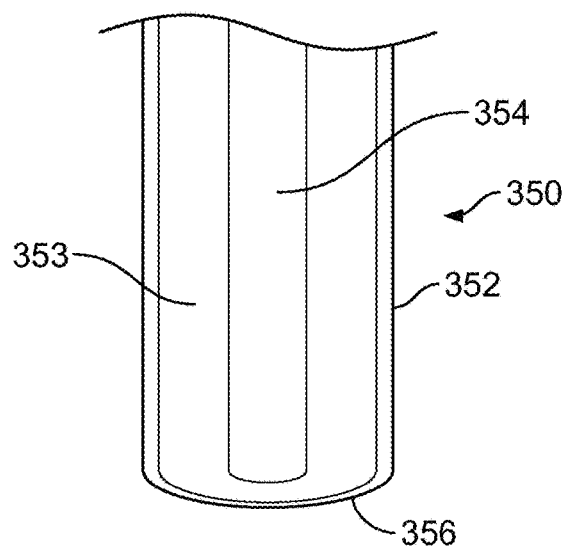
FIGS. 19A and 19B are cross-sectional and bottom views, respectively, of an illustrative concentric electrode system.
Figure 19B:
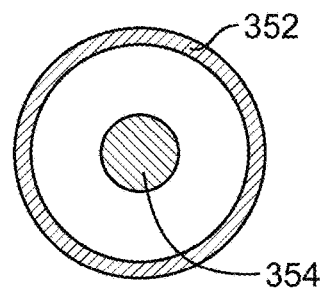

FIGS. 19A and 19B are cross-sectional and bottom views, respectively, of an illustrative concentric electrode system 350 for use with an electrical stimulation therapy system. Concentric electrodes may be used to provide a more compact arrangement of multiple electrodes. The electrode system 350 has a substantially hollow outer electrode 352 with an aperture 356 at the distal end 355. The inner electrode 354 is disposed within the hollow portion 353 of the outer electrode 352. The hollow portion 353 may have a diameter between approximately 1 mm and approximately 25 mm. The distal end 355 of the electrode system 350 is placed on the patient's skin so that both the outer electrode 352 and the inner electrode 354 are in contact with the patient's tissue. FIG. 19B depicts a bottom view of the electrode 350 with the inner electrode 354 disposed within the outer hollow electrode 352. In certain implementations, the inner electrode 354 is used as a delivery electrode to deliver a stimulation current and the outer electrode 352 is used as a return electrode. In alternative implementations, the outer electrode 352 is the delivery electrode and the inner electrode 354 is the return electrode. In certain approaches, the inner electrode 354, the outer electrode 352, or both the inner electrode 354 and the outer electrode 352 are repositionable, for example, as described in relation to FIGS. 9A-15B. Current may flow through the inner electrode 354 and the outer electrode 352 only when sufficient pressure is applied such that the repositionable electrode (e.g., the inner electrode 354, the outer electrode 352, or both the inner electrode 354 and the outer electrode 352) is repositioned to be in electrical communication with a signal generator.

Figure 20A:
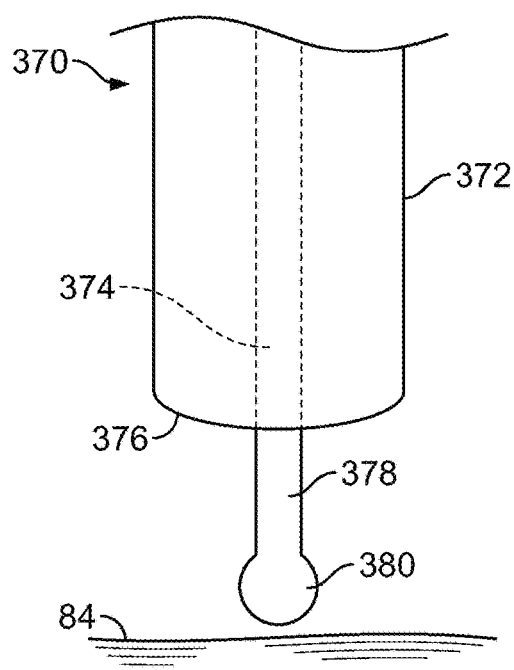
FIGS. 20A-20B are cross-sectional views of an illustrative concentric electrode system in use with a depressible inner element in a non-invasive electrical stimulation device.
Figure 20B:
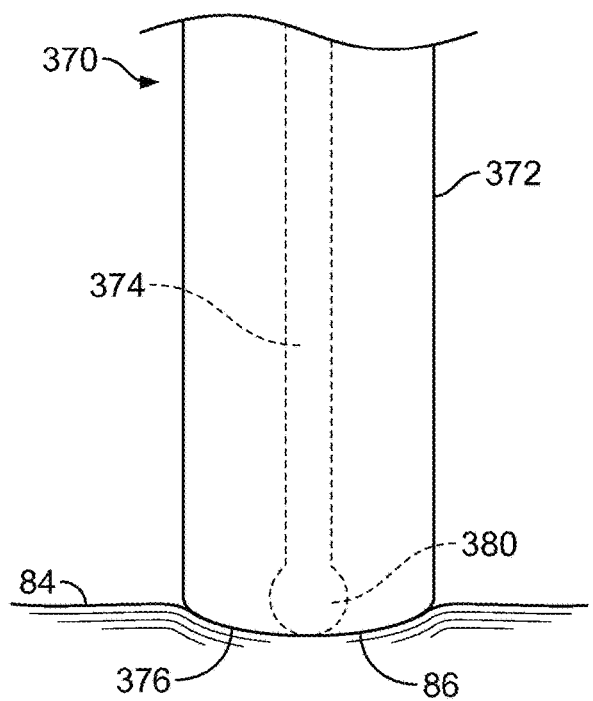

FIGS. 20A and 20B are cross-sectional views of a concentric electrode system 370 with a depressible inner electrode 374 disposed within an outer electrode 372. The shaft 378 of the inner electrode 374 extends through an opening 376 of the outer electrode 372. The inner electrode 374 functions similarly to the depressible electrode 230 described in FIGS. 9A and 9B. Before pressure is applied to the electrode system 370, the tip 380 of the inner electrode 374 extends beyond the opening 376 of the outer electrode 372 and is in a neutral state, disconnected from a signal generator (e.g., the signal generator 660 of FIG. 8). The inner electrode 374 is depressible to control the delivery of current to the patient. As shown in FIG. 20B, when the electrode system 370 is pressed against the skin 84 with sufficient pressure, the skin is depressed at region 86 and the inner electrode 374 is repositioned within the outer electrode 372. When repositioned, the inner electrode 374 electrically connects to the signal generator, and is thereby able to deliver electrical stimulation therapy to the patient. For example, the inner electrode 374 may be switchably connected to the signal generator through any of the mechanisms depicted in FIGS. 11 through 15. In certain embodiments, both the inner electrode 374 and the outer electrode 372 are depressible.

Figure 21A:
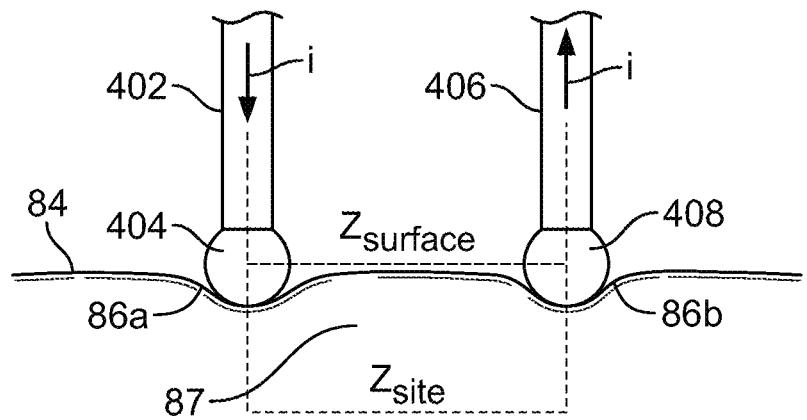
FIG. 21A is a side view of a plurality of electrodes at a therapy site.
Figure 21B:
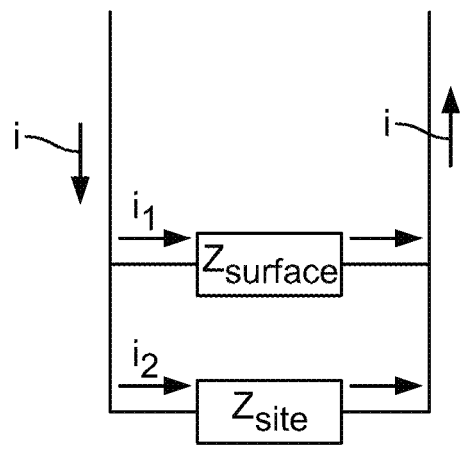
FIG. 21B illustrates the current paths of the configuration of FIG. 21A during the delivery of electrical stimulation therapy.

FIG. 21A is a side view of a first electrode 402 and a second electrode 406 disposed on the surface of the skin 84 and configured to deliver electrical stimulation therapy to a therapy site 87. FIG. 21B depicts the current paths of FIG. 21A during the delivery of electrical stimulation therapy. As shown, the current "i" flows through the first electrode 402 ("delivery electrode" or "active electrode") and returns through the second electrode 406 ("return electrode"). The path of the current between the first electrode 402 and the second electrode 406 is determined primarily by the impedance between the electrodes 402 and 406 along various paths. The various current paths are effectively current dividers for the therapy current. For example, as shown in FIG. 21B, current "$i_1$" and current "$i_2$" are fractional components of the total current "i" delivered by the electrodes 402 and 406. The magnitude of current "$i_1$" and current "$i_2$" are determined by the impedance of the current pathways along the surface and through the therapy site. For example, FIG. 21A depicts a surface impedance "$Z_{surface}$" along the top surface of the skin 84 and a site impedance "$Z_{site}$" through the therapy site 87. If "$Z_{surface}$" is significantly higher than "$Z_{site}$", the magnitude of current "$i_2$" flowing through the "$Z_{site}$" path will be greater than the magnitude of current "$i_1$" flowing through the "$Z_{surface}$" path. The magnitudes of the surface impedance "$Z_{surface}$" and the site impedance "$Z_{site}$" can be adjusted by a variety of therapeutic parameters, including the distance between the electrodes 402 and 406, the pressure applied to the electrodes 402 and 406, the electrical stimulation parameters (e.g., frequency and magnitude), and whether or not conductive gel is used at the electrode-skin interfaces. For example, when the electrode tips 404 and 408 are pressed into the skin 84 to depress the skin 84 in the regions 86a and 86b (FIG. 21A), the tips 404 and 408 have an increased area of contact with the skin 84, which reduces the impedance "$Z_{site}$" between the tips 404 and 408 and the therapy site 87 to drive more current "$i_2$" through the therapy site 87 relative to the current "$i_1$" transmitted along the "$Z_{surface}$" path.

Figure 21C:
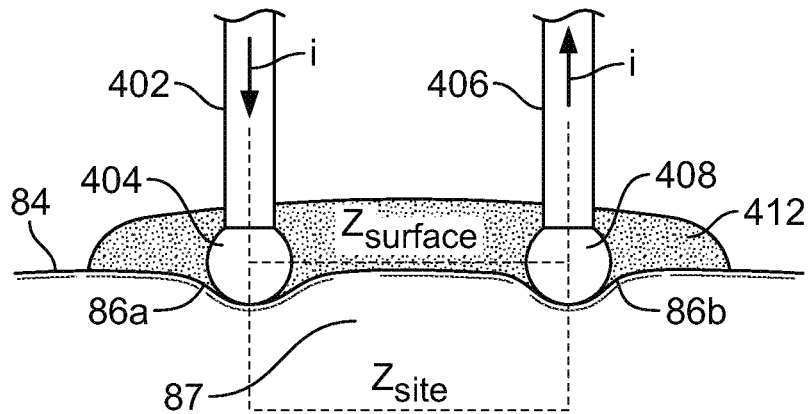
FIG. 21C is a side view of the configuration of FIG. 21A with a conductive gel.

As indicated above, the magnitude of "$Z_{surface}$" can be adjusted by the use of a conductive gel on the skin. FIG. 21C is a side view of a configuration in which a conductive gel 412 coats the surface of the skin 84 on which the first electrode 402 and the second electrode 406 are placed. The conductive gel 412 improves the electrical contact between the tips 404 and 408 of the electrodes 402 and 406 at the skin 84. Because the gel 412 is conductive, "$Z_{surface}$" is reduced relative to the no-gel configuration, and an increased portion of the current "i" flows through the surface path. With conventional gels, "$Z_{surface}$" becomes so low relative to "$Z_{site}$" that very little of the current "i" is delivered to the therapy site 87. To increase the amount of current delivered to the therapy site 87, the electrodes 402 and 406 may be positioned further apart or 44 may be prevented from being simultaneously in contact with the same gel.

Another way to address this situation is to adjust the conductivity of the gel 412 such that "$Z_{surface}$" is sufficiently high so that current "i" is delivered though the path of "$Z_{site}$" to the therapy site 87. The conductivity of the gel 412 may be adjusted by decreasing the relative portions of electrolytes and water in the gel, for example. Tuning the conductivity of the gel 412 may help achieve a more compact arrangement of the delivery electrode and the return electrode. In certain implementations, the electrodes (e.g., the first electrode 402 and the second electrode 406) are spaced approximately 1-10 mm apart. In certain implementations, the edges of the electrodes (e.g., the first electrode 402 and the second electrode 406) are spaced approximately 3.5 mm apart and the centers of the electrodes are spaced approximately 5 millimeters apart. The electrodes (e.g., the first electrode 402 and the second electrode 406) may have any appropriate spacing as determined for effective electrical stimulation therapy. In certain approaches, first electrode 402 and second electrode 406 are concentric electrodes (e.g., as discussed above with reference to FIG. 19).

Figure 22A:
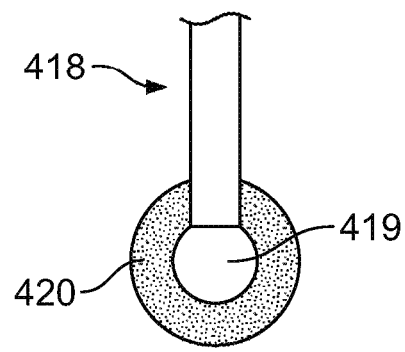
FIGS. 22A-22B are side views of an electrode with an integral conductive gel surface.
Figure 22B:
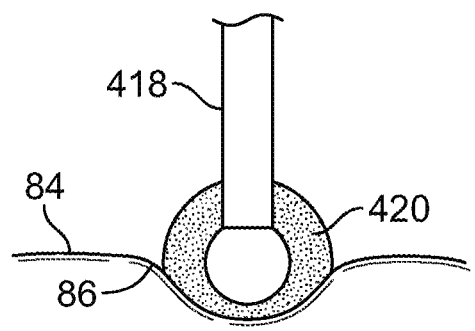

FIG. 22A is a side view of an electrode 418 with an integral conductive gel layer 420 disposed around the tip 419 of the electrode 418. The gel layer 420 is a gel-like solid that is soft, deformable, and substantially conductive, and may be permanently adhered to the electrode tip 419. As depicted in FIG. 22B, when the electrode 418 is placed on the surface of the skin 84, the gel layer 420 conforms to the surface of the skin 84, both depressing the skin 84 in the region 86 and forming a conductive interface between the electrode 418 and the depressed skin region 86. Examples of appropriate materials for the gel layer 420 include silicones, hydrogels, polysaccharides, and other polymers, such as polyvinylpyrollidone, polyethylene oxide, polyvinyl alcohol, polyethylene glycol, polyacrylamide. The gel layer 420 increases the conductivity of the skin-electrode interface, fills contact voids to provide more uniform electrical contact, reduces skin irritation, and provides good electrical coupling. The gel layer 420 may reduce or eliminate the need to apply conductive gels separately to the skin of the patient for the successful delivery of electrical stimulation therapy.

Figure 22C:
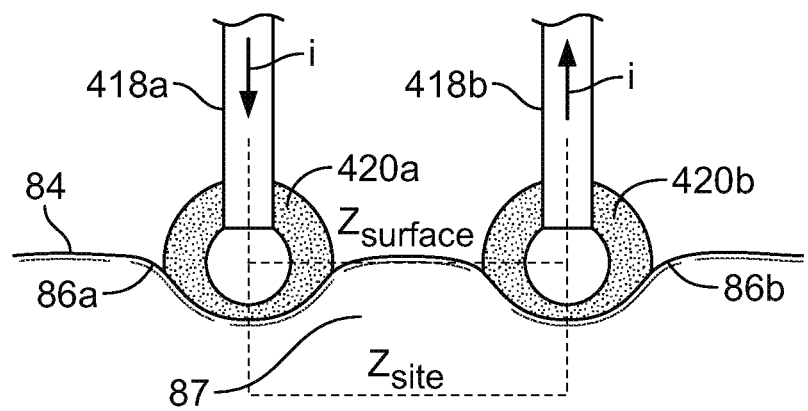
FIG. 22C is a side view of a plurality of electrodes with integral conductive gel surfaces, depicting the current paths proximal to the therapy site.

As depicted in FIG. 22C, the gel layer 420 also allows placement of electrodes near each other (e.g., approximately 1-10 mm apart) without contacting each other or a common conductive gel along the surface of the skin. The gel layer 420a of the electrode 418a contacts the skin at the depressed region 86a, but does not contact the gel layer 420b of the second electrode 418b. The electrodes 418a and 418b can thereby be placed close to each other to provide compact placement of the electrodes without significantly reducing the surface impedance "$Z_{surface}$", thereby ensuring that the delivery of stimulation current "i" results in a sufficient, consistent, controlled current " " 2 delivered to the therapy site 87 through the "$Z_{site}$" pathway (e.g., "$i_2$" as described in relation to FIG. 21B). In certain approaches, electrodes 418a and 418b are concentric electrodes (e.g., as discussed above with reference to FIG. 19).

Closely spaced electrodes (e.g., approximately 1-10 mm apart), such as those depicted in FIGS. 21A, 21C, and 22C may provide improved electrical stimulation therapy and identification of therapy sites. In practice, a user (e.g., a care provider or a patient) can place the electrodes 1 of the device 100 on the skin and easily move the electrode over the skin to find an effective therapy site for applying electrical stimulation. For example, the patient may experience reduced pain when the electrodes are in certain positions, but have no such effect when the electrodes are located in other positions or. In the case of stimulating muscle tissue or nerve connected to muscle tissue, the stimulation current may cause a muscle twitch when the electrodes are in certain positions, but have no such effect when the electrodes are oriented in other positions.

Figure 23A:
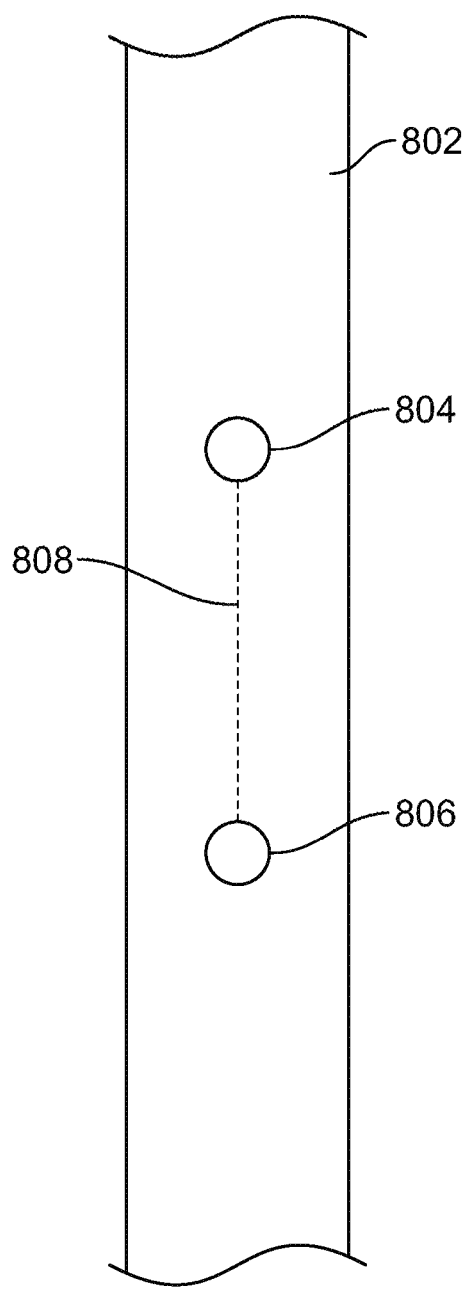
FIGS. 23A-23B are diagrams of electrodes positioned relative to a nerve.
Figure 23B:
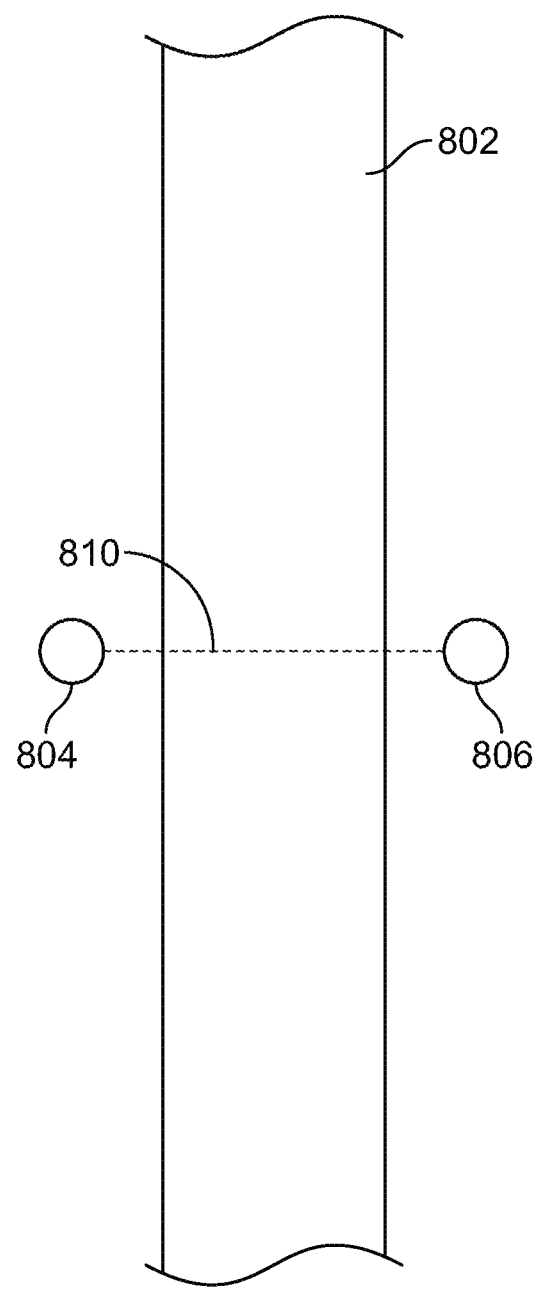

The orientation of the electrodes and resultant current paths in relation to features of a patient's tissue may influence the efficacy of the stimulation therapy. FIGS. 23A and 23B depict the placement of non-invasive electrodes relative to a nerve. In FIG. 23A, a first electrode 804 and a second electrode 806 are spaced closely together (e.g., approximately 1-5 millimeters apart) and placed on the skin (not shown) along and in close proximity to a nerve 802 (which may be similar to nerve paths 90a and 90b of FIG. 1B). The first electrode 804 and the second electrode 806 may be similar to the previously described electrodes 130, 402, 406, and 418. The placement of the electrodes 804 and 806 relative to the nerve 802 forms a conductive current path 808 approximately parallel to and along the nerve 802. When an electrical stimulation wave is applied across the electrodes 804 and 806, current flows between the electrodes 804 and 806 along the current path 808, which causes movement of ions between the electrodes 804 and 806. The movement of ions in close proximity to the nerve 802 initiates depolarization of the nerve 802, which propagates along the nerve 802 resulting in effective "in phase" stimulation. The user may then identify a response or effect of the electrical wave, such as reduced pain or a muscle movement.

FIG. 23B depicts placement of the electrodes 804 and 806 on either side of the nerve 802, which results in a conductive current path 810 across or transverse to the nerve 802. In certain implementations, as shown in FIG. 23B, the electrodes 804 and 806 are spaced away from the nerve 802. When an electrical stimulation wave is applied, current flows between the electrodes 804 and 806, however, due to the position of the electrodes 804 and 806 away from the nerve 802, fewer ions move in the immediate close proximity of the nerve 802. Accordingly, the nerve 802 is insufficiently depolarized to cause propagation along the nerve 802, therefore the stimulation therapy is ineffective or "out of phase." The user may then identify a response or effect of the electrical wave, such as continued pain or lack of muscle movement.

With conventional electrode systems, therapy sites are grossly approximated. In order to compensate for the lack of precision with conventional systems, the stimulation current is typically increased when the therapy is not effective. For example, a user may place an electrode several millimeters from a therapy site, find that the stimulation therapy is not effective, and apply higher currents. Sufficiently high currents may depolarize a nerve, even when the electrodes are in an "out of phase" orientation, but high currents may result in potential side effects, such as discomfort, skin irritation, tissue damage, or burns. High currents also require increased power usage. The systems and methods described herein provide improved accuracy for placing electrodes for more effective, consistent treatment with potentially lower power usage. These systems and methods may be especially useful for treatments requiring high levels of precision, such as along a nerve path for treating migraines or facial paralysis (e.g., Bell's palsy).

In practice, a user may rotate a pair of closely spaced electrodes (e.g. 1-10 mm separation) to accurately identify a therapy site (e.g., therapy site 87) with millimeter precision. The user may find the stimulation effective or "in phase" when the electrodes are in a first position (e.g., along the nerve as depicted in FIG. 23A). The user may rotate the electrodes orientation by approximately 90° to a second position (e.g., straddling the nerve as depicted in FIG. 23B), resulting in "out of phase" stimulation. In certain approaches, the user may rotate or spin the electrodes along the surface of the skin, for example, slowly rotating the electrodes in a circle to identify effective and ineffective placements and orientations for the electrodes. In certain approaches, a user may mark a therapy site and orientation with a marking element, such as a pen or marker tip, which in certain embodiments, is incorporated with the systems and methods described herein.

Figure 24A:
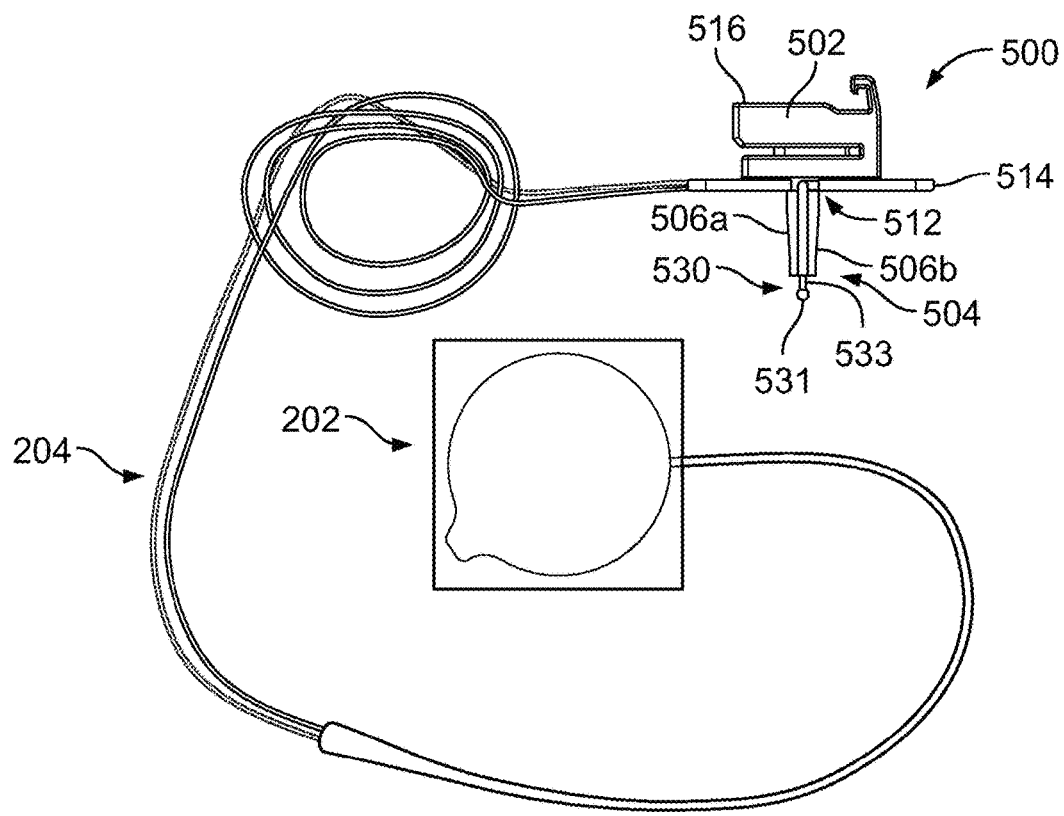
FIGS. 24A-24B are perspective views of an illustrative non-invasive electrical stimulation system.
Figure 24B:
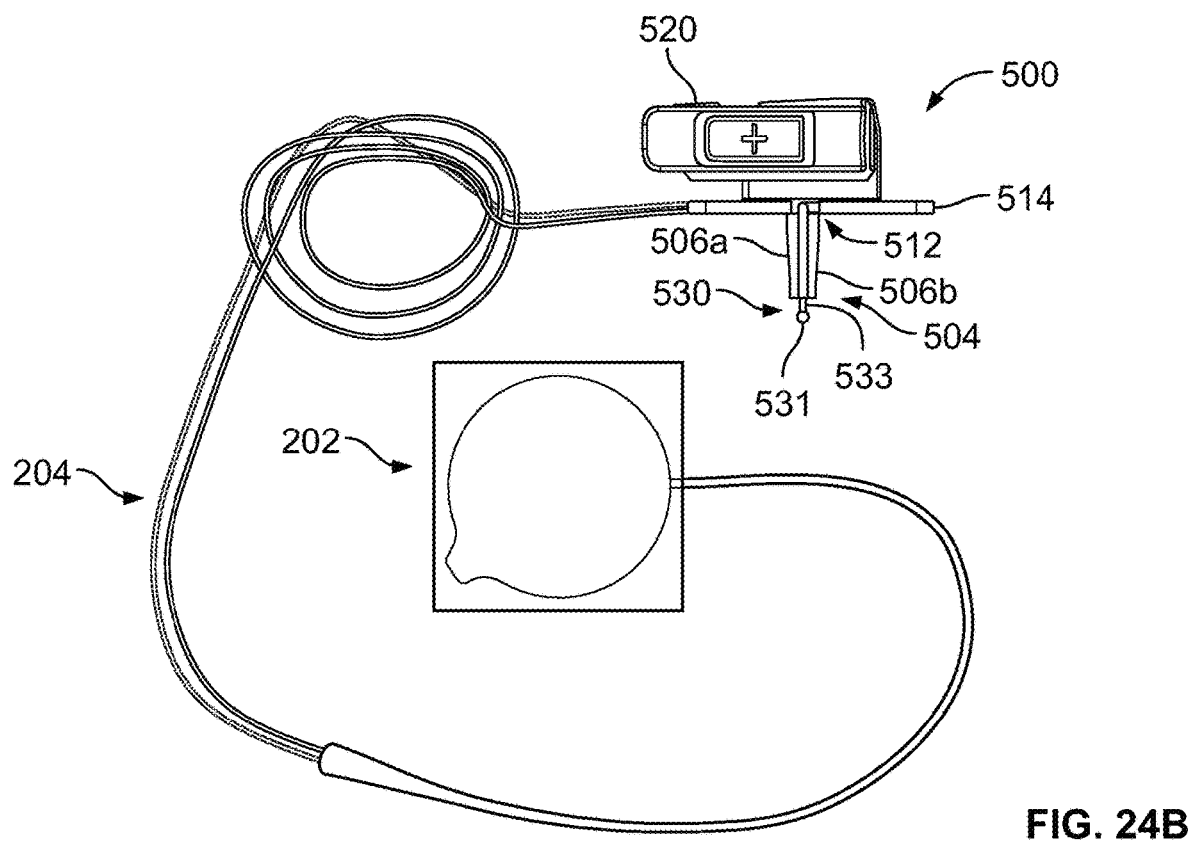

The devices, systems and methods disclosed herein can also be implemented in combination with kits with other electrical stimulation devices. For example, the device described herein can be configured with an adapter that connects with TENS or other electrical stimulation devices (e.g., with the connector and shoe used in the EMPI Active Product sold by DJO through its subsidiary, EMPI Corp.). For example, FIGS. 24A and 24B depict a non-invasive electrical stimulation system 500. The system 500 includes a rigid housing 516, a conductive portion having a rigid shaft 504 and a conductive tip 530, and a plastic or other rigid connector "shoe" 502 that joins the conductive portion to the housing 516. Specifically, the shoe 502 has a proximal end 516 that seats within a controller 520 when the controller 520 is mounted in the shoe 502 as depicted in FIG. 24B, forming an electrical-mechanical interface with the controller 520. The shoe 502 has a distal end 512 that joins with the shaft 504 from which the electrode 530 extends. An intermediate platform 514 (preferably made of a plastic) also facilitates alignment and mechanical connection of the shoe 502 to the controller 520. The connection between the shaft 504 and the shoe 502 seats the shaft 504 in contact with conductive paths, such as wiring, within the shoe 502 that allows current to flow from the controller 520 through the electrode 530. The conductive electrode 530 includes a narrow shaft 533 and a ball or other small contact surface 531, similar to the electrode 130 described above with reference to FIG. 2. Two side fins 506a and 506b are also provided for device stability and handling. An example of a controller and shoe that could be remodeled for use in this system are disclosed in U.S. Patent Application Publication No. 2009/0182393 and U.S. Patent Application Publication No. 2009/0182394, both by Bachinski and titled SYSTEMS AND METHODS FOR THERAPEUTIC ELECTRICAL STIMULATION, the contacts of which are hereby incorporated by reference in their entireties.

Figure 25:
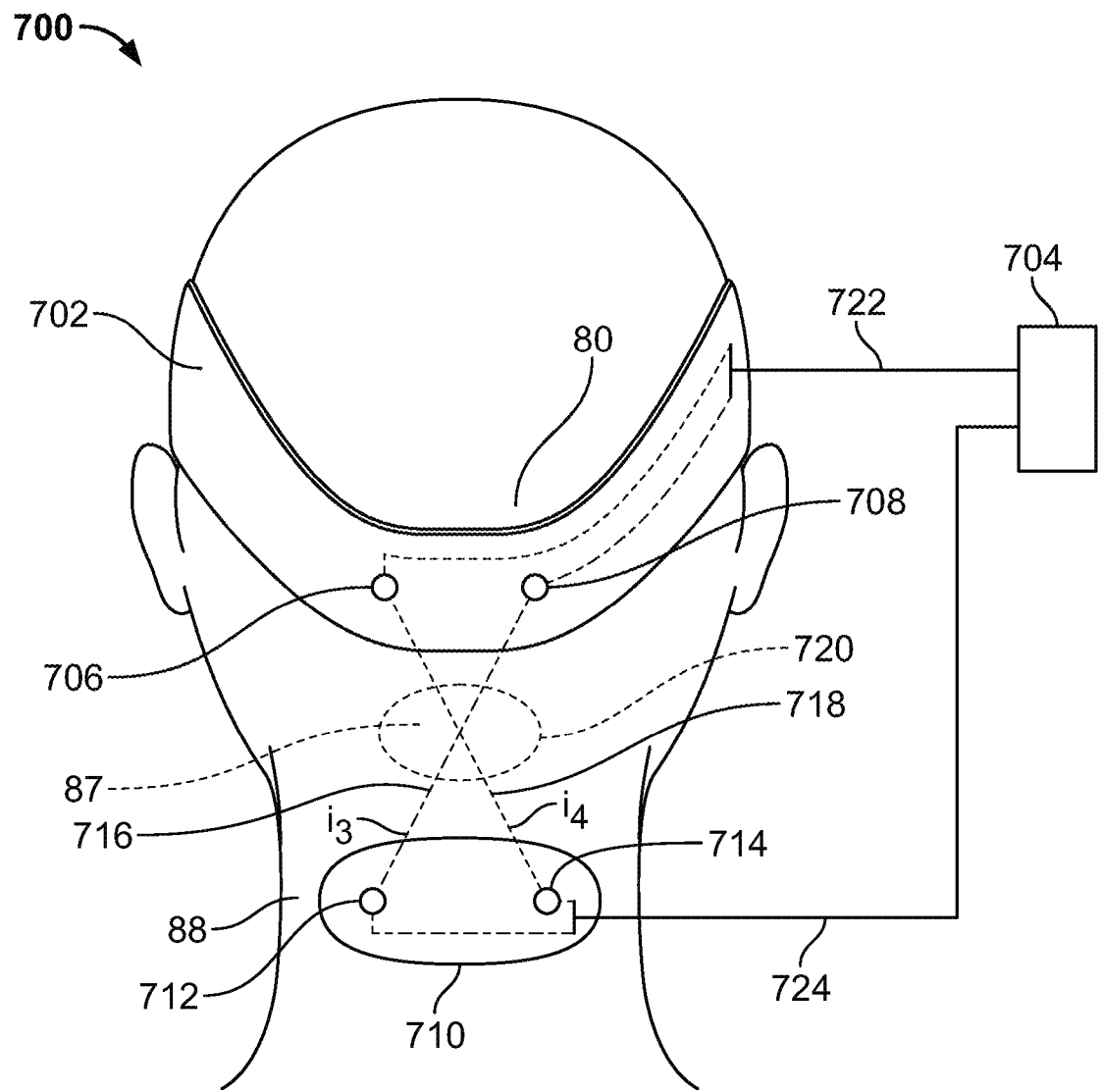
FIG. 25 is a perspective view of a non-invasive electrical stimulation device coupled to a patient's head.

FIG. 25 depicts an embodiment of an electrical stimulation therapy system 700 that may be coupled to the head. System 700 may be useful to allow hands-free electrical stimulation therapy. System 700 may also be useful for applying therapeutic electrical stimulation in the form of interferential stimulation. Interferential electrical stimulation uses at least two higher frequency signals, for example, frequencies between 3500-4500 Hz, although any appropriate frequency may be used. Higher frequency electrical signals penetrate tissue more readily than lower frequency electrical signals. In interferential stimulation, the signals have different frequencies and therefore interfere constructively and destructively in the tissue to form an interference wave or "beat wave" to stimulate the nerve or muscle tissue. The beat wave has a component with a lower frequency than the two original signals (which may have frequencies between approximately 3500 Hz and 4500 Hz, for example). Lower frequency signals do not penetrate tissue as readily as higher frequency signals, but are considered to stimulate nerve or muscle tissue more effectively than higher frequency signals. Accordingly, interferential stimulation provides the benefits of using high frequency signals to penetrate tissue and using low frequency signals to stimulate tissue. Interferential stimulation is described in further detail below in relation to FIG. 26B.

The system 700 includes an electrode support 702 and an electrode patch 710. The electrode support 702 includes a first electrode 706 and a second electrode 708 in electrical communication with a stimulation device 704 via a signal line 722. In certain approaches, the electrode support 702 is configured to wrap around the head 80 of a patient. For example, the electrode support 702 may be a band, as depicted in FIG. 25. Additionally or alternatively, the electrode support 702 may take the form of a hat or helmet. In certain embodiments, the electrode support 702 is adjustable, for example, to enable a comfortable fit on a patient's head. The electrode support 702 may be formed of an elastic material, such as a fabric or polymer. In certain approaches, the electrode support 702 is structured to couple to a portion of the head without wrapping around the head. For example the electrode support 702 may be a patch. Additionally or alternatively, the electrode support 702 may take the form of a cervical collar, and may include or be coupled to the electrode patch 710.

The first electrode 706 and the second electrode 708 are positioned on the electrode support 702 and thereby coupled to patient's head 80. In certain embodiments, the first electrode 706 and the second electrode 708 are adjacently positioned in the electrode support 702 so that both the first electrode 706 and second electrode 708 are positioned on the back of the head when the electrode support 702 is in use. In certain implementations, the first electrode 706 and the second electrode 708 are spaced between approximately 1 mm and approximately 150 mm apart. Although FIG. 25 depicts two electrodes on the electrode support 702, any number of electrodes may be used. For example, the electrode support 702 may include an array of three or more electrodes. The first electrode 706 and the second electrode 708 may be similar to the electrode 130 (FIG. 2). In certain implementations, the first electrode 706 and the second electrode 708 are depressible, for example, as described in relation to FIGS. 9A-15B. Additionally or alternatively, the first electrode 706 and the second electrode 708 may be flat surface electrodes. In certain implementations, the signal line 722 (which couples the first electrode 706 and the second electrode 708 to stimulation device 704) comprises a plurality of signal lines such that the first electrode 706 and the second electrode 708 are electrically independent. For example, the signal line 722 may include multiple wires or may be a multiplex signal line.

The system 700 additionally includes a patch 710 with a third electrode 712 and a fourth electrode 714 in electrical communication with the stimulation device 704 via the signal line 724. In certain approaches, the patch 710 is coupled to the electrode support 702. For example, the patch 710 may be an extension of the electrode support 702. Additionally or alternatively, the system 700 may take the form of a helmet or hat that includes the electrodes 706, 708, 712, and 714. The third electrode 712 and the fourth electrode 714 are positioned on the patch 710 and are structured to couple to the patient's tissue, for example, near the patient's neck 88 or shoulders. In certain implementations, the third electrode 712 and the fourth electrode 714 are adjacently positioned so that both the third electrode 712 and fourth electrode 714 are positioned on the back of the head when the patch 710 is in use. In certain implementations, the third electrode 712 and the fourth electrode 714 are spaced between approximately 1 mm and approximately 150 mm apart. Although FIG. 25 depicts two electrodes on the patch 710, any number of electrodes may be used. For example, the patch 710 may include an array of three or more electrodes. The third electrode 712 and the fourth electrode 714 may be similar to the electrode 130 (FIG. 2). In certain implementations, the third electrode 712 and the fourth electrode 714 are depressible, for example, as described in relation to FIGS. 9A-15B. Additionally or alternatively, the third electrode 712 and the fourth electrode 714 may be flat surface electrodes. In certain embodiments, the signal line 724 (which couples the third electrode 712 and the fourth electrode 714 to the stimulation device 704) comprises a plurality of signal lines such that the third electrode 712 and the fourth electrode 714 are electrically independent. For example, the signal line 724 may include multiple wires or may be a multiplex signal line.

The stimulation device 704 includes a power source (such as a battery) and a controller with a signal generator (such as controller 622 with a signal generator 660 of FIG. 5B) for delivering electrical stimulation therapy. The stimulation device 704 may further include additional components for using the system 700, such as the switches, buttons, and displays described previously. In certain approaches, the stimulation device 704 is a handheld device. In alternative embodiments, the stimulation device 704 is integrated with the electrode support 702 or the patch 710. For example, the system 700 may include a headband, hat, helmet, or patch that includes the stimulation device 704.

The electrode support 702 is placed around the head 80 of the patient with the electrodes 706 and 708 at the back of the head 80. The patch 710 is placed with the electrodes 712 and 714 on the neck 88. The patch 710 may include an adhesive surface for coupling to the neck 88 or other tissue. In practice, the first electrode 706 is electrically coupled with fourth electrode 714. As shown in FIG. 25, a first electrical stimulation signal is applied such that current "$i_4$" flows along the conductive path 718 through the therapy site 87. In certain implementations, the first electrical signal is a periodic waveform with a frequency of approximately 3500-4500 Hz, although any appropriate frequency may be used. For example, the first electrical signal may have a fixed frequency of 4000 Hz. In certain implementations, the frequency of the first electrical signal is adjustable. For example, a user may manually adjust the frequency of the first electrical signal with an actuation switch, such as a thumbwheel. In certain implementations, the stimulation device 704 is programmed to adjust the frequency of the first electrical signal automatically. For example, the stimulation device may automatically sweep the frequency at which stimulation current is delivered. The sweep may be interrupted and frozen when a patient presses a designated button on the stimulation device 704, after which point stimulation will continue to be delivered at the "frozen" frequency. Such a technique allows the patient to identify the frequency at which he or she feels the most therapeutic effect and maintain that frequency throughout the treatment. In some implementations, the "frozen" frequency may be stored in a memory device for future therapy sessions. In another example, the stimulation device may automatically vary the frequency of the electrostimulation to avoid the desensitization of the patient's tissue that may occur when stimulation of a particular frequency is delivered in the same location for an extended period.

The second electrode 708 is electrically coupled with the third electrode 712. As shown in FIG. 25, a second electrical stimulation signal is applied such that current "$i_3$" flows along the conductive path 716 through the therapy site 87. In certain implementations, the path 716 and the path 718 intersect. In certain implementations, the second electrical signal is a periodic waveform with a frequency of between approximately 3500 Hz and approximately 4500 Hz, although any appropriate frequency may be used. In practice, the frequency of the second electrical signal is different than the frequency of the first electrical signal. In certain approaches, the second electrical signal has a frequency that is 1-200 Hz greater or less than the frequency of the first electrical signal. For example, the first electrical signal may have a frequency of 4000 Hz and the second electrical signal may have a frequency of 4100 Hz. In certain implementations, the frequency of the second electrical signal is adjustable. For example, a user may manually adjust the frequency of the second electrical signal with an actuation switch, such as a thumbwheel. In certain implementations, the stimulation device 704 is programmed to adjust the frequency of the second electrical signal automatically.

When the first electrical signal and the second electrical signal are applied, they interfere to form a lower frequency interferential signal (or "beat wave") within the area 720. In certain implementations, the interferential area 720 encompasses the therapy site 87. The resulting interferential signal has a beat frequency equal to the difference in the frequencies between the first and second electrical signals, as described in further detail below. The lower frequency interferential signal stimulates the nerve or muscle tissue at the therapy site 87.

Figure 26A:
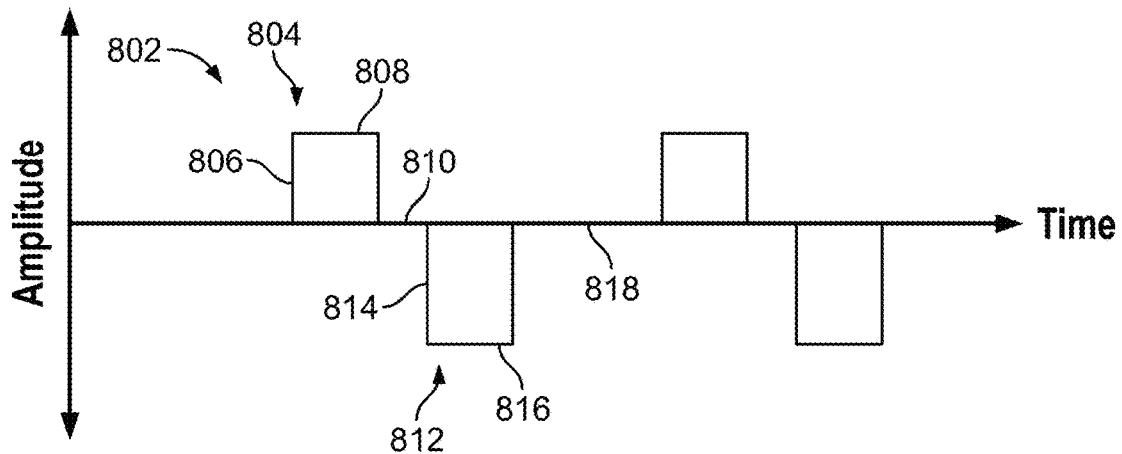
FIGS. 26A-26B are diagrams of example electrical stimulation waveforms.
Figure 26B:
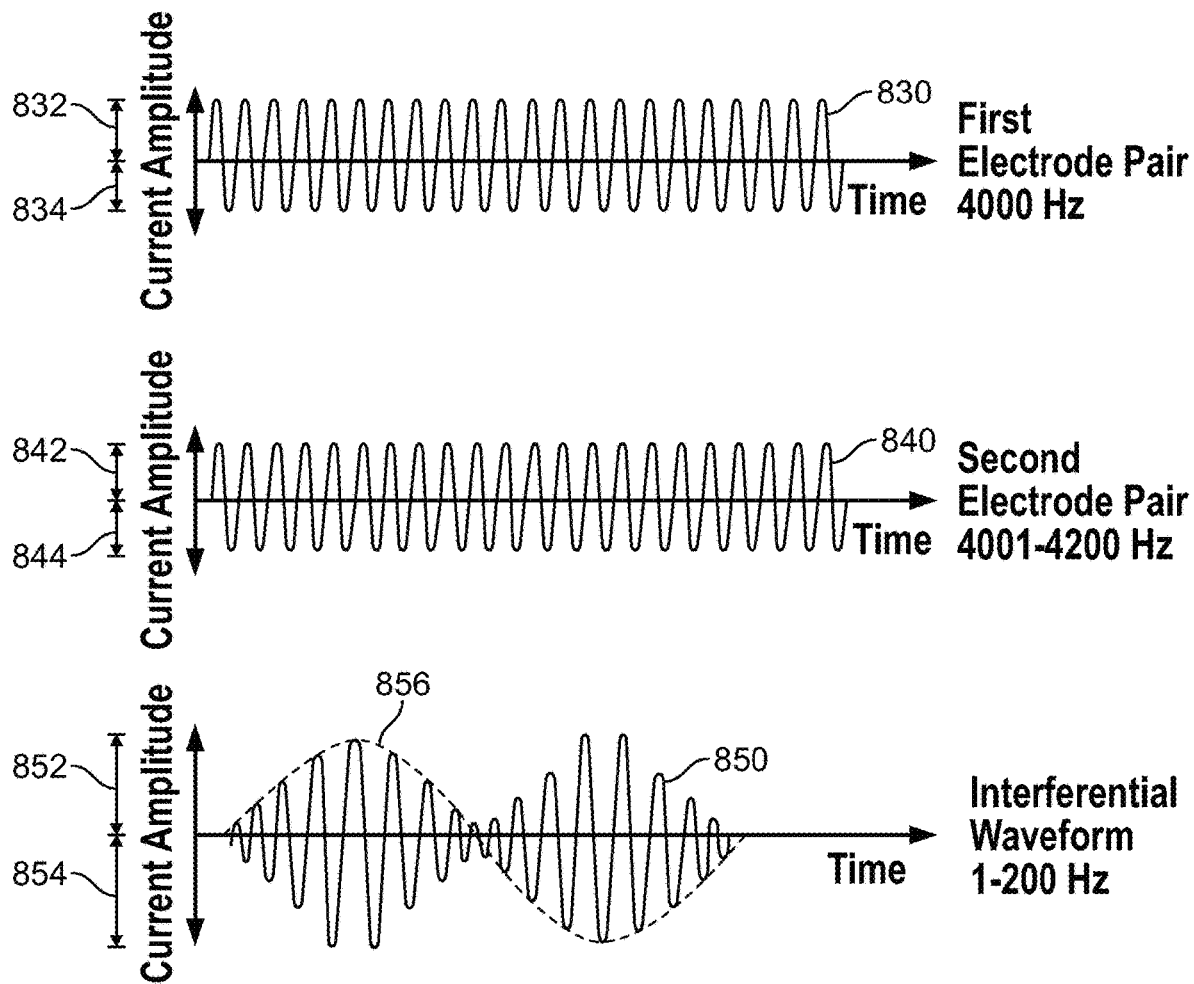

FIGS. 26A and 26B are diagrams of example electrical stimulation waveforms that may be used for therapeutic electrical stimulation of nerve or muscle tissue. FIG. 26A shows a generalized electrical stimulation waveform 802 generated by a signal generator of a controller (such as the signal generator 660 of the controller 622 of FIG. 5B). The waveform 802 of FIG. 26A is a biphasic square wave. In certain approaches, the waveform 802 is a current waveform. Alternatively, the waveform 802 may be a voltage waveform. The waveform 802 has a positive pulse 804 with an amplitude 806 and a pulse width 808. The waveform 802 has an intrapulse interval 810 between the positive pulse 804 and a negative pulse 812. The negative pulse 812 has an amplitude 814 and pulse width 816. The negative pulse 812 is followed by an interpulse interval 818, after which the stimulation pulses are repeated. Each of the pulse parameters (amplitude, width, intrapulse interval, interpulse interval, and shape) is configurable. In certain approaches, the intrapulse interval 810 is approximately zero. In certain approaches, the interpulse interval 818 is approximately zero. In certain implementations, the waveform 802 is symmetrical and charge balanced (i.e., no net positive or negative charge) with a positive pulse 804 having an amplitude 806 and width 808 equal and opposite to the amplitude 814 and width 816 of the negative pulse 812. In certain approaches, the positive pulse 804 and negative pulse 812 have different amplitudes, widths, or shapes, thereby forming an asymmetrical waveform or an unbalanced (i.e., net positive or negative charge) waveform. For example, a monophasic waveform may used, which includes only positive pulses or only negative pulses. In certain approaches, other waveform shapes may be used, including sinusoidal, triangular, stair-step, or other symmetrical or asymmetrical waveform shapes. Additionally, the frequency of the waveform 802 may be changed by adjusting the intrapulse interval, interpulse interval, or both.

In certain implementations, the electrical stimulation waveform used for electrical stimulation, such as the waveform 802, is periodic with a pulse width (e.g., the pulse widths 808 and 816) between about 1 microsecond (μs) and about 700 μs. For example, in certain preferred implementations for migraine treatment, the pulse width is between about 350 μs and about 450 μs, and may be approximately 400 μs. The frequency may be adjusted within a range as desired by the user, particularly between approximately 5 Hz and approximately 4500 Hz. In some cases, an electrical stimulation waveform with a frequency of about 90 Hz is output, while in some cases an electrical stimulation waveform with a frequency closer to 4000-4200 Hz is output. The amplitude may vary according to the pulse width and frequency, for example, in a constant power mode.

FIG. 26B depicts interferential electrical stimulation. As discussed above, interferential electrical stimulation uses at least two higher frequency electrical signals to penetrate tissue, which interfere constructively and destructively to form a lower frequency beat wave to stimulate the nerve or muscle tissue. With interferential electrical stimulation, a first waveform 830 is applied between a first pair of electrodes, such as the first electrode 706 and the fourth electrode 714 of the system 700 depicted in FIG. 25. In certain implementations, the first waveform 830 is periodic with a positive amplitude 832, a negative amplitude 834, and a frequency of approximately 3500-4500 Hz, although any appropriate frequency may be used. For example, the first waveform 830 may have a fixed frequency of 4000 Hz. A second waveform 840 is applied between a second pair of electrodes, such as the second electrode 708 and the third electrode 712 of the system 700 depicted in FIG. 25. In certain implementations, the second waveform 840 is periodic with a positive amplitude 842, a negative amplitude 844, and a frequency of approximately 3500-4500 Hz, although any appropriate frequency may be used. In practice, the second waveform 840 has a frequency that is 1-200 Hz greater or less than the frequency of the first waveform 830. For example, if the first electrical signal has a frequency of 4000 Hz, the second electrical signal may have a frequency of 4100 Hz. In certain embodiments, the frequency of the second electrical signal is adjustable. For example, a user may manually adjust the frequency of the second electrical signal with an actuation switch. In certain implementations, controller 622 is programmed to adjust the frequency of the second electrical signal automatically.

When the first electrical waveform 830 and the second electrical waveform 840 interact in the same area (e.g., interferential area 720 of FIG. 25), they interact both constructively and destructively to form an interferential waveform 850. The interferential waveform 850 is also periodic, as shown by beat wave 856, with a maximum positive amplitude 852 and a maximum negative amplitude 854. The beat wave 856 has a beat frequency equal to the difference in the frequencies between the first electrical waveform 830 and the second electrical waveform 840. For example, when the first electrical waveform 830 has a frequency of 4000 Hz and the second electrical waveform 840 has a frequency of 4100 Hz, then beat wave 856 has a beat frequency of 100 Hz. The interferential waveform 850, with lower frequency beat wave 856, effectively stimulates the tissue. In certain implementations, for example, when only two electrodes are used, the interferential waveform 850 is produced directly by controller 622, instead of through interference of two waveforms.

Figure 27:
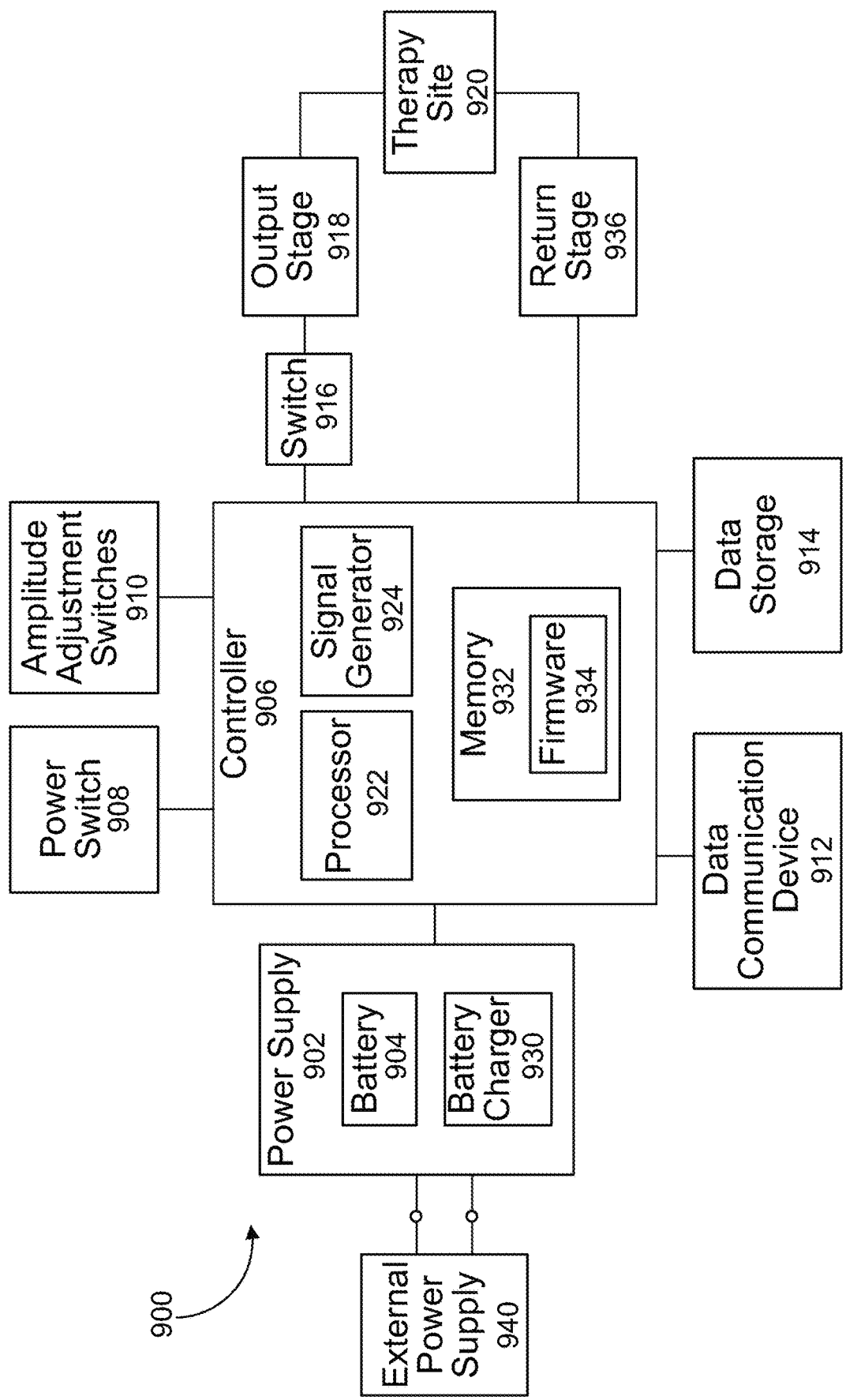
FIG. 27 is a block diagram of electronic components of an electrical stimulation device.

FIG. 27 is a block diagram of electronic components of an electrical stimulation therapy system 900 in accordance with the devices, systems and methods described herein. The system 900, which may be similar to or include the device 100 (FIG. 2) or the system 200 (FIG. 6), includes a power supply 902, a battery 904, a controller 906, a power switch 908, amplitude adjustment switches 910, a data communication device 912, a data storage device 914, a switch 916, an output stage 918, an output 920, and a return stage 936.

During normal operation, the power supply 902 receives power from the battery 904. The battery 904 may be a lithium-ion battery having a voltage of about 3.7 to 4.2 volts, although other battery types and voltages are used in some implementations. The power supply 902 converts the battery power to a desired voltage before supplying the power to other components of the system 900. For example, the power supply 902 may include a step up converter to adjust or increase the voltage of power from the battery 904 to a desired voltage. The power supply 902 also includes a battery charger 930. The battery charger 930 receives power from an external power supply 940 and operates to recharge the battery 904. In some implementations, the external power supply 940 is a home or commercial power supply, such as those available through an electrical power outlet or computer port (e.g., USB). In some implementations, the external power supply 940 is a vehicle power supply, such as a supply accessible through a 12V receptacle. The battery charger 930 may monitor the charge level of the battery 904 (for example, with a thermistor to detect battery temperature). The battery charger 930 may also provide an indicator of the charge level of the battery 904.

The controller 906 is powered by the power supply 902 and controls the operation of the system 900. In particular, the controller 906 generates electrical signals that are provided to the output stage 918. The controller 906 may be similar to or embody the controller 622 described above (e.g., with reference to FIG. 8). The controller 906 includes a processor 922 (which may be similar to or embody the processor 650 of FIG. 8), which processes the input for the therapy (including the stimulation parameters) and communicates with the signal generator 924. The signal generator 924 (which may be similar to or embody the signal generator 660 of FIG. 8) receives an input from the processor 906 and generates a corresponding electrical stimulation waveform that is transferred to the output stage 918 for delivery to the therapy site 920.

The controller 906 is electrically coupled to a power switch 908 and amplitude adjustment switches 910. These switches may be similar to or embody the switches underlying the buttons 908a and 908b of FIG. 2. The controller 906 monitors the state of the power switch 908. When the controller 906 detects that the state of the power switch 908 has changed, the controller 906 turns the system 900 ON or OFF accordingly. The controller 906 also monitors the state of the amplitude adjustment switches 910. When the controller 906 detects that the state of the amplitude adjustment switches 910 has changed, the controller 906 increases or decreases the intensity of electrical signals provided to the output stage 918 accordingly. In certain embodiments, the amplitude adjustment switches 910 are potentiometers. When one or more of the potentiometers is adjusted, the intensity of the electrical signal generated by the signal generator 924 is increased or decreased accordingly.

The controller 906 includes a memory 932. Firmware 934 is stored in the memory 932. The firmware 934 includes software commands and algorithms that are executed by the controller 906 and defines logical operations performed by the controller 906. The software commands and algorithms in the firmware 932 may be used to operate the electrical stimulation device in a desired mode, such as a mode that provides transcutaneous electrical nerve stimulation therapy to the occipital nerve. The controller 906 may use the memory 932 for storing statistics regarding usage of the system 900. For example, information such as type of program, date and frequency of treatments, and intensities applied may be recorded in the memory 932.

Usage statistics may be uploadable from the memory 932 to a data storage 914. The data storage device 914 is a device capable of storing data, such as a memory card or other known data storage device. In some implementations, the data storage device 914 is part of the memory 932. In certain implementations, current and historical operating parameters and physiological parameters (such as heart rate) are stored on the data storage device 914 and can be accessed by a user.

Usage statistics may also be uploadable to a remote data source via the data communication device 912. The data communication device 912 may include one or more wired or wireless communication devices, such as serial bus communication devices (e.g., a Universal Serial Bus communication devices), local area networking communication devices (e.g., an Ethernet communication device), a modem, a wireless area networking communication device (e.g., an 802.11x communication device), a wireless personal area networking device (e.g., a Bluetooth™ communication device), or other communication device. The data communication device 912 can be used to send data to and receive data from another device. For example, the data communication device 912 can be used to download different firmware 934 to the system 900 to alter the operation of the controller 906, and operate the therapeutic electrical stimulation device in a desired mode, such as a mode that provides electrical stimulation or iontophoresis therapy. In certain implementations, a firmware algorithm must be purchased before it can be downloaded by a user. In certain embodiments, a user must access a user interface of a web server or other similar interface before downloading a firmware algorithm. The data communication device 912 can also be used to upload data to another device. For example, the controller 906 may store a therapy log in the data storage device 914. The control processor 906 can be used to upload the therapy log to an external device by transmitting the data log via the data communication device 912.

When the system 900 is ON, the controller 906 generates therapeutic electrical signals, and provides those signals through the output stage 918 to the therapy site 920. The switch 916 opens and closes the electrical coupling between the controller 906 and the output stage 918. The output stage 918 is electrically coupled to an electrode (e.g., electrodes 130, 230, or 330 as described above) that contacts the therapy site 920 to deliver electrical signals to the patient. In certain implementations, as described above, the switch 916 is a pressure-activated switch that closes only when sufficient pressure is applied to an electrode at the output stage 918, thereby forming a continuous electrical path between the controller 906 and the output stage 918. After delivery to the therapy site 920, the electrical signal flows through the return stage 936 back to the controller 906. The return stage 936 is an electrical conductor (e.g., the conductive surfaces 160 of FIG. 2 or the extension electrode 202 of FIG. 6) that contacts the patient to form a complete, continuous conductive path through the therapy site 920 back to the controller 906.

Figure 28:
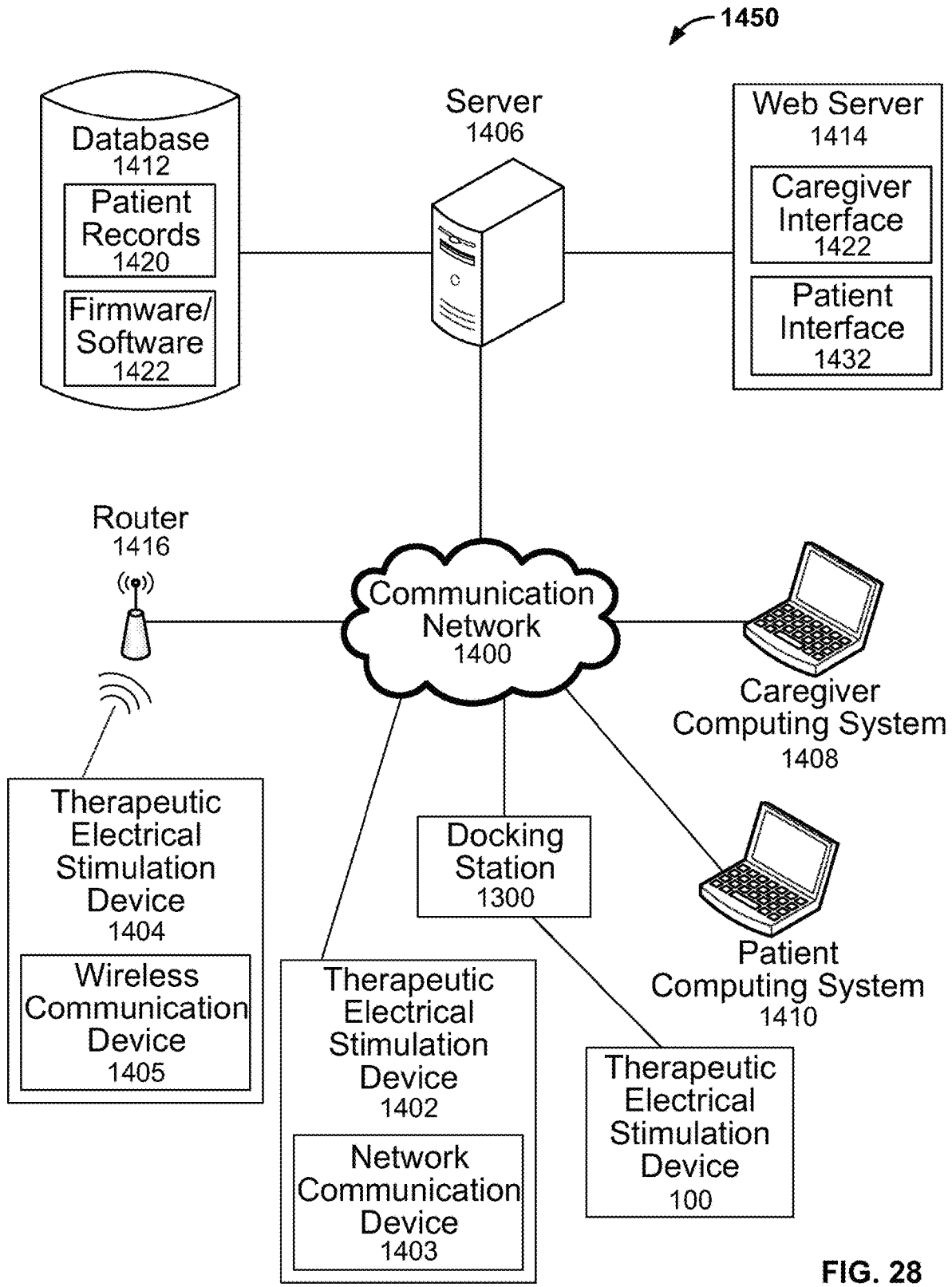
FIG. 28 is a block diagram of an exemplary system for communicating with an electrical stimulation device across a communication network.

FIG. 28 is a block diagram of an exemplary system 1450 for communicating between therapeutic electrical stimulation devices across a communication network 1400. The system includes devices 100, 1402, and 1404. The device 100 is in data communication with a docking station 1300. The device 1404 includes a wireless communication device 1405 in communication with a wireless router 1416. The device 1402 includes a wired network communication device 1403. The system also includes a server 1406, a caregiver computing system 1408, and a patient computing system 1410. The server 1406 includes a database 1412 and a Web server 1414. The system 1450 also includes a wireless router 1416.

The communication network 1400 is a data communication network that communicates data signals between devices. In this example, the communication network 1400 is in data communication with the docking station 1300, the device 1402, the device 1404, the server 1406, the caregiver computing system 1408, the patient computing system 1410, and the wireless router 1416. Examples of networks that may be included in the communication network 1400 include the Internet, one or more local area networks, one or more intranets, one or more near-field networks, one or more peer-to-peer networks, one or more ad hoc networks, and other communication networks.

In some implementations, the devices 100, 1402, and 1404 store, in memory (not shown), data relating to therapy delivery or other operational characteristics of the respective devices. The communication network 1400 can be used to communicate that data to another device. For example, the data from one of the devices 100, 1402 or 1404 may be transferred to the patient computing system 1410 or to the caregiver computing system 1408. Once the data has been transferred to the desired computing system, the data is stored for review and analysis by the patient or the caregiver.

The communication network 1400 can also be used to communicate data from the devices 100, 1402, and 1404 to the server 1406. The server 1406 stores the data in a patient record database 1420. In some implementations, the server 1406 includes a Web server 1414. The Web server 1414 includes a caregiver interface 1430 and a patient interface 1432. Additional interfaces are provided in some embodiments to third parties, such as an insurance company. The Web server 1414 generates web pages that are communicated across the communication network 1400 using a standard communication protocol. An example of such a protocol is hypertext transfer protocol. The web page data is arranged in a standard form, such as hypertext markup language. The web page data is transferred across the communication network 1400 and received by the caregiver computing system 1408, the patient computing system 1410, or both. Browsers operating on the respective computing systems read the web page data and display the web page to the user.

The caregiver interface 1430 generates a web page intended for use by a caregiver. The caregiver interface 1430 allows the caregiver to access the patient records database 1420 and generates reports or graphs to assist the caregiver in analyzing data from the patient records database 1420. In addition, the caregiver interface 1430 provides technical or medical suggestions to the caregiver. In some embodiments, the caregiver interface 1430 also allows the caregiver to request adjustments to an operational mode of a therapeutic electrical stimulation device (such as the devices 100, 1402, and 1404). The operational mode adjustments are then communicated from the server 1406 to the appropriate device, and the device makes the appropriate mode adjustments.

The patient interface 1432 generates a web page intended for use by a patient. In some implementations, the patient interface 1432 allows the patient to access the patient records database 1420 and generate reports or graphs that assist the patient in analyzing data from the patient records database 1420. The patient interface 1432 may provide instructions to assist the patient with uploading data from any of the devices 100, 1402, and 1404 to the patient records database 1420. Other instructions or educational information may be provided by the patient interface 1432, if desired.

In some implementations, the database 1412 includes a firmware repository 1422. The firmware repository 1422 includes data instructions that define the logical operation of a controller for a therapeutic electrical stimulation device of the system 1450. An example of such firmware instructions is the firmware 934 of FIG. 24. The firmware repository 1422 is used in some implementations to store various versions of firmware. For example, when a new firmware version is created, the developer stores the new version of firmware in the firmware repository 1422. The firmware is then communicated to the devices 100, 1402 and 1404 as appropriate. New firmware versions can be automatically distributed to the devices 100, 1402 and 1404, or provided as an option to a patient or caregiver through interfaces 1432 and 1422, respectively. In some embodiments, the patient interface 1432 requires that a patient agree to pay for an upgraded firmware version before the firmware is made available for installation on a device.

In another embodiment, the firmware repository 1422 includes different firmware algorithms. Each firmware algorithm is specifically tailored to provide a specific therapy when executed by devices 100, 1402 and 1404, or is tailored to be used with a particular hardware configuration. Examples of therapies defined by separate firmware algorithms include migraine therapy, TENS, interferential therapy, edema therapy, muscle stimulation, nerve stimulation, iontophoresis therapy, and other therapies. A different firmware algorithm can also be specifically tailored for particular hardware configurations, such as for particular electrode numbers or configurations, for particular data communication devices, for different docking stations, or to accommodate other differences in hardware configuration.

For example, a patient may first obtain an electrical stimulation device, such as the device 100. The device includes a first firmware type that defines an algorithm appropriate for migraine therapy. Later, the patient desires to upgrade the device to cause the device to operate as an iontophoresis therapy device. To do so, the patient uses the patient computing system 1410 to access the patient interface 1432. The patient selects a new firmware algorithm that is designed for iontophoresis therapy. The patient purchases and downloads the firmware associated with the iontophoresis therapy and loads the firmware onto the device. If necessary, an appropriate electrode can be purchased through the patient interface 1432 and delivered to the patient. The electrode is then connected to the device and the new firmware algorithm is executed. The firmware causes the device to provide the desired iontophoresis therapy. In this way, some implementations of the electrical stimulation devices described herein are customizable to provide multiple different therapies.

In some implementations, firmware is specially tailored for providing a therapy to a particular part of the body. As a result, different firmware algorithms are available for the treatment of different body parts and conditions associated with those body parts. Such firmware algorithms can be obtained by downloaded, as described above.

Figure 29:
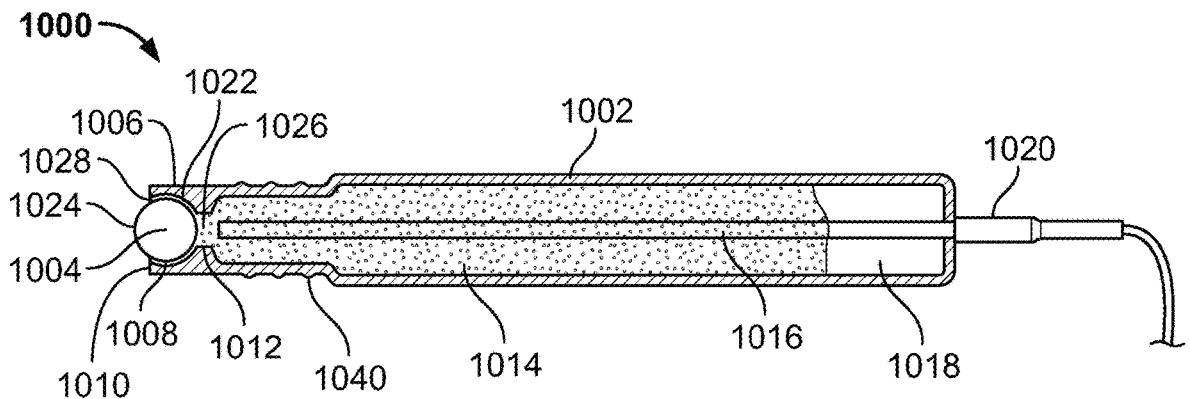
FIG. 29 is a cross-sectional view of a non-invasive electrical stimulation device with an integrated system for delivery of a conductive gel.

In certain approaches, the electrical stimulation devices and systems described herein are configured to deliver conductive gel when pressed against the tissue of a patient. FIG. 29 depicts a cross-sectional view of a non-invasive electrical stimulation device with an integrated system for delivery of a conductive gel. A device with integrated gel delivery may enable the application of gel directly to the region of the therapy site where the electrode is placed and therefore reduce or eliminate the need to apply gel with a separate device or operation. By applying gel directly to the region of the therapy site, the amount of gel delivered may be reduced from conventional devices, which may be particularly helpful, for example, when applying stimulation to a therapy site with hair, such as the back of the head. The device 1000 includes an outer housing 1002, a contact surface 1004 disposed within a socket 1006, and a chamber 1018 that contains a conductive gel 1014 and is in fluid communication with the contact surface 1004. The chamber 1018 can be used to retain and dispense a conductive gel to a patient's tissue (for example, to therapy site 87 as shown in FIG. 5A). In certain approaches, the contact surface 1004 allows current to flow through an exposed portion 1024 of the contact surface 1004 to the patient's tissue. In certain approaches, the contact surface 1004 is an electrode. In certain approaches, the contact surface 1004 is a spherical shape. For example, the contact surface 1004 may be a metallic or conductive polymer ball electrode ("rollerball electrode") formed from chrome, silver-plated aluminum, stainless steel, silver chloride, or any suitable conductive material. Additionally or alternatively, the contact surface 1004 may be structured to allow current to flow through the contact surface 1004, but may not be formed of a conductive material. For example, the contact surface 1004 may include pores or apertures which may contain a conductive material (e.g., a conductive gel) through which current can flow. In certain approaches, the contact surface 1004 is a sponge. In certain approaches, the device 1000 includes a plurality of contact surfaces 1004. In certain approaches, the contact surface 1004 is repositionable, for example, as described in relation to FIGS. 9A-15B, such that the contact surface 1004 is repositioned to be in electrical communication with a signal generator and deliver current only when sufficient pressure is applied to the contact surface 1004.

The contact surface 1004 is held within the socket 1006 between an outer lip 1010 and an inner collar 1012. The outer lip 1010 forms an outer opening 1028 through which the exposed portion 1024 of the contact surface 1004 extends such that the exposed portion 1024 can contact the patient during use. The inner collar 1012 forms an inner opening 1026. The outer opening 1028 and the inner opening 1026 are narrower than the contact surface 1004 such that the contact surface 1004 is positioned within the socket 1006. In certain approaches, the contact surface 1004 is loosely positioned within the socket 1006 such that a spacing 1022 is present between the contact surface 1004 and an inner wall 1008 of the socket 1006. In such approaches, contact surface 1004 may roll or rotate within the socket 1006. In certain approaches, the socket 1006 is repositionable within the housing 1002, thereby making the contact surface 1004 repositionable. For example, as described in relation to FIGS. 9A-15B, the current may flow through the contact surface 1004 only when sufficient pressure is applied to the contact surface 1004, such that the contact surface 1004 is repositioned to be in electrical communication with a signal generator.

The chamber 1018 serves as a reservoir for holding and dispensing the conductive gel 1014. The gel 1014 can flow through the inner opening 1026 such that the conductive gel 1014 is in contact with the contact surface 1004. In certain approaches, as the contact surface 1004 rotates within the socket 1006, the conductive gel 1014 adheres to the contact surface 1004 to form a coating of the conductive gel 1014 on the contact surface 1004, which gel can be delivered to the tissue of a patient from the exposed portion 1024 of the contact surface 1004. In certain approaches (for example, when the contact surface 1004 includes pores), the conductive gel 1014 can flow through the contact surface 1004 to the tissue of a patient. In certain approaches, the housing 1002 includes an aperture so that as gel 1014 is delivered, air can flow into the chamber 1018 to maintain a normal pressure equilibrium and prevent formation of reduced pressure or a vacuum within the chamber. The aperture may include a scrim, which is permeable to air or gas, but impermeable to the gel 1014. In certain approaches, gel 1014 includes a therapeutic agent. For example, gel 1014 may include a molecule or drug for delivery through the skin during stimulation or iontophoresis therapy.

In certain implementations, the device 1000 is configured to deliver electrical stimulation therapy. The device 1000 includes a conductor 1016 positioned within the chamber 1018 and in electrical communication with the conductive gel 1014. For example, the conductor 1016 may be positioned within the conductive gel 1014. The conductor 1016 is formed of an electrically conductive material such as a metal or conductive polymer (e.g., chrome, silver-plated aluminum, silver chloride, stainless steel, or any suitable conductive material). In certain approaches, the conductor 1016 is a rod. In certain approaches, the conductor 1016 is a wire. In certain approaches, the conductor 1016 is integrated with the outer housing 1002. For example, the conductor 1016 may be an inner surface, such as an inner wall, of the chamber 1018 within the outer housing 1002. Since the gel 1014 is conductive, the conductive gel 1014 forms an electrically conductive pathway from the conductor 1016 to the contact surface 1004. In certain approaches, an intermediary conductive material is provided to electrically connect the conductor 1016 to the contact surface 1004. For example, the intermediary conductive material may be placed in the inner opening 1026 to contact both the conductor 1016 and the contact surface 1004. An intermediary conductive material may reduce the electrical impedance of the current path between the conductor 1016 and the contact surface 1004 to reduce power consumption and enable more stable electrical stimulation. The intermediary conductive material may be a conductive polymer, wire, fiber, or mesh. For example, the intermediary conductive material may be steel wool, stainless steel wool, copper wool, bronze wool, or any other suitable conductive material or polymer.

In certain approaches, the conductor 1016 is electrically connected to a cable 1020. In certain approaches, the cable 1020 is electrically connected to a return electrode (not shown). In certain approaches, the cable 1020 is connected to a controller with a signal generator (for example, the controller 622 with the signal generator 660 of FIG. 5B). In certain approaches, a controller and signal generator are integrated into the device 1000 (e.g., as described above in relation to the stimulation device 100 and systems 200, 500, 700, and 900). When the controller of any of these devices or systems produces an electrical stimulation signal, the signal flows through the conductor 1016, the contact surface 1004 and the conductive gel 1014 for delivery to a therapy site on the patient.

The device 1000 may be a consumable or disposable device, or may include consumable or disposable components. In certain approaches, the device 1000 is used as a replaceable cartridge that is coupled within any of the stimulation devices and systems described herein, such as the stimulation device 100 and the systems 200, 500, 700, and 900. For example, the device 1000 may include a coupling structure, such as the threads 1040, to couple the device 1000 to a housing or connector of a stimulation device or system. In certain approaches the device 1000 is repositionable within a housing of a stimulation device or system, for example, as described in relation to FIGS. 9A-15B. For example, the connection between the device 1000 and the housing of a stimulation device or system may include a compression spring. The device 1000 may be removable and/or disposable so that when the gel 1014 is depleted, the device 1000 may be decoupled from an electrical stimulation device or system and replaced. In certain implementations, the device 1000 is refillable, so that when the gel 1014 is depleted, a user may refill the device 1000 with the gel 1014. In certain approaches, the device 1000 is not replaceable, removable, or refillable. In these approaches, when the gel 1014 is depleted, the device 1000 may be disposed of. The chamber 1018 may be removable, disposable, or refillable (e.g., when the chamber 1018 is fixedly coupled to the outer housing 1002). In certain implementations, the device 1000 is integrated with the stimulation device 100 or systems 200, 500, 700, and 900, and when the gel 1014 is depleted, the entire electrical stimulation device or system is disposed of. In certain approaches, the threads 1040 may couple to a cap to protect the contact surface 1004 and prevent the gel 1014 from drying.

Figure 30:
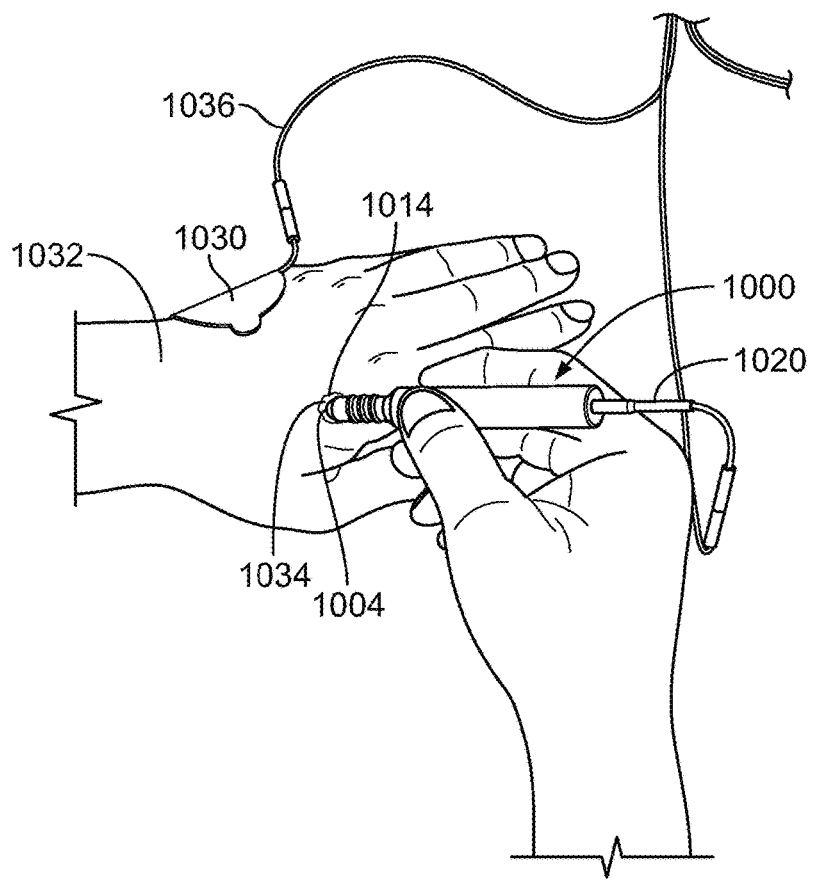
FIG. 30 is a perspective view of a non-invasive electrical stimulation device with an integrated system for delivery of a conductive gel as applied to a patient.

FIG. 30 depicts the device 1000 as applied to a patient. In use, the patient positions the device 1000 on the skin 1032 near a target area 1034, which receives the gel 1014 from the device 1000 from rolling the contact surface 1004. Current flows from a signal generator (not shown) through the contact surface 1004 and into the target area 1034. The current then flows through the patient's tissue to the return electrode 1030 and through the cable 1036 back to the signal generator. In certain approaches, the return electrode 1030 is coupled to the housing of the device 1000 (e.g., as described, for example in relation to the conductive surface 160 of the device 100 of FIG. 2). In certain approaches, the return electrode 1030 extends from the housing of the device 1000 or is positioned near contact surface 1004 (for example, as described above in relation to FIGS. 16-23). The contact surface 1004 is coated with the conductive gel 1014 to provide good electrical coupling for electrical stimulation therapy. In certain approaches, as the user moves the contact surface 1004 along the skin 1032, the contact surface 1004 delivers the conductive gel 1014 to the target area 1034. The device 1000 thereby allows the user to conveniently deliver stimulation therapy with a conductive gel electrical interface, but eliminates the needs to separately apply the gel. Although FIG. 30 is depicted for treating a target area 1034 near or on a patient's hand, the systems and methods described herein may be used to treat target areas located at or near the occipital nerve, face, neck, shoulders, back, arms, legs, feet, or any other portion of the body.

Figure 31:
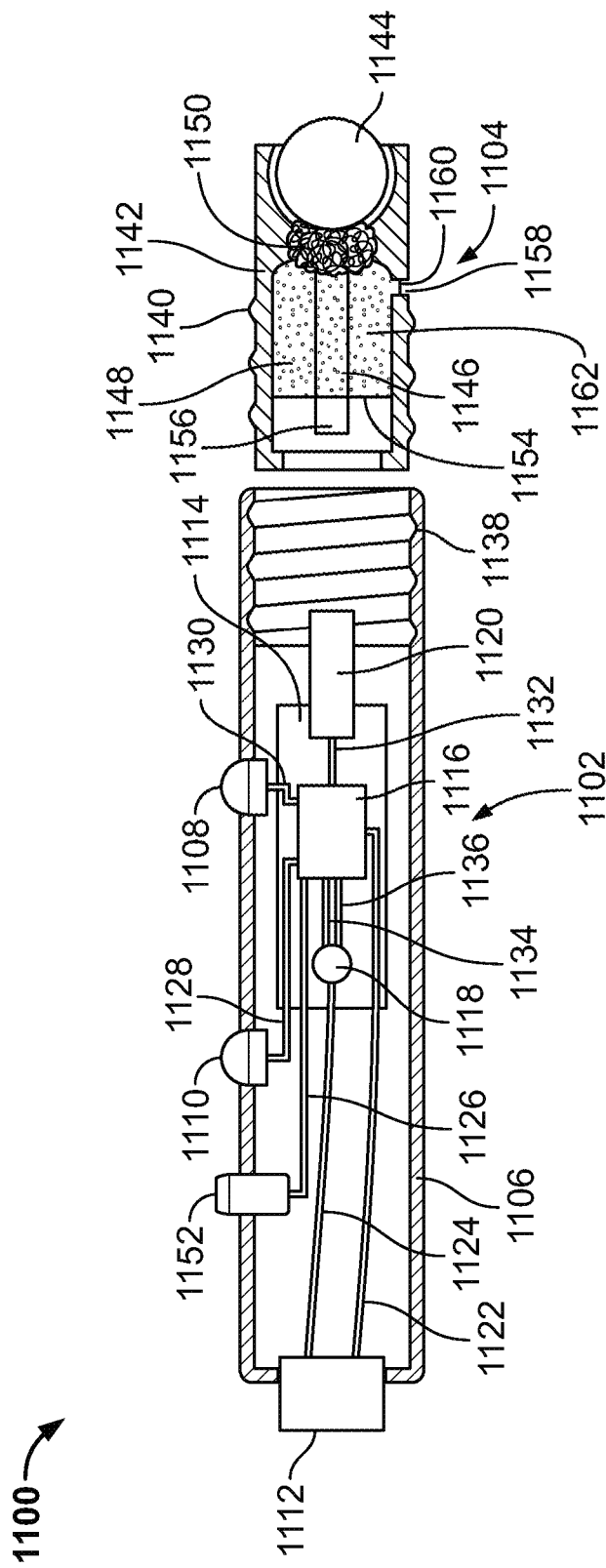
FIG. 31 is a cross-sectional exploded view of a non-invasive electrical stimulation device.

FIG. 31 is a cross-sectional exploded view of a non-invasive electrical stimulation device for providing electrical stimulation therapy to the surface of a patient, such as the back of the patient's head. The device 1100 an upper portion 1102 with integrated electronics and a tip portion 1104 with rollerball electrode 1144 for electrical stimulation and delivery of a gel 1162 from a reservoir chamber 1148. The upper portion 1102 and tip portion 1104 can be releasably connected. For example, in certain approaches, the housing 1106 of the upper portion 1102 includes threads 1138, within which threads 1140 on the housing 1142 of the tip portion 1104 can connect by twisting. In certain approaches, the tip portion 1104 releasably connects to the upper portion 1102 by sliding into the upper portion 1102 with a tight, friction fit. In alternative implementations, the tip portion 1104 may be connected to the upper portion 1102 by a clip, a snap fitting, glue, or another connection mechanism, or may be integral with the housing 1106. The tip portion 1104 may be consumable or disposable. In certain approaches, the tip portion 1104 is coupled to the upper portion 1102 such the tip portion is repositionable and forms an electrical connection only when sufficient pressure is applied to the electrode 1144.

The upper portion 1102 is in the form of a rigid shaft that houses electronics, ports, buttons, and other elements. The housing 1106 of upper portion 1102 may be substantially cylindrical. For example, the housing 1106 may be shaped similar to a pen so that it can be held easily in the hand of a user. A printed circuit board (PCB) 1114 is located within the body portion 1102 to position and connect the electronic components. For example, a controller 1116 is mounted on PCB 1114. The controller 1116 may include a signal generator. Examples of devices that may be used to implement the controller include, but are not limited to, microprocessors, microcontrollers, integrated circuits (ICs), central processing units (CPUs), programmable logic devices, field programmable gate arrays, and digital signal processing (DSP) devices. A battery 1118 or other power source is also connected to the PCB 1114 and controller 1116, for example, with wire 1134 and wire 1136. The wires depicted throughout the embodiments are electrical communication pathways, and may be implemented in other forms, for example, by traces on a PCB (e.g., PCB 1114) or wireless communication methods.

The upper portion 1102 includes buttons 1108 and 1110, which may be used to turn the device on and off, increase and decrease the levels of stimulation, and adjust other therapy settings (e.g., waveform shape, frequency). Buttons 1108 and 1110 are electrically connected to controller 1116, for example, with wires 1128 and 1130. In certain embodiments, one or both of the buttons 1108 and 1110 include potentiometers. When the potentiometer is adjusted, the intensity of the electrical stimulation signal provided by the device 1100 is increased or decreased accordingly.

The upper portion 1102 includes an electrical port 1112 for receiving an electrical connector to recharge the battery 1118 of the device 1100. Port 1112 is electrically connected to controller 1116, for example, with wire 1122 and wire 1124. In some implementations, the port 1112 includes a thermistor to monitor the temperature of battery 1118 during charging to avoid overheating. In some such implementations, the charge level is indicated by a status indicator. In certain implementations, a user connects the device 1100 to bedside equipment via a connection with the port 1112 (which may be, for example, a USB port), to download data from the device 1100 or upload data to the device 1100. In certain embodiments, port 1112 is used to download stimulation protocols or update firmware for the internal controller.

The upper portion 1102 may include a connector 1152 for connecting a return electrode (not shown). Connector 1152 may be electrically connected to controller 1116, for example, with wire 1126. The return electrode may be an extension electrode, for example, as depicted by return electrode 202 in FIG. 6 and FIG. 7. In certain approaches, connector 1152 releasably attaches to the return electrode. Additionally or alternatively, upper portion 1102 may include a return electrode on the outside of the housing 1106, which would contact a user's hand when the user holds device 1100 to apply stimulation. For example, upper portion 1102 may include conductive contact surfaces similar to conductive surfaces 160 as depicted in FIG. 2, FIG. 3, FIG. 5A, FIG. 6, and FIG. 7.

In certain embodiments, upper portion 1102 includes a distal connector 1120 for electrically connecting to the tip portion 1104. Distal connector 1120 is electrically connected to controller 1116, for example, with wire 1132. Distal connector 1120 connects to the proximal end 1156 of the conductor 1146 from the tip portion 1104 when the tip portion 1104 is coupled to the body portion 1102 (e.g., by screwing or sliding the tip portion 1104 into the body portion 1102 as described above). In certain approaches, connector 1120 includes a compression spring, which applies pressure to the conductor 1146 to provide a stable mechanical and electrical connection. In certain approaches, connector 1120 is a spring.

The device 1100 includes a tip portion 1104 with a rollerball electrode 1144. When the tip portion 1104 is connected to the body portion 1102, the electrode 1144 is in electrical communication with the controller 1116 and can deliver electrical stimulation. In certain approaches, the electrode 1144 is repositionable and forms an electrical connection with the controller 1116 only when sufficient pressure is applied to the electrode 1144, for example, as described in relation to FIGS. 9A-15B. The electrode 1144 is in contact with an intermediary conductive material 1150 to form a stable electrical communication pathway from the electrode 1144 to the conductor 1146. The intermediary conductive material 1150 may reduce the electrical impedance of the current path between the conductor 1146 and the electrode 1144 to reduce power consumption and enable more stable electrical stimulation. The intermediary conductive material 1150 may be a conductive polymer, wire, fiber, or mesh. For example, the intermediary conductive material 1150 may be steel wool, stainless steel wool, copper wool, bronze wool, or any other suitable conductive material or polymer. The intermediary conductive material 1150 is porous or fibrous so that the conductive gel 1162 can flow from the chamber 1148 through the spaces within the intermediary conductive material 1150 to the electrode 1144 and to the patient, as described above in relation to FIGS. 29-30. The conductor 1146 is formed of an electrically conductive material such as a metal or conductive polymer (e.g., chrome, silver-plated aluminum, silver chloride, stainless steel, or any suitable conductive material). In certain approaches, the conductor 1146 is a rod. In certain approaches, the conductor 1146 is a wire. In certain approaches, the conductor 1146 is integrated with the housing 1142. For example, the conductor 1146 may be an inner surface, such as an inner wall, of the chamber 1148 within the housing 1142.

The chamber 1148 serves as a reservoir for holding the conductive gel 1162. The chamber 1148 includes a seal 1154 so that the gel 1162 is contained within the chamber 1148 and does not leak out or onto the electrical components. In certain approaches, the housing 1142 of the tip portion 1104 includes an aperture 1158 so that as gel 1162 is delivered, air can flow into the chamber 1148 to maintain a normal pressure equilibrium and prevent formation of reduced pressure or a vacuum within the chamber. The aperture may include a scrim 1160, which is permeable to air or gas, but impermeable to the gel 1162. In certain embodiments, the seal 1154 is permeable to air or gas, but impermeable to the gel 1162 and maintains pressure equilibrium without the need for an additional aperture or scrim.

The devices and systems described herein can be used as diagnostic tools to identify trigger points along the surface of a patient's skin. They can also be used to treat acute or localized pain arising, for example, from insect bites, pinched nerves or other conditions. Veterinarians may be also find these devices and systems useful for treating animals. Other implementations may include the treatment of arthritis in a patient's hands and feet where electrode placement is difficult. In such implementations, a patient can operate the stimulation device with one hand and apply the device to the other hand. Other implementations of the device may include uses in dental applications or on other regions of the body, with the components of the device contoured for specific regions. The devices and systems described herein may be particularly advantageous in facial and dermatology applications in which precise electrical stimulation is desired. For example, the devices and systems described herein may be used to treat facial paralysis, such as Bell's palsy. The device may also be used as a pain assessment tool by the caregiver or by the patient.

Variations and modifications will occur to those of skill in the art after reviewing this disclosure. The disclosed features may be implemented, in any combination and sub combinations (including multiple dependent combinations and sub-combinations), with one or more other features described herein. The various features described or illustrated above, including any components thereof may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A non-invasive electrical stimulation device, comprising:
   a housing;
   a controller comprising a processor and a signal generator disposed within the housing, wherein the processor is configured to receive waveform information and generate a stimulation control signal therefrom, and wherein the signal generator is configured to receive the stimulation control signal from the processor and to generate electrical stimulation waveforms therefrom, wherein the signal generator has a first signal line and a second signal line;
   a plurality of delivery electrodes that are repositionable with respect to the housing, each of the delivery electrodes having a surface for contacting a patient's skin and configured to transmit the electrical stimulation waveforms, and the plurality of delivery electrodes electrically discontinuous from the first signal line when in a first position with respect to the housing and in electrical communication with the first signal line when in a second position with respect to the housing, and wherein each of the delivery electrodes are spaced about 1 mm to about 10 mm apart; and
   a return electrode coupled to the second signal line.

2. The device of claim 1, wherein the housing is configured to be shaped like a pen.

3. The device of claim 1, wherein the return electrode comprises a conductive surface on an exterior of the housing.

4. The device of claim 1, wherein the return electrode comprises:
   an adhesive backing layer configured to be applied to the patient; and
   an electrically conductive surface on the adhesive backing layer.

5. The device of claim 4, further comprising a lead wire connecting the second signal line to the return electrode.

6. The device of claim 1, further comprising:
   a chamber within the housing configured for holding a gel; and
   wherein the delivery electrode comprises a rollerball electrode in fluid communication with the chamber.

7. The device of claim 6, wherein the chamber comprises an aperture configured to promote airflow into the chamber as the gel is delivered.

8. The device of claim 6, wherein the chamber is removable from the housing.

9. A method of delivering electrical stimulation to a patient, the method comprising:
   contacting a return electrode of an electrical stimulation device to a patient;
   contacting a plurality of delivery electrodes of the electrical stimulation device to the patient, wherein each of the delivery electrodes are spaced about 1 mm to about 10 mm apart;
   moving a housing of the electrical stimulation device relative to the patient such that the plurality of delivery electrodes move from a first position wherein the delivery electrodes electrically are discontinuous from a first signal line of the electrical stimulation device to a second position wherein the delivery electrodes are in electrical communication with the first signal line; and
   applying an electrical stimulation waveform using a controller comprising a processor and a signal generator disposed within the housing, wherein a signal generator disposed within the housing, wherein the processor is configured to receive waveform information and generate a stimulation control signal therefrom, and wherein the signal generator is configured to receive the stimulation control signal from the processor and to generate electrical stimulation waveforms therefrom with the return electrode and the delivery electrode in the second position.

10. The method of claim 9, wherein the housing is configured to be shaped like a pen.

11. The method of claim 9, wherein the return electrode comprises a conductive surface on an exterior of the housing, and contacting the return electrode of the electrical stimulation device to the patient comprises holding the housing such that the conductive surface contacts the patient.

12. The method of claim 9, wherein the return electrode comprises:
   an adhesive backing layer configured to be applied to the patient; and
   an electrically conductive surface on the adhesive backing layer.

13. The method of claim 12, wherein contacting the return electrode of the electrical stimulation device to the patient comprises adhering the return electrode to the patient.

14. The method of claim 12, wherein the electrical stimulation device further comprises a lead wire connecting the second signal line to the return electrode.

15. The method of claim 9, wherein the electrical stimulation device further comprises:
   a chamber within the housing configured for holding a gel; and
   wherein the delivery electrode comprises a rollerball electrode in fluid communication with the chamber.

16. The method of claim 15, wherein the chamber comprises an aperture configured to promote airflow into the chamber as the gel is delivered.

17. The method of claim 15, wherein the chamber is removable from the housing.

18. The method of claim 17, further comprising inserting the chamber into the housing.

19. The method of claim 15, further comprising filling the chamber with the gel.

\* \* \* \* \*

UNITED STATES PATENT AND TRADEMARK OFFICE
CERTIFICATE OF CORRECTION

| | |
|---|---|
| PATENT NO. | : 11,439,820 B2 |
| APPLICATION NO. | : 16/571685 |
| DATED | : September 13, 2022 |
| INVENTOR(S) | : Thomas Jerome Bachinski |

It is certified that error appears in the above-identified patent and that said Letters Patent is hereby corrected as shown below:

In the Specification

Column 24, Line 43, Delete ""it"" and insert -- "$i_1$" --.

Column 27, Line 35, Delete "example," and insert -- example; --.

Column 41, Line 46, Delete "thereof" and insert -- thereof, --.

Signed and Sealed this
Twenty-seventh Day of December, 2022

Katherine Kelly Vidal
*Director of the United States Patent and Trademark Office*